United States Patent
López-Belmonte Encina et al.

(10) Patent No.: US 8,361,509 B2
(45) Date of Patent: *Jan. 29, 2013

(54) PHARMACEUTICAL DOSAGE FORMS FOR THE RELEASE OF ACTIVE COMPOUNDS

(75) Inventors: Iván López-Belmonte Encina, Madrid (ES); Ibon Gutierro Aduriz, Granada (ES); Philippe Maincent, Nancy (FR)

(73) Assignee: Laboratorios Farmacéuticos Rovi, S.A., Madrid (ES)

( * ) Notice: Subject to any disclaimer, the term of this patent is extended or adjusted under 35 U.S.C. 154(b) by 11 days.

This patent is subject to a terminal disclaimer.

(21) Appl. No.: 13/355,763

(22) Filed: Jan. 23, 2012

(65) Prior Publication Data

US 2012/0189698 A1 Jul. 26, 2012

Related U.S. Application Data

(60) Division of application No. 12/779,556, filed on May 13, 2010, now Pat. No. 8,257,744, which is a continuation-in-part of application No. PCT/EP2008/065499, filed on Nov. 13, 2008, and a continuation-in-part of application No. 10/332,351, filed as application No. PCT/FR01/02159 on Jul. 5, 2001, now Pat. No. 8,052,998.

(30) Foreign Application Priority Data

Jul. 7, 2000 (FR) ..................................... 00 08902
Nov. 14, 2007 (EP) ..................................... 07380319

(51) Int. Cl.
*A61K 9/14* (2006.01)

(52) U.S. Cl. .................. 424/489; 424/499; 424/500
(58) Field of Classification Search ........... 424/489–495
See application file for complete search history.

(56) References Cited

U.S. PATENT DOCUMENTS

| 5,151,273 | A | 9/1992 | Korsatko-Wabnegg et al. |
| 5,490,990 | A | 2/1996 | Grabowski et al. |
| 5,622,657 | A | 4/1997 | Takada et al. |
| 5,629,011 | A | 5/1997 | Illum |
| 5,686,113 | A | 11/1997 | Speaker et al. |
| 6,475,493 | B1 | 11/2002 | Mulye |
| 2005/0013866 | A1 | 1/2005 | Maincent et al. |
| 2005/0020539 | A1 | 1/2005 | Ajani et al. |

FOREIGN PATENT DOCUMENTS

| FR | 2769853 | 4/1999 |
| WO | WO92/11844 | 7/1992 |
| WO | WO9414420 | 7/1994 |
| WO | WO96/28143 | 9/1996 |
| WO | WO/0028989 | 5/2000 |
| WO | WO 0028989 A1 * | 5/2000 |
| WO | WO/0043044 | 7/2000 |
| WO | WO 0043044 A1 * | 7/2000 |

* cited by examiner

*Primary Examiner* — Michael G Hartley
*Assistant Examiner* — Micah-Paul Young
(74) *Attorney, Agent, or Firm* — Rick Matos; Innovar, L.L.C.

(57) ABSTRACT

Pharmaceutical form containing at least an active compound and a polymeric matrix, wherein said polymeric matrix comprises at least one polymer of cationic nature and at least one biodegradable polymer, process for the preparation thereof, pharmaceutical formulations comprising said pharmaceutical form, and their uses. The pharmaceutical form provides enhanced absorption of active compounds across the mucosa.

40 Claims, 33 Drawing Sheets

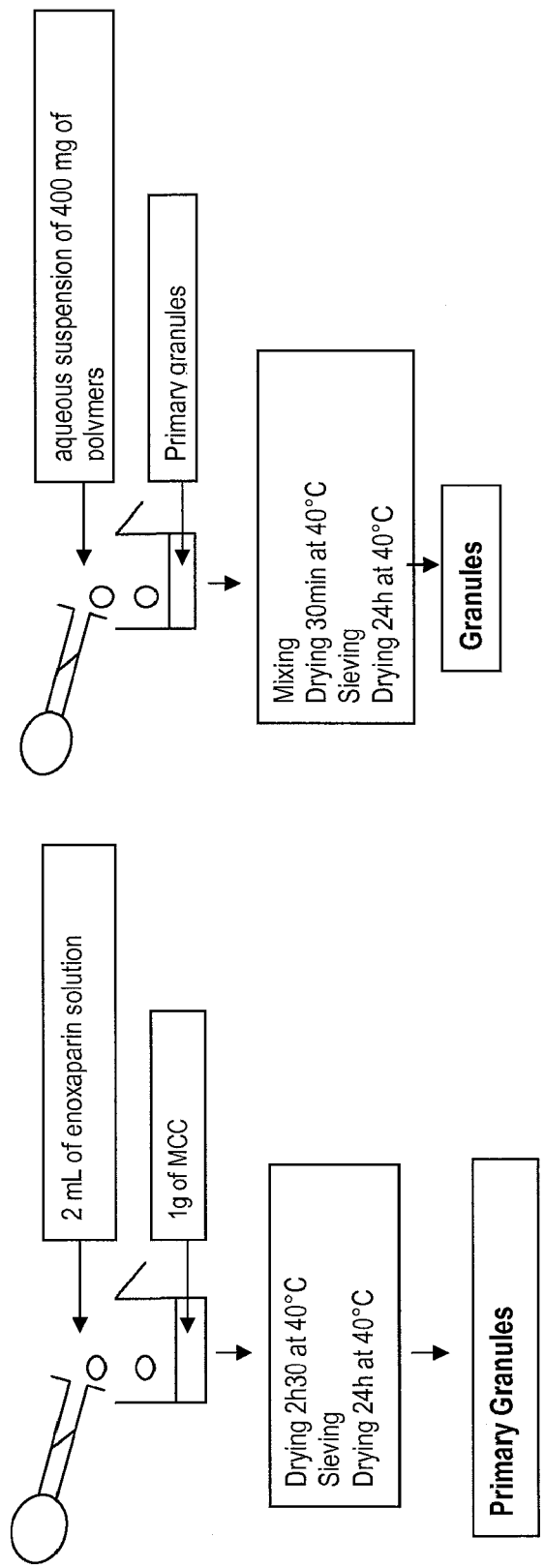

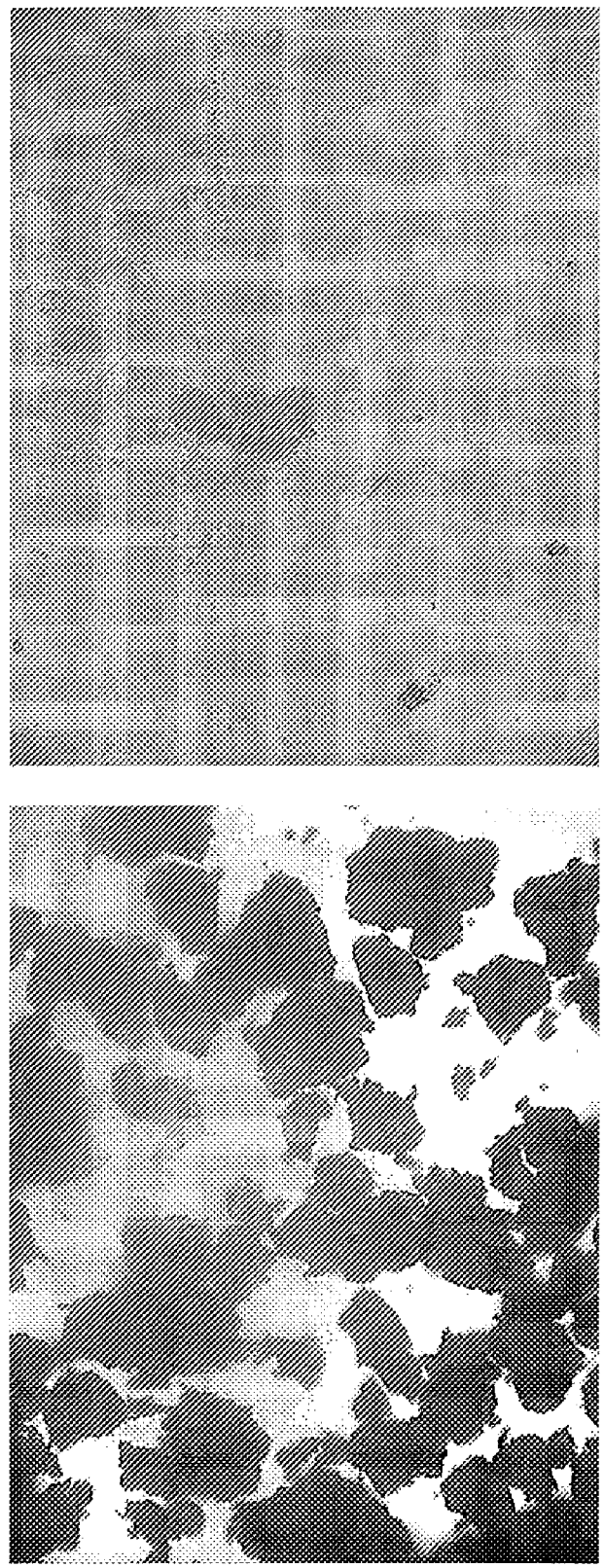

FIG. 9A
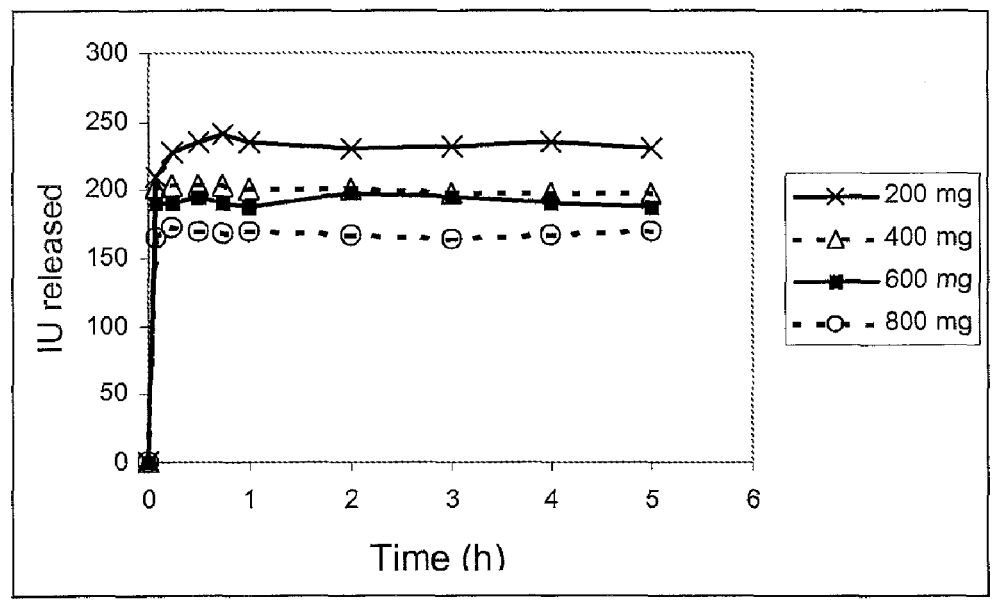
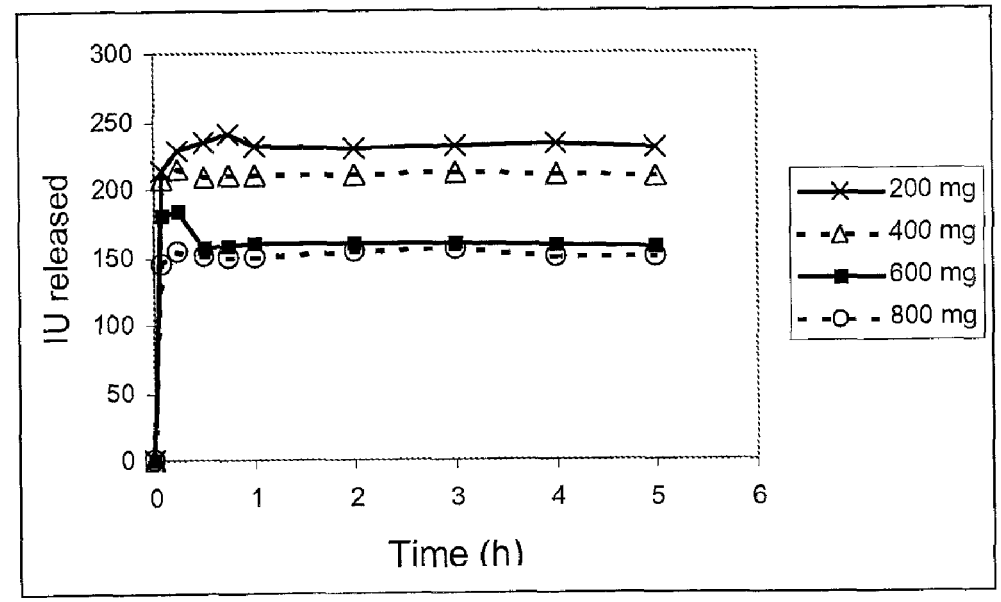
FIG. 9B

FIG. 13A
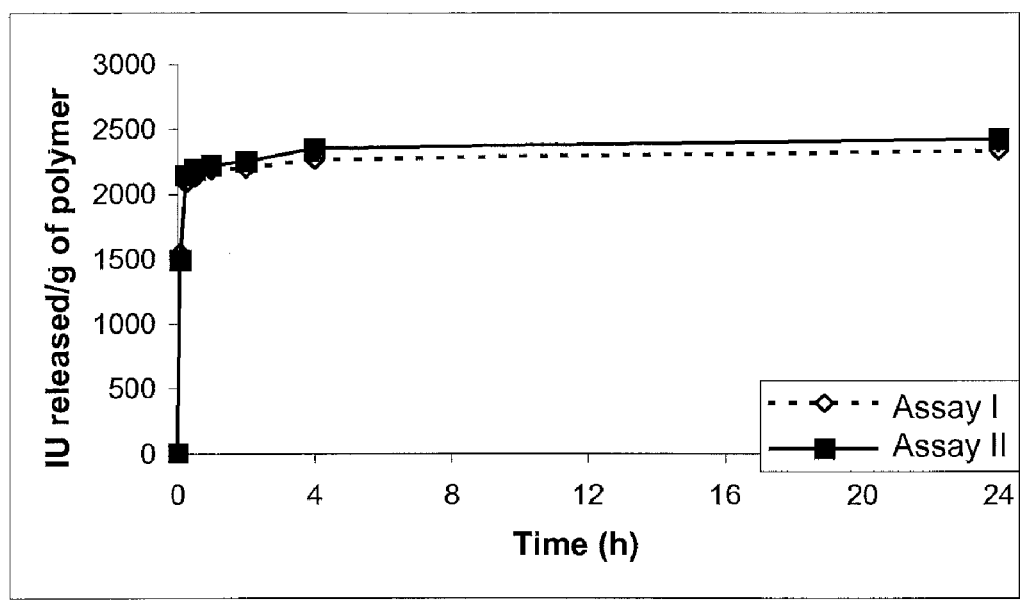
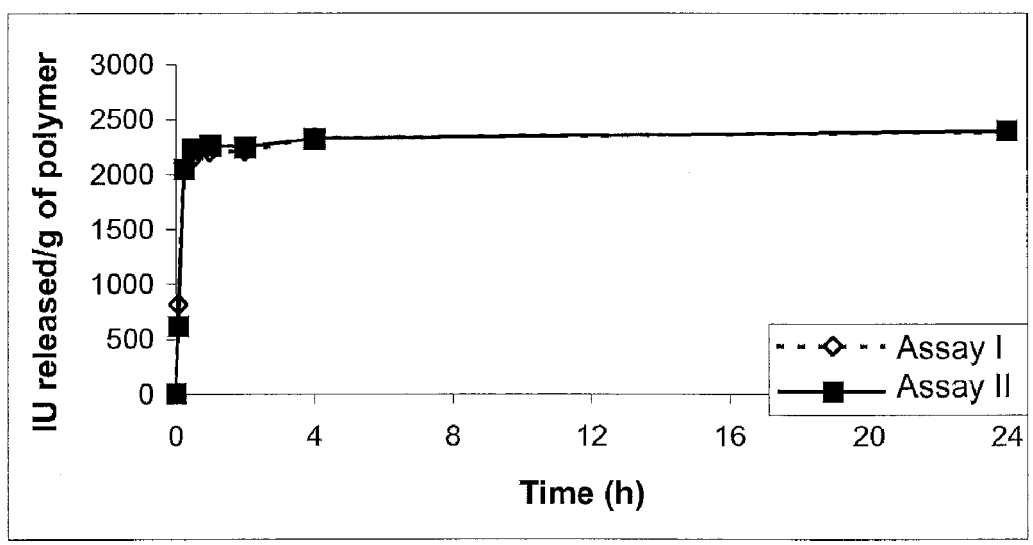
FIG. 13B

PHARMACEUTICAL DOSAGE FORMS FOR THE RELEASE OF ACTIVE COMPOUNDS

CROSS-REFERENCE TO EARLIER-FILED APPLICATIONS

The present invention claims the benefit of and is a divisional of U.S. application Ser. No. 12/779,556 filed May 13, 2010, which claims the benefit of and is continuation-in-part of PCT International Patent Application No. PCT/EP2008/065499, filed Nov. 13, 2008, which claims the benefit of European Application No. 07380319.9, filed Nov. 14, 2007, and U.S. application Ser. No. 12/779,556 filed May 13, 2010 also claims the benefit of and is a continuation-in-part of U.S. application Ser. No. 10/332,351, filed Jan. 8, 2003, which claims the benefit of PCT International Patent Application No. PCT/FR01/02159, filed Jul. 5, 2001, which claims the benefit of French Application No. FR 00/08902, filed Jul. 7, 2000, the entire disclosures of which are hereby incorporated by reference.

FIELD OF THE INVENTION

The present invention relates to pharmaceutical dosage forms for releasing active compounds and for increasing their mucosal absorption following administration, as well as to a process for preparing them, to pharmaceutical formulations containing said pharmaceutical dosage forms and to the use of said pharmaceutical dosage forms and said formulations for the manufacture of a medicament applicable to mucosa.

BACKGROUND OF THE INVENTION

A problem which has been posed in recent years in the pharmaceutical sector is that there is a great variety of active compounds which are characterized fundamentally, in that they cannot be administered by oral route. The main causes why these compounds cannot be administered by this route are: a) rapid enzymatic and metabolic degradation; b) chemical and biological instability; c) low solubility in aqueous medium; and/or d) limited permeability in the gastrointestinal tract.

Examples of such active compounds include: a) Peptidic-type (peptide) macromolecules such as insulin, interferons or calcitonins; b) Saccharidic-type (saccharide) macromolecules such as heparin or, heparins and derivatives such as LMWH (Low Molecular Weight Heparins), pentasacharides; and c) other types of smaller hydrophilic molecules such as salbutamol or acyclovir.

Heparins are anticoagulants which act by the inactivation of certain coagulation cascade factors. Heparins are essentially used for their anticoagulant (related with the inhibition of factor IIa) and antithrombotic (by the inhibition of factor Xa) properties for the prevention and the treatment of thromboembolic diseases (Low- and ultra-low-molecular-weight heparins. *Best Pract. Res. Clin. Haematol.* 2004; 17: 77-87). In prevention, they are used to reduce the incidence of thromboembolic complications after prolonged immobilization due to a disease, and after surgical interventions (Prevention of venous thromboembolism. Agnelli and Sonaglia., *Thromb Res.* 2000, 97: V49-62), and in curing, they are used for the treatment of deep vein thrombosis (Treatment of venous thromboembolism. Ageno. *Thromb Res.* 2000, 97: V63-72.), of pulmonary embolisms, of disseminated intravascular coagulation, acute arterial obstruction and the acute phase of myocardial infarction.

Currently, heparin is extracted from porcine or bovine intestinal mucosa (Heparins: all a nephrologist should know. Hetzel et al. *Nephrol Dial Transplant.* 2005; 20: 2036-42). The unfractionated heparin is a heterogeneous mixture of sulfated mucopolysaccharide chains whose molecular mass is between 3,000 and 30,000 daltons. Its average molecular mass is 15,000 Daltons, and it corresponds to a heparin molecule of around 45 osidic units (*Molecular weight dependency of the heparin potentiated inhibition of thrombin and activated factor X. Effect of heparin neutralization in plasma.* Andersson et al. *Thromb Res.* 1979; 15: 531-41).

Heparin acts by the intermediation of a cofactor: antithrombin III (ATIII), which is a natural plasma inhibitor of coagulation (Heparin and Low-Molecular-Weight Heparin: The Seventh ACCP Conference on Antithrombotic and Thrombolytic Therapy. Hirsh and Raschke. *Chest.* 2004; 126: 188S-203S) and it behaves as a catalyst with respect to ATIII. ATIII has a slow and progressive action. Once the heparin has been fixed to the ATIII by the intermediation of the pentasaccharide fragment, this action becomes immediate. This fixation causes a change in the formation of the ATIII which then permits the irreversible fixation thereof on the active site of serine proteinase-type coagulation factors (factors IIa, Xa and IXa, mainly). Then, heparin is released intact, and can then react with a new antithrombin molecule.

It should be mentioned that the pharmacodynamic effect of heparins depends on the chain length of oligosaccharides. Indeed, to inhibit the thrombin, heparin should be fixed on ATIII and on thrombin through a pentasaccharide block. On the other hand, to inhibit factor Xa, heparin should only fix to ATIII by the pentasaccharide block. Thus, the fragments with a molecular mass (MM) below 5,400 Da, i.e. 18 saccharide units, lose their capacity to be simultaneously fixed to thrombin and ATIII, and will thus have an essentially anti-Xa activity. The fragments with a MM greater than or equal to 5,400 Da will be both anti-Xa and anti-IIa. Standard heparin comprises fragments with a variable molecular mass of 2,000 to 30,000 Da, and therefore has activity on the two factors, Xa and IIa (Heparin and Low-Molecular-Weight Heparin: The Seventh ACCP Conference on Antithrombotic and Thrombolytic Therapy. Hirsh and Raschke. *Chest.* 2004; 126: 188S-203S). It therefore has both an antithrombotic and an anticoagulant activity, in comparison with low molecular weight heparins, which are essentially antithrombotic agents with a predominance of anti-Xa activity.

Venous thromboembolic disease continues to be responsible for important morbidity and/or mortality. In fact, in the United States, the number of persons hospitalized for this reason is estimated at between 300,000 and 600,000 per year. Furthermore, this disease, due to the pulmonary embolism of which it is the cause, would be responsible for 50,000 (Development of oral heparin therapy for prophylaxis and treatment of deep venous thrombosis. Money and Gorka. *Caridovasc Surg.* 2001; 9: 211-8) to 100,000 deaths per year in the United States (Prevention of venous thromboembolism. Agnelli and Sonaglia. *Thromb Res.* 2000, 97: V49-62).

Additionally, pulmonary embolism can be produced without clinical venous thrombosis, henceforth the interest in prevention with regard to patients with a risk of thrombosis, among which are: cancer, age over 70, prolonged immobility, paralysis, obesity or even taking estrogens by oral route.

Since heparin acts on the coagulation factors by a catalysis mechanism mediated by ATIII, the measurement of its plasma concentration does not constitute an efficient means to determine its biological activity. The procedures used should instead reflect heparin's capacity to inhibit factors Xa and IIa. For this reason, different measurement process can be used in human beings and animals: a) the measurement of the coagulation factor activity, expressed in units of inhibition of Xa or IIa activity; b) the measurement of the haemorrhaging time determined by the activated partial thromboplastin time (aPTT) (This test explores the intrinsic route of the coagulation measuring the coagulation time of decalcified and platelet-impoverished plasma in the presence of a platelet equivalent (cephalin) and calcium.); and c) the measurement of the prothrombin time exploring the intrinsic coagulation route (This procedure uses recalcified blood plasma in the presence of tissue thromboplastin; Digestive absorption of heparin with alternative formulations. Ubrich et al., 2002. S.T.P. *Pharma Sciences*. 2002; 12: 147-55). There is another process which only exists in animals, and consists of measuring the variation in the size of a thrombus. This does not permit quantifying the response, but it shows if there is a proven pharmacological action of the anticoagulant.

Insulin is the "anabolic" hormone par excellence; i.e. it permits providing the cells with the sufficient supply of glucose for the synthesis process with energy expenditure, which will then, through glycolysis and cell respiration, produce the necessary energy in the form of ATP (adenosine triphosphate mononucleotide) which uses the metabolism as unit of transportable energy for said processes. It maintains the glucose concentration in our blood. It achieves this because when the glucose level is high the pancreas releases it into the blood. Its function is to favor the cell absorption of glucose.

It is one of the two hormones produced by the pancreas together with glucagon (unlike insulin, when the glucose level decreases it is released into the blood). Insulin is produced in the pancreas in the "Islets of Langerhans", by cells called Beta cells. One way of detecting if the Beta cells produce insulin is by carrying out a test, checking for the presence of C-peptide in the blood. C-peptide is released into the blood when the Beta cells process the proinsulin, converting it into insulin. Only when between 10% and 20% of the Beta cells are in good condition, symptoms of diabetes begin to appear, first passing through a prior state called honeymoon where the pancreas still secretes some insulin.

Normally, the insulins currently used are synthesized by means of genetic engineering through recombinant DNA technology, due to the fact that a rapid, medium or slow activity is pursued. In type I diabetes, and in some cases of type II, it is necessary to inject insulin to maintain a correct glucose level in the blood. The following types of insulins exist: a) quick-acting insulins; b) intermediate-acting insulins or NPH; c) slow-acting insulins; and d) 24-hour insulins.

Insulin types can also be categorized by the site of administration: a) injectable subcutaneous insulin formulations, which include any insulin, whether quick-acting or delayed; b) injectable endovenous insulins formulations, which include: only quick-acting insulins that do not have retarders; c) inhalable insulin formulations, which despite being as efficient as the traditional one, eliminates the need of being injected to the patient. However, there is no insulin formulation on the market that can be administered by orally to provide sufficiently high bioabsorption, thereby highlighting the need for an oral solid formulation.

Although some of these compounds can be administered orally, they have very low and/or very erratic gastrointestinal absorption, which poses a serious problem for marketing these type of drugs, because the results obtained differ greatly from those expected due to their behavior in LADME (Liberation, Absorption, Distribution, Metabolism and Elimination) pharmacokinetic processes. Furthermore, these macromolecules are hydrophilic and very poorly permeable across the mucosa, which results in low mucosal absorption, in the case of the oral route. This is worsened since these macromolecules have to pass through the stomach.

The digestive mucosa allows small lipophilic molecules to pass through, but it is very impermeable to charged hydrophilic macromolecules. Furthermore, the digestive tract is coated with negatively charged mucosa, which has a natural tendency to repel the molecules of the same charge.

A clear example of an active compound whose absorption is limited following oral administration is heparin. After oral administration, absorption through the digestive mucosa is not limited by its solubility but by its low permeability with respect to the intestinal membrane, mainly due to its negative charge. The permeability of heparins through the digestive epithelium is, therefore, very low, which makes the administration of heparin/formulations containing heparin by oral route very difficult.

For this reason, the route of administration chosen in the majority of the aforementioned classes of compounds is parenteral administration, mainly via intramuscular or subcutaneous injections. At present, some of these compounds are even administered via nasal and pulmonary formulations as in the case of salmon calcitonin or insulin (Alpar, H. J.; Somavarapu, S.; Atuah, K. N.; Bramwell, V. W. *Adv. Drug Deliv. Rev.* 2005, 57, 411-430; Paltz, R. M.; Patton, J. S.; Foster, L.; Mohammed, E. USA Appl. No 355578).

Nevertheless, a problem posed by non-oral routes of administration is that, in most cases, these treatments require long periods of therapy such as, for example, in some types of diabetes, for which treatment is needed for the entire life, the frequency of administration being daily. Non-oral administration is a great disadvantage mainly for the patient, and for this reason, it is important to look for alternative routes of administration.

Fundamentally, the oral route, which is the most convenient for the patient and the most economical, is preferred; however, for these types of molecules (mainly for oligosaccharides and proteins), designing formulations prepared to be administered by oral route entails a problem and involves many complications, since the gastrointestinal tract degrades these active compounds. This means that they should be formulated to enable, first, the pharmaceutical form to pass through the stomach without degrading the active compound, and once it reaches the optimum absorption mucosa, release a large quantity of this active compound selectively on the mucosa wall in a relatively short time interval. By doing so, the desired therapeutic or preventive activity is obtained.

In recent decades, numerous vehicles have been developed or designed to increase the systemic bioavailability after mucosal administration of numerous traditionally poorly absorbable active compounds, among which we highlight protein compounds, such as insulin (Norovirus capsid protein expressed in yeast forms virus-like particles and stimulates systemic and mucosal immunity in mice following an oral administration of raw yeast extracts. Xia et al. *Journal of Medical Virology* (2006), Volume Date 2007, 79(1), 74-83; Delivery systems and adjuvants for oral vaccines. *Opinion on Drug Delivery* (2006), 3(6), 747-762; Gastrointestinal absorption of heparin by lipidization or coadministration with penetration enhancers. Ross et al. *Current Drug Delivery* (2005), 2(3), 277-287); antigens (Gastrointestinal absorption of heparin by lipidization or coadministration with penetration enhancers. Ross, Benjamin et al. *Current Drug Delivery* (2005), 2(3), 277-28; Oral heparin: status review. Arbi et al. *Thrombosis Journal* (2006)) and antibodies, as well as polysaccharides such as unfractionated heparins and low molecular weight heparins (Ximelagatran. Choudhury et al. *Drugs of Today* (2006), 42(1), 3-19).

The following are examples of technologies developed to provide vehicles designed to increase systemic bioavailability after the mucosal administration of numerous active compounds which are traditionally poorly absorbable:

Design of prodrugs (Prodrug strategies to enhance the intestinal absorption of peptides. Gangwar et al. *Drug Discovery Today* (1997), 2(4), 148-155.)

Use of enzyme metabolism inhibitors (Pharmacokinetic enhancement of protease inhibitor therapy. King et al. *Clinical Pharmacokinetics* (2004), 43(5), 291-310).

Development of absorption promoters (Patent EP1652836; patent IS 200602146).

Development of mucoadhesive devices such as bioadhesive systems or intestinal patches (Oral delivery of macromolecules using intestinal patches: applications for insulin delivery. *Journal of Controlled Release* (2004), 98(1), 37-45).

Development of particulate systems

Bioadhesive systems are structures of relatively large size which adhere to the intestinal mucosa after oral administration, thereby significantly increasing the time of intestinal transit of the formulation. Likewise, these devices avoid, to a large extent, the need for the active compound to diffuse through the luminal environment or even through the mucosa coating the absorption epithelium. An example of these systems is the development of bioadhesive patches, developed for the first time for the systemic absorption of active compounds in the intestine by Eaimtrakarn et al. (Retention and transit of intestinal mucoadhesive films in the rat small intestine. Eaimtrakarn et al. *International Journal of Pharmaceutics* (2001), 224, 61-67) which consists of a four-layered device: (I) a film of coating formed by a water-insoluble polymer which protects the protein active principles from luminal degradation, (II) a surface constituted by a polymer sensitive to the intestinal pH, (III) an intermediate film carrying the active compound and (IV) a bioadhesive film positioned between the intermediate film and the surface coatings designed to generate a high concentration gradient between the patch and the intestine enterocytes. However, these devices are affected by physiological processes of cell and mucosal turnover in the absorption epithelium. It is for this reason that the use of these devices has not yet managed to avoid the serious problem of variability between administrations, both in relation to the place of adhesion and the contact time of the formulation with the absorption membrane.

To summarize the above, current research in pharmacology (based on particulate systems) is focused on two different but complementary areas: targeting and controlled release systems.

The release profile of the active compound depends on numerous parameters: size, distribution, porosity, degradation, permeability of the polymer, etc.

The administration of a free drug by oral, intravenous route, etc., normally gives rise to a systemic distribution of the active compound, when what is affected is only a tissue, a local area or a type of cell. From this perspective, it would make much more sense to achieve a targeted action of the drug, especially for those compounds with high toxicity (such as anti-carcinogenic) or for those with a low therapeutic index. For example, administration through these particulate release systems involves an improvement in the administration of the anesthetic agents, reducing the necessary number of doses, avoiding systemic toxic effects and increasing its concentration in the desired site (Le Corre, P., Rytting, J. H., Gajan, V., Chevanne, F., Le Verge, R., *J. Microencapsulation*, 14 (1997) 243 Blanco, M. D., Bernardo, M. V., Gómez, C., Muñiz, E., Teijón, J. M., *Biomaterials*, 20 (1999) 1919.; Estebe, J. P., Le Corre, P, Chevanne, F., Malljdant, Y., Le Verge, R., *Anesth. Analg.* 81 (1995) 99).

As to controlled release systems, particulate vectors are formed by polymeric elements which control the release and/or absorption of the active compound through different mechanisms, within which the most typical are the diffusion of the active compound through the pores or channels formed in the polymeric matrix and the degradation/erosion of the polymeric material.

U.S. Pat. No. 6,475,493 discloses formulations that provide a controlled release in acidic media and quick/rapid release in basic media. The formulations employ cores with aqueous coatings which comprise, in heterogeneous mixture: a) at least one water insoluble polymer in a proportion of 75% by weight of the coating; b) an enteric water soluble polymer at pH higher than 6.0 in a proportion of 1-25% by weight of the coating; and c) a water-soluble polymer.

The heterogeneous degradation of the polymeric material occurs on the surface of the material which is in contact with the physiological medium. In this case, the rate of degradation is constant and the undegraded material maintains its chemical integrity during the process. Logically, those materials with high surface/volume ratio will degrade faster than the equivalents with a smaller ratio.

Homogeneous degradation involves a random deterioration throughout a polymeric mass. Whilst the molecular weight of the polymer continually decreases, the material can maintain its original shape and retain mass until the polymer has undergone a considerable degradation (even more than 90%), and reaches a critical molecular weight; at that time the solubilization and loss of mass starts (Sáez et al. *Liberación Controlada de Fármacos. Revista Iberoamericana de Polímeros.* Vol 5(1). 2004).

U.S. Publication 2005/0020539 A1 discloses pharmaceutical compositions, and methods of preparation thereof, for the oral administration of heparin for its selective release in the intestine. The compositions comprises a structure of multiple matrices which comprises: a) an internal matrix of amphiphilic compounds and lipophilic compounds wherein the active compound is at least partially embedded; and b) an outer hydrophilic matrix within which the internal matrix is dispersed.

For drug-containing particles to have the desired activity, homogenous degradation throughout the polymeric mass is preferred in order to achieve a suitable release. Also, a suitable surface potential should be favored so that the particles approximate the absorption mucosa. Currently the effort of large multinational companies in the pharmaceutical sector is focused on the development of colloidal systems with reduced particle size, as a strategy to increase the systemic bioavailability of active compounds.

It is very well known in scientific literature and in the patent state of the art, how reduced particle size significantly increases the dispersion of the active compound on a large luminal surface, favoring a controlled release of the drug (Potential of poliester microparticles for the sustained release of oral vaccine. Benoit, M. et al. *Biopharmaceutics and Pharmaceutical Technology,* 1*st, Budapest,* May 9-11, 1995 (1995), 431-2), decreasing the local concentrations of active compound and enabling high mucoadhesion (Preparation of thiomer microparticles and in vitro evaluation of parameters influencing their mucoadhesive properties. Albrecht, K.; et al. *Drug Development and Industrial Pharmacy* (2006), 32(10), 1149-1157), as well as the systemic passage of whole particles (Intestinal absorption of PLGA microspheres in the rat. Damge, C. et al. *Journal of Anatomy* (1996), 189(3), 491-501) which release the active compound in a controlled manner.

Studies carried out by numerous authors reveal the potential shown by these devices for improving intestinal absorption of poorly absorbable molecules, as well as showing the importance of small particle size in intestinal absorption (Transmucosal macromolecular drug delivery. Prego, C. et al. *Department Journal of Controlled Release* (2005), 101(1-3), 151-162; Gastrointestinal uptake of biodegradable microparticles: effect of particle size. Desai et al. *Pharmaceutical Research* (1996), 13(12), 1838-1845).

These colloidal systems include microparticles (Polymeric nano- and microparticle technologies for oral gene delivery, Bhavsar et al. *Expert Opinion on Drug Delivery* (2007), 4(3), 197-213); nanoparticles (Lectin-modified solid lipid nanoparticles as carriers for oral administration of insulin, Hang et al. *International Journal of Pharmaceutics* (2006), 327(1-2), 153-159); formation of complexes (Stable pharmaceutical formulations comprising macromolecular carriers and methods of use thereof, Tan et al. WO2007021970) and liposomes (Investigation of lectin-modified insulin liposomes as carriers for oral administration, Zhang et al. *International Journal of Pharmaceutics* (2005), 294(1-2), 247-259) among others.

Microparticles are spherical or non-spherical particles, preferred having a diameter below 125 µm. This group includes microcapsules, which are defined as vesicular systems wherein the drug is confined to a cavity surrounded by a single membrane (typically polymeric); and microspheres, which are matrix-based systems in the form of spherical particles with a size between one and several dozens of microns, without distinction between coating and core, wherein the drug is dissolved or dispersed within the matrix formed by support materials, generally biocompatible polymers and with a large spectrum of release rates and degradative properties (Torrado, J. J., Cadórniga, R., Vectorización, *CIF,* 8 (1989a) 242). The drug is released through various mechanisms, such as surface erosion, the degradation/dissolution of the matrix materials, diffusion, and a combination of diffusion and erosion or erosion and degradation (Torrado, J. J., Cadórniga, R., *Farm. Clin.,* 6 (1989b) 724).

Nanoparticles are submicronic particulate systems (<1 µm). Depending on the process used to prepare nanoparticles, nanocapsules or nanospheres can be obtained, these being the morphological equivalents of microcapsules and microspheres, respectively (Rollot, J. M., Couvreur, P., Roblot-Treupel, L., Puisieux, F., *J. Pharm. Sci,* 75 (1986). 361-364).

An article (Oral bioavailability of a low molecular weight heparin using a polymeric delivery system, *Journal of Controlled Release* 2006, 113, 38) describes nanoparticles formed by a technique of multiple emulsion and evaporation of solvent, which nanoparticles contain a dispersion of tinzaparin in a polymeric matrix of poly(ε-caprolactone) and Eudragit® RS and contains polyvinyl alcohol as surfactant.

Another article (Microencapsulation of Low Molecular Weight heparin into Polymeric Particles Designed with Biodegradable and Nonbiodegradable Polycationic Polymers, *Drug Delivery* 2003, 10, 1) describes microparticles formed by the method of water/oil/water emulsion and evaporation of solvent, which contain low molecular weight heparin, biodegradable polymers such as poly(ε-caprolactone) or poly(D, L-lactic acid-co-glycolic acid) and nonbiodegradable polycationic polymers such as Eudragit® RS or Eudragit® RL) or Eudragit® RS: poly(ε-caprolactone) combinations; Eudragit® RS: poly(D,L-lactic acid-co-glycolic acid); Eudragit® RS: Eudragit® RL: poly(D,L-lactic acid-co-glycolic acid) (PLGA) wherein the polymers are present in equal proportion. Due to the hydrophilic nature of the active substance (low molecular weight heparin (LMWH)) an important diffusion of the active substance is induced through the continuous aqueous phase during the emulsification and solidification procedure. For this reason, the resulting particles have a variable distribution of the active substance through the particle, always having, in a greater or lesser proportion, active substance on the surface. Taking into consideration that they are small-sized particles which have a high specific contact surface with the gastric acids and enzymes, this aspect means that part of the active compound is lost in its passage through the stomach. Furthermore, microparticulate systems, which intrinsically bear a low content of active substance, have a lower encapsulation yield than particles of larger size. Therefore, the amount of active substance they can incorporate is small.

U.S. Publication 2005/0013866 A1 (whose inventors are co-authors of the article mentioned in the previous paragraph) discloses nanoparticles and microparticles for the oral administration of heparins, peptides and proteins, nucleic acids and growth hormone, formed from a polymeric matrix which comprises at least one biodegradable polymer with at least one polycationic polymer. The biodegradable polymer may be selected from polyesters, poly-ε-caprolactone, polyanhydrides, polyamides, polyurethanes, polyacetals, polyorthoesters and natural polymers and the polycationic polymer may be selected from cellulose derivatives, copolymers of acrylic and methacrylic acid esters such as trimethylammonioethyl methacrylate chloride, chitosan and derivatives and polylysine. The particles are obtained by formation of a water/oil/water emulsion.

The great advantage of these micro- and nanoparticulate systems compared with alternative solutions such as implants is that, due to their small size, they can be injected with a conventional syringe, not requiring surgical intervention. On the other hand, and although it seems paradoxical, it may be easier for a microsphere to be introduced in a cell than for the free drug, since a nanoparticle or microparticle of suitable size is easily incorporated as a vacuole through phagocytosis.

These systems are very interesting as drug carriers which cannot be reproducibly or reliable administered orally, for drugs such as protein, peptide, hormone or enzyme drugs which are the product of the biotechnological revolution, and are easily degraded by the gastrointestinal tract enzymes. Furthermore, polymeric microparticulate systems incorporating anti-carcinogens have been described and clinically tested (Wood, R. W., Li, V. H. K., Kreuter, J., Robinson, J. R., *Int. J. Pharm.,* 23 (1985) 175); immunosuppressants (Yoshikawa, H., Nakao, Y., Takada, K., Muranishi, S., Wada, R. T., Tabata, Y., Hyon, S. H., Ikada, Y., *Chem. Pharm. Bull.,* 37 (1989) 802.); vitamins (Sánchez, A., Vila-Jato, J. L., Alonso, M. J., *Int. J. Pharm.,* 99 (1993) 263); antibiotics, antibacterial agents (Sánchez, A., Vila-Jato, J. L., Alonso, M. J., *Int. J. Pharm.,* 99 (1993) 263); anti-inflammatory agents (Dubemet, C., Benoit, J. P., Couarraze, G., Duchéne, D., *Int. J. Pharm.,* 35 (1987) 145.) and vaccines (Eldrige, J. H., Staas, J. K., Meulbrock, J. A., McGhee, J. R., Tice, T. R., Gilley, R. M., *Mol. Immunol.,* 28 (1991) 287) with very good results.

Among all of them, nanoparticles (particulate vectors with a diameter below 1 µm) have shown the greatest potential mainly due to the advantages conferred by their reduced size (Nanoencapsulation. II. Biomedical applications and current status of peptide and protein nanoparticulate delivery systems. Reis et al. *Nanomedicine* (2006), 2(2), 53-65). These devices may be prepared using polymers such as albumin, ethyl cellulose, gelatin, casein, polyesters, polyanhydrides, polyalkylcyanoacrylates and natural polymers among others (Polymeric nano- and microparticle technologies for oral gene delivery. Bhavsar et al, *Expert Opinion on Drug Delivery* (2007), 4(3), 197-213; Starch microparticles as vaccine adjuvant. Rydell et al. *Expert Opinion on Drug Delivery* (2005), 2(5), 807-828) through procedures such as solvent evaporation/extraction (Polymeric nano- and microparticle technologies for oral gene delivery. Bhavsar et al. *Expert Opinion on Drug Delivery* (2007), 4(3), 197-213); interfacial polymerization; simple coacervation (Polymeric coacervate microparticles useful for the sustained release administration of therapeutic agents. Heller, Phillip F. WO2006023207; Encapsulation of adenoviral vectors into chitosan-bile salt microparticles for mucosal vaccination. Lameiro et al. *Journal of Biotechnology* (2006), 126(2), 152-162), complex coacervation (Chitosan: An Atractive biocompatible polymer for macroencasulation. .C. Peniche et al. *Macromolecules Bioscience*, (2003) 3, 511-520; Tramadol release from delivery system based on alginate-chitosan microcapsules. Acosta et al. *Macromolecules Bioscience*, (2003) 3, 546-551) and precipitation of supercritical fluids (Drug delivery applications of supercritical fluid technology. Sunkara et al. *Drug Delivery Technology* (2002), 2(1), 44, 46-50), among others.

The advantages conferred by the reduced particle size in the increase of absorption of poorly permeable molecules through the mucosal barrier can be found in numerous publications in the scientific literature (Mucoadhesive nanoparticulate systems for peptide drug delivery. Takeuchi et al. *Advanced Drug Delivery Reviews* (2001), 47, 39-54; Enteral absorption of insulin in rats from mucoadhesive chitosan-coated liposomes. Takeuchi et al. *Pharmaceutical Research* (1996), 13, 896-901).

The research carried out by Morishita et al. (Mucosal insulin delivery systems based on complexation polymer hydrogels: effect of particle size on insulin enteral absorption. Morishita et al. *Journal of Controlled Release* (2004), 97, 115-124) clearly shows the degree in which the reduction in particle size increases systemic bioavailability of insulin when the formulations are administered intestinally. According to published observations by these authors, a reduction in particle size from 180-230 µm to <43 µm produces a 18 fold increase in the bioavailability not the insulin administered, going from a systemic bioavailability (relative to the subcutaneous route) of 0.7% to 12.8%.

However, these smaller size particulate systems have a series of drawbacks. For microspheres, the main obstacle to achieving effective parenteral systems is the degradation and subsequent non-specific elimination by the reticuloendothelial systems, despite the fact that attempts have been made to modify these systems appropriately (Davis, S. S., Illum, L., Colloidal delivery systems-Opportunities and challenges. *Site-Specific Drug Delivery*, E. Tomlinson, (S. S. Davis (Eds), pp. 93-110 (1986), John Wiley & Sons Ltd.; UK). This aspect worsens in the case of oral route administration, since in this case it has been verified how degradation at stomach acid pH makes the active compound reach the site at which it should be absorbed in very small quantities, causing up to 90% losses in in vitro activity.

For polymeric conjugate transport systems, their low solubility usually causes problems in their preparation (Duncan, R., Kopekova-Rejmanova, P., Strohalm, J., Hume, I., Cable, H. C., Pohl, J., Lloyd, B., Kopecek, J., Br. *J. Cancer*, 55 (1987) 165-174.; Endo, N., Umemoto, N., Kato, Y., Takeda, Y., Hara, T., *J. Immunol. Methods*, 104 (1987) 253-258) and in their injection into the blood stream (Zunino, F., Pratesi, G., Micheloni, A., *J. Control. Rel.*, 10 (1989) 65-73).

Other forms of release of active compounds are micelles which, although they are one of the least studied systems, they base their activity on physicochemical characteristics, especially in organic solvents (Chu, B., *Langmuir*, 11 (1995) 414-421). Currently, there are water-soluble micelles related to the chemistry of amphiphilic polymers, which are biocompatible and biodegradable. However, these formulations have limitations with regards to the stability of the active compound to be released.

Homar et al (*J Microencap* 2007, 24:7, 621-633) have studied the influence of polymers on the bioavailability of microencapsulated celecoxib. Microparticles with a size range of 11-34 micrometers were prepared using an emulsion method followed by solvent evaporation. Relative bioavailability of celecoxib was below 20% in all cases.

On the other hand, the use of technologies linked to the production of nanoparticles and microparticles is currently limited by a considerable number of factors which limit the subsequent clinical and industrial development thereof. Among the factors which limit the use of these technologies are: a) complex preparation processes; b) problematic scale-up (Microspheres for controlled release drug delivery. Varde, et al. *Expert Opinion on Biological Therapy* (2004), 4(1), 35-51); c) limitations in medium and long-term stability (Strategic approaches for overcoming peptide and protein instability within biodegradable nano- and microparticles. Bilati et al. *European Journal of Pharmaceutics and Biopharmaceutics* (2005), 59(3), 375-388); d) high development and production costs; e) low bioavailability of the pharmaceutical active with these types of systems (particle size lower than 100 µm; see Issues in oral nanoparticle drug carrier uptake and targeting. Florence, Alexander T. *Journal of Drug Targeting* (2004), 12(2), 65-70); the best results being obtained in the administration of molecules with immunological properties wherein the nanoparticles and the microparticles of smaller size have intrinsic activity as antigenic adjuvants; see Potential of polymer microencapsulation technology for vaccine innovation. Morris et al. *Vaccine* (1994), 12(1), 5-11; Particulate systems as adjuvants and carriers for peptide and protein antigens. Liang et al *Current Drug Delivery* (2006), 3(4), 379-388)).

Nanoparticle systems also have problems with low product yield and low encapsulation efficiency. The use of emulsions and/or interfaces in many of the devices based on microparticles and nanoparticles enables the release/migration of the drug substances to into the process liquids or media which will later be eliminated as part of the preparation process, thereby causing a very high loss of active compound. In the same way, the preparation processes can generate numerous losses of the matrix-forming material, of the matrix or of the particle coating. The loss of polymeric material in the filters used in the preparation of microparticles by evaporation/solvent extraction and losses by adhesion of matrix-forming material in the preparation of microparticles, for example as can occur with spray drying.

Nanoparticle systems also suffer from poor batch-to-batch reproducibility. The special sensitivity of colloidal systems to small variations in the particulate vector preparation conditions requires a strict control of all manufacturing variables, paying special attention to environmental factors (temperature, humidity, atmospheric pressure), variations in the excipients or starting materials as well as in the instruments used in their preparation. By way of example, a small increase in the preparation temperature favors the diffusion of the active compound incorporated in the internal phase of a w/o/w (water/oil/water) emulsion towards the external aqueous phase, thereby causing a great loss in active compound content. All these conditioning factors usually cause great batch-to-batch variations in particular in: a) the release profile of active compound from the nanoparticles; b) requirement of excessively broad product specifications; and c) residual solvent content.

Small variations in the preparation conditions or the starting materials may cause large variations in the active compound content of these formulations, thereby severely hindering the standardization of the process within acceptable limits. Likewise, variations in the active compound content as well as in the particle size of these formulations (fundamentally due to small variations in the stirring conditions and to environmental variations) cause changes in the release of the active compound from these vectors. Thus, an increase in particle size will delay the release of the active compound, modifying its pharmacokinetic profile after its administration and, therefore, its systemic bioavailability.

The batch-to-batch variability, due to the sensitivity of these systems to variations in the preparation conditions, forces establishment of very broad end product specifications in order to validate the production of a batch by a previously standardized industrial procedure. It may serve, for example, to establish specifications for parameters such as active compound content or the release of active compound in a determined time which, as previously indicated, have a large batch to batch variability.

The preparation of particulate systems by procedures such as interfacial polymerization and emulsification, with subsequent evaporation/solvent extraction, often requires the use of very high quantities of organic solvents, for which daily administration is limited based on the majority of the Pharmacopoeias existing at present. Despite the fact that the elimination of these solvents forms part of the preparation procedure of these vectors, the solvent avidity of some polymers typically used, the sensitivity of the particulate vectors to more efficient solvent elimination methods (such as, for example, lyophilization) and the reduced limits for the presence of some of the most commonly used solvents for the preparation of microparticles and nanoparticles (such as, for example, Dichloromethane, classified in the European and United States Pharmacopoeias as Class 2 solvent), may limit the clinical use of microparticles and nanoparticles.

Size-related toxicity of nanoparticles is also an issue. When particulate vectors are administered by mucosal routes, the active compound content therein may be released to the luminal environment by mechanisms already described herein, or the particulate vectors may fully cross the absorption membrane and subsequently release the active compound. In this regard, the particle size constitutes the most important parameter, since a reduction in particle size causes an exponential increase of the material in the form of particles which fully cross the mucosal barrier. In other words, the smaller the particle, the larger the relative proportion of mass of powder or colloid that is attributable to the excipients rather than the active (Gastrointestinal uptake of biodegradable microparticles: effect of particle size. Desai et al. *Pharmaceutical Research* (1996), 13(12), 1838-1845)). Unlike larger sized particulate vectors, as may be the case of granules and pellets prepared with polymers, the absorption of the microparticle-forming material and, especially of nanoparticles, requires consideration of the toxicological aspects related to the delivery of these materials to systemic circulation. Likewise, the consequences of the exposure of potentially antigenic materials on the immune response (such as, for example, proteins) in the form of microparticles and nanoparticles on organs, tissues or bodily compartments to which immunocompetent cells may access are known, it being possible to generate a wide range of immune responses ranging from the suppression of lymphocyte proliferation to the appearance of hypersensitivity reactions.

There are a high number of procedures for the preparation of systems in the form of microparticles and nanoparticles which are currently protected by patents. Likewise, the need to use high solvent quantities, high gas pressures, the establishment of sophisticated control methods of the manufacturing conditions, the high cost of the machinery used and the little presence of these formulations in the market are conditioning factors, known by a person skilled in the art, which raise production costs and condition the existence of facilities which have sufficient manufacturing flexibility to manufacture by contract formulations of this type, also worsened by the complexity in the scaling of the formulations of microparticles and nanoparticles developed in the laboratory.

All these factors have limited commercialization of nanoparticle-based products and highlight the need to develop vehicles which involve less aggressive manufacturing methods, which have improved stability properties and whose industrial scaling is possible or executable by procedures more commonly used in the pharmaceutical industry.

Despite the fact that the use of granules and pellets has been primarily for the oral administration of active compounds, the current state of the art demonstrates that no formulation constituted by them, nor any other derivative thereof such as capsules or tablets, has managed to give rise to significant absorptions of macromolecules whose systemic bioavailability after their non-parenteral administration is more limited by the reduced permeability in the absorption barrier of the molecule than due to the reduced solubility thereof in the luminal fluids.

U.S. Publication 2005/0281871 A1 discloses a spray coating method for coating granules or pellets wherein the mixture of coating components is performed during the spray process, by simultaneous spray of two aqueous dispersions containing the film forming agents separately, said agents being selected from: a) a (meth)acrylate $C_1$-$C_4$ alkyl ester or methacrylic acid in a 30-80% by weight and (meth)acrylate monomers bearing a tertiary amino group in the alkyl radical in 70-20% by weight; and b) a polymer bearing anionic groups selected from cellulose derivatives or (meth)acrylate copolymer. This overcomes problems related to the formation of dispersed mixtures by spray coating, such as aggregation or coagulation of components and the use of non ionic emulsifiers in 10% by weight and higher, which homogenize the dispersions but presents as a drawback an increase in active compound instability.

Therefore, it can be concluded that the latest advances in pharmaceutical technology of oral formulations containing active compounds of the types previously described herein, irrespective of the problems which may be associated to the industrial preparation process, are aimed at increasing the contact surface by adhesives or reducing particle size. These favor contact by increasing their specific surface to achieve significant absorptions of active compounds through the mucosal routes. Particulate systems of greater size are left to one side because the surface potential thereof cannot be calculated (which entails a problem since the surface charge of the particles cannot be calculated to be able to predict the approximation and non-repulsion thereof with the mucosal surface) nor can they be phagocyted (phagocytosis by cells) due to their greater size and to the difficulty of those particles with greater specific surface area to adhere to the mucosa while avoiding repulsion from the very same mucosa. The inventors have previously observed that when the pharmaceutical dosage forms of the prior art were used in greater size, the absorption decreased.

Considering the existent prior art discussed herein, it would not be expected that a person skilled in the art, would be inclined to develop systems of large particle size made through common and easily standardizable processes and to achieve significantly high systemic bioavailability of drugs for which the mucosa route has been traditionally inaccessible, by improving the release as well as the absorption of said drug(s). There remains, therefore, the need to provide new particulate systems for the administration of active compounds via mucosal route.

SUMMARY OF THE INVENTION

The inventors have now shown, surprisingly and unexpectedly with regard to the permeation of large molecules across the gastrointestinal barrier, that particulate vectors comprising a polymer matrix based on a mixture of nonenteric biodegradable polymer and on a nonenteric polycationic polymer allow the oral administration of amounts of active principles, especially of heparin, that are close to those conventionally used parenterally.

The pharmaceutical forms make it possible, unexpectedly, to obtain longer action than for the administration of a similar dose in solution administered intravenously, whereas it is known that the doses administered orally must often be very much higher than the doses administered intravenously in order to be able to exert their activity, on account of the losses of active principle incurred by their residence in the gastrointestinal tract (acidic pH of the stomach, enzymes, various secretions, first passage through the liver, etc.).

An object of the invention is provide particulate vectors for improving the oral absorption of active principles, the vectors being formed from a polymer matrix comprising at least one biodegradable polymer combined with at least one polycationic polymer.

An object of the invention is to provide a selective-release pharmaceutical form for delivery and subsequent absorption of relatively high quantities of poorly permeable active compounds, in particular, macromolecular active compounds, to mucosal tissue. The pharmaceutical form can be produced on an industrial scale, resolving the problem of the low homogeneity of batches existing in the case of micro and nanoparticles.

One of the purposes of the present invention has been to develop, through different studies, a solid form which possesses the advantages of larger particle sizes with regard to scaling and manufacturing, and of high membrane absorption for molecules traditionally recognized having reduced membrane permeability following oral administration.

In general, an object of the invention is to provide a pharmaceutical composition that promotes high mucosal absorption of generally poorly permeable hydrophilic macromolecules, such as those bearing negatively charged groups at pH greater than or equal to 4, that protects the hydrophilic macromolecule against an aggressive (acidic) luminal environment, and that promotes release of the hydrophilic macromolecule at a locale in the gastrointestinal tract that is ideal or optimum for its mucosal absorption.

It is another object of the invention to provide a pharmaceutical form with characteristics which permit the selective release of an active compound in proximity of or adjacent to mucosa (mucosal membrane or mucosal cellular wall).

Another object of the invention is to provide a pharmaceutical form having an average particle diameter in the range of 0.1 mm to 1 mm, or 0.1 mm to 1.2 mm, that provides reduced degradation of active compound in the stomach, maintains a high absorption of poorly permeable active compound across the mucosa, maintains high binding affinity of the pharmaceutical form for mucosa in order to provide improved absorption of active compound across the mucosa (e.g. oropharyngeal, gastrointestinal, pulmonary, nasal or vaginal), provides an immediate release of available active compound (thereby excluding an extended release formulation), provides a high loading capacity of active compound, and provides a high relative percentage of the total amount of active compound immediately released from the pharmaceutical form.

Some embodiments of the invention include those wherein: 1) less than 20% of the active compound is degraded in the gastric region following oral administration of the pharmaceutical form; 2) at least 60% of the active compound is released from the pharmaceutical form within 3 hours or less following administration; 3) the active compound comprises at least 20% by weight of the pharmaceutical form; 4) about 95% of the total amount of active compound present in the pharmaceutical form is available for immediate release.

Objects of the present invention are achieved by employing at least one polymer of cationic nature that forms a matrix, in a pharmaceutical form, that provides significantly high absorption of molecules whose systemic bioavailability is generally limited by the reduced permeability in the absorption barrier due to the reduced solubility of the molecules in the luminal fluids, in particular, for molecules for which the route of oral administration has generally been limited, such as, for example, glycosaminoglycans, highly sulfated glycosaminoglycans, such as unfractionated heparins, low molecular weight heparins, fondaparinux and/or proteins/peptides such as, for example, insulin.

An aspect of the invention provides a pharmaceutical form (pharmaceutical composition) comprising at least one pharmaceutically active compound and a polymeric matrix, wherein said polymeric matrix comprises at least one polymer of cationic nature.

Another aspect of the invention provides a process for preparing the aforementioned pharmaceutical form, the process comprises: combining at least one active compound and at least one polymer of cationic nature to form a polymeric matrix comprising the active compound and polymer.

Another aspect of the invention provides a pharmaceutical formulation for the administration of the previously described pharmaceutical form.

Another aspect of the invention provides the use of the aforementioned pharmaceutical form for preparing a pharmaceutical formulation (pharmaceutical dosage form).

Another aspect of the invention provides use of the aforementioned pharmaceutical form or pharmaceutical formulation, for the manufacture of a medicament applicable to a mucosa selected from oropharyngeal mucosa, gastrointestinal mucosa, pulmonary mucosa, nasal mucosa and vaginal mucosa.

Another aspect of the invention provides the use of the aforementioned pharmaceutical form or pharmaceutical formulation as a medicament applicable to a mucosa selected from the group formed by oropharyngeal mucosa, gastrointestinal mucosa, pulmonary mucosa, nasal mucosa and vaginal mucosa.

Another object of the present invention is to provide a liquid pharmaceutical form possessing some of the same advantages of the solid forms. Therefore, another aspect of the invention is to provide a pharmaceutical form comprising at least at one active principle in combination with a polymer dissolution in a pharmaceutical solvent, wherein the polymer dissolution comprises at least one polymer of cationic nature. This polymer dissolution hardens when placed in contact with gastrointestinal fluids by diffusion of the polymer solvent, thereby forming a polymeric matrix containing the active principle.

Another aspect of the invention provides a pharmaceutical form, which is a granule or pellet, having an average particle size diameter in the range of 0.1 to 1.0 mm, or 0.1 mm to 1.2 mm, comprising at least one active compound and a polymeric matrix, wherein: a) the active compound is selected from the group consisting of: insulins, unfractionated heparin, low molecular weight heparin, ultra low molecular weight heparins, and heparinoids; b) the polymeric matrix comprises: i) at least one polymer of cationic nature selected from the group consisting of polymer and copolymers derived from acrylic and methacrylic acids, cholestyramine and natural polymers; and ii) at least one biodegradable polymer selected from the group consisting of polyesters, polycaprolactones, polymers and copolymers derived from acrylic acid, polyethylene oxides, polypropylene oxides, polyethylene and polypropylene oxide copolymers, polyanhydrides, polyamides, polyurethanes, polycarbonates, polyacetals, polyorthoesters, polycyanacrilates, polydioxanones, poly(α-hydroxy acids), poly (β-hydroxy acids) polyphosphazenes, natural polymers; mixtures, copolymers and terpolymers thereof; c) at least 80% wt. of the active compound is in the interior of the pharmaceutical form; d) the pharmaceutical form provides an immediate release of at least 50% of active compound within 120 min or less after the pharmaceutical form is exposed to an aqueous environment; and e) the active compound is embedded within or surrounded by the polymeric matrix.

The invention includes all combinations and subcombinations of the aspects, objects, embodiments and subembodiments of the invention described herein.

DESCRIPTION OF THE FIGURES

The following figures form part of the present description and describe exemplary embodiments of the claimed invention. The skilled artisan will, in light of these figures and the description herein, be able to practice the invention without undue experimentation.

FIGS. 1A and 1B: depict a process for obtaining granulates including a primary granulation step (FIG. 1A) and a step of adding the polymers to the primary granules thus formed (FIG. 1b).

FIGS. 2A-2B: depict dry granules (G×10) (FIG. 2A); granules dispersed in 4% PVA solution (G×10) (FIG. 2B).

FIGS. 3A-3D: depict plots of the average manufacturing yields obtained for different granules prepared with 2000 (FIG. 3A), 3000 (FIG. 3B), 4000 (FIG. 3C) and 5000 (FIG. 3D) U anti-Xa of enoxaparin after mixing with Eudragit® RS 30 D (RS), and Aquacoat® ECD (AqC); 100/0, 75/25, 50/50, 25/75, 0/100% (n=3 ± standard deviation).

FIGS. 9A-9B: depict release profiles for the release of tinzaparin from primary granules mixed with different quantities of Eudragit® RS dissolved in acetone (n=3). The graph on the left (FIG. 9B) corresponds to the addition of Eudragit® in a single stage, and the graph on the right (FIG. 9A) corresponds to the addition of Eudragit® in 4 stages of 200 mg each.

FIGS. 13A-13B: depict release profiles for the release of enoxaparin from pellets with an average diameter between 0.5 and 0.8 mm (FIG. 13A) and with an average diameter comprised between 0.8 and 1.2 mm (FIG. 13B) (n=3).

DETAILED DESCRIPTION OF THE INVENTION

Figure 4:
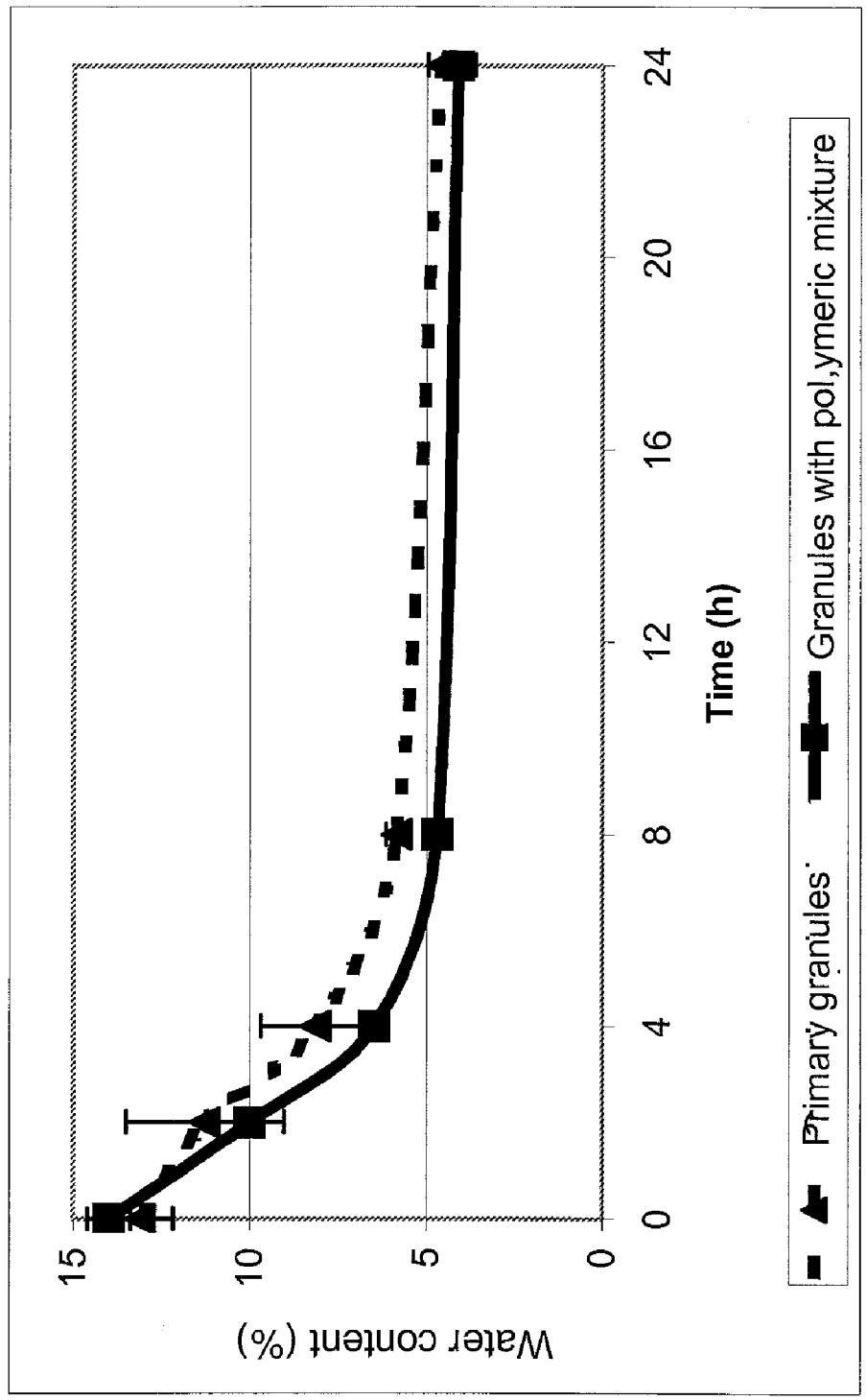
FIG. 4: depicts a graph of the time-dependent reduction in water content of the primary granules and of the granules with polymer mixture by the addition of Eudragit® RS 30 D and Aquacoat® ECD in equivalent quantities (50/50) after 2, 4, 8 and 24 hours of drying at 40° C. (n=3 ± standard deviation).
Figure 5A:
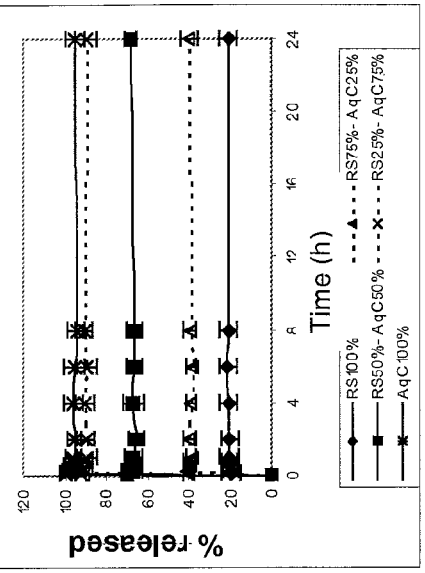
FIGS. 5A-5D: depict release profiles for the release enoxaparin (%) from different primary granules of microcrystalline cellulose mixed with aqueous suspensions containing Eudragit® RS 30 D and/or Aquacoat® ECD prepared with 2000 (FIG. 5A), 3000 (FIG. 5B), 4000 (FIG. 5C) or 5000 (FIG. 5D) U anti-Xa of enoxaparin (n=6 ± standard deviation).
Figure 5B:
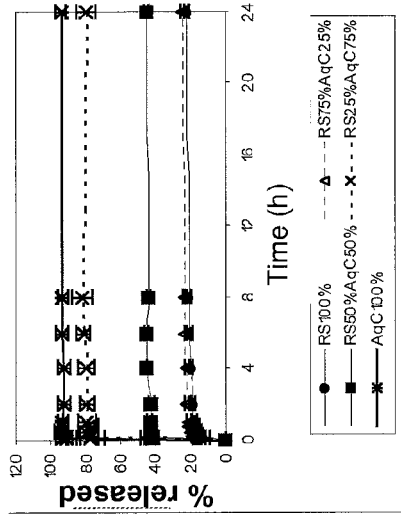
Figure 5C:
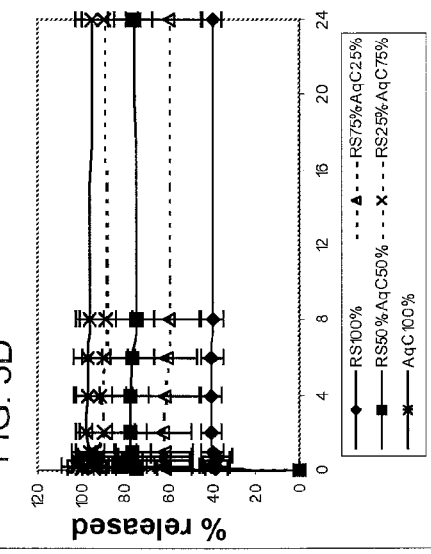
Figure 5D:
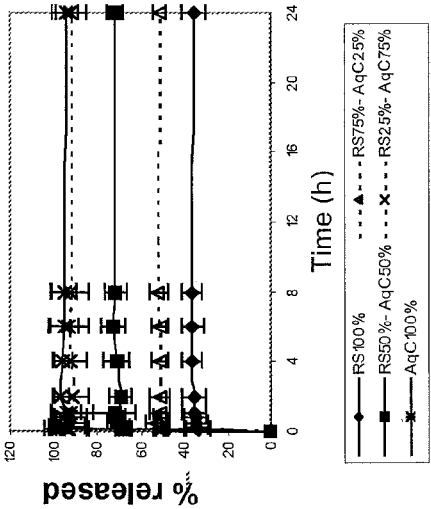

As used in the description, the following terms have the meaning indicated below, unless otherwise stated.

"Polymeric matrix" means the structure comprising a solid or semisolid mass of polymer or a polymer mixture, either alone or mixed with one or more excipients.

"In contact" means that, in the pharmaceutical form, the active compound is either intimately mixed with the polymer matrix (full contact) or it is partially mixed with the polymeric matrix, for instance when the core (in which the active compound is present) is overcoated by a composition comprising the polymeric matrix (partially in contact)

"Non-extended release form or formulation" is a pharmaceutical form or formulation that releases the active compound immediately after dosing and does not allow a reduction in dosage frequency. The pharmaceutical form or formulation does not contain sustained release polymers. After administration to a subject, this type of form will release all of the available amount of active compound within a period of 5 hours or less, 4 hours or less, 3 hours or less, 2.5 hours or less, 2 hours or less, 1.5 hours or less, 1 hour or less, or 30 min or less. In most cases, 2 hours are enough to release all available active compound, such as bemiparin, in vitro under sink conditions.

"Poorly permeable hydrophilic molecule" refers to a molecule with an affinity for aqueous media and which exhibits a low absorption through mucous membrane in a determined site. Thus, for example, hydrophilic molecules with a negative charge at pH greater than or equal to 4 will have difficulty to pass through the digestive tract mucosa which is coated by negatively charged mucus and which has a natural tendency to repel molecules with the same charge.

"Biodegradable" refers to a material that can be degraded in the body of a subject, so that is generally not eliminated intact.

"Granules" are understood to be formulations constituted by agglomerates of particles or powders of small size, which may have an irregular or spherical shape. Granules can be used as intermediate products in the manufacture of a pharmaceutical form, and they may also be used as end product.

"Core" is the inner part of a granule or a pellet, and it contains the active principle. The active compound in the core can either be dispersed throughout the whole mass of the core or can be provided as a drug-containing coating layer on an inert seed.

"Inert seed" is a bulk substance (e.g. microcrystalline cellulose, starch, sucrose or any other inert material) with spherical or non-spherical form intended to be used as substrate for further coatings, in particular drug-containing coatings.

"Pellet" is understood to be a material which is compacted in the form of small spheres or cylinders by procedures such as compaction, extrusion and/or spheronization (fusion of the solid mass, wetting of the dry mass, extrusion of the wet or melted mass and rotation of the extrudate by spheronization and subsequent drying). The pellet may contain the active compound therein, such as distributed throughout the mass of the pellet, or may serve as support (substrate) for the addition of the active compound on its surface, as by a coating on the pellet.

As regards the process for the preparation of a pharmaceutical form, the term "combining" means that the active compound may or may not be put in contact with the polymer of cationic nature, e.g., the active compound may be mixed with the polymer of cationic nature or may be forming a "core", optionally separated from the cationic polymer by an intermediate layer.

"Conditions that a polymeric matrix is formed" means conditions wherein a solid or semisolid mass of a polymer or polymer mixture and optionally one or more excipients, and optionally comprising at least one active compound, is formed (e.g. granulation, extrusion, layering, etc.)

"Maximum sink" gradient conditions are conditions for the determination of active substance release in vitro at which the maximum concentration of active compound which can be released in a release medium is lowered to 30% of the saturation concentration, with the aim that the concentration gradient can be considered not limiting.

"Biomaterial" includes all materials capable of being in contact with body tissues with specific therapeutic, diagnostic or preventive purposes. These materials must be biocompatible.

"Biocompatible" refers to a material which causes no significant adverse response of the physiological medium after interacting with body tissues and fluids, and in some embodiments, it must biodegrade, chemically as well as physically, or by a combination of the two, into no-toxic components.

One aspect of the invention relates to a pharmaceutical form comprises at least an active compound and a polymeric matrix, wherein the active compound is a poorly permeable hydrophilic molecule containing groups with negative charges at pH greater than or equal to 4 and the polymeric matrix comprises at least one polymer of cationic nature, characterized in that the active compound is not selectively distributed on the surface of the pharmaceutical form.

In the present invention, the expression 'the active compound is not selectively distributed on the external (exterior) surface of the pharmaceutical form' should be understood to mean that a substantial percentage (major portion) of the active compound present in the pharmaceutical form is not accumulated on the surface of the pharmaceutical form or composition. In other words, the drug is not selectively distributed on the external surface of the polymeric matrix. Instead, a majority of the active compound in the pharmaceutical form is embedded within the interior of the pharmaceutical form. Even so, the pharmaceutical form provides a rapid and high rate and extent of active compound absorption across the mucosa after administration.

In some embodiments, less than 10% wt., less than 7% wt., less than 5% wt., less than 2.5% wt., less than 1% wt., less than 0.5% wt., less than 0.1% wt. or substantially none of the active compound is present at the surface of the pharmaceutical form. In some embodiments, at least 90% wt., at least 93% wt., at least 95% wt., at least 97.5% wt., at least 99% wt., at least 99.5% wt., at least 99.9% wt. or substantially all of the active compound is present in the interior of the pharmaceutical form.

According to a preferred embodiment, the polymeric matrix forms part of the surface of the pharmaceutical form.

In some embodiments of the pharmaceutical form of the invention, the polymeric matrix is in contact with the active principle.

Additionally, the matrix optionally contains one or more compounds selected from plasticizers, glidants, absorption enhancers, humectants, surfactants, coloring agents and dispersants.

In some embodiments of, at least 30% of the active compound (present in the pharmaceutical form or available for immediate release in the pharmaceutical form) is released in less than or equal to 60 minutes after administration, or at least 50% of the active compound is release in less than or equal to 60 minutes after administration.

In some embodiments, the average diameter of the pharmaceutical form is at least 0.1 mm, and preferably an average diameter between 0.1 and 1.2 mm In some embodiments, the pharmaceutical form is a non-extended release form, meaning that it releases its charge of immediate release available active compound in less than or about 5 hours.

In some embodiments, the active compound in the pharmaceutical form of the invention is a poorly permeable hydrophilic molecule containing groups with negative charges at pH greater than or equal to 4. Exemplary poorly permeable hydrophilic molecules can be selected from the group consisting of antibiotics, anti-inflammatory agents, anti-infectious agents, antiparasitic agents, hormones, substances with immunological activity, vaccines, immunomodulators, immunosuppressants, cytostatic agents, diuretics, agents with activity in the digestive system, agents with activity in the circulatory system, agents with activity in the respiratory system, human growth hormone, recombinant growth hormone, bovine growth hormone, growth-hormone releasing hormone, interferons, analgesics, agents with activity in the central nervous system, erythropoietin, somatostatin, gonadotropin-releasing hormone, follicle-stimulating hormone, oxytocin, vasopressin, parathyroid hormone, adrenocorticotropin, gonadotropin-releasing hormone, thrombopoietin, calcitonin, interferons, interleukins, insulins, unfractionated heparin, low molecular weight heparin, ultra low molecular weight heparins, heparinoids, dermatan, glucosamines, chondroitins, auricular natriuretic factor, monoclonal antibodies, protease inhibitors, filgrastim, prostaglandins (PGE2 and PGI2), cyclosporin, cromolyn sodium, cromoglycate and its salts, vasopressin, vancomycin, neomycin, desferrioxamine, antimicrobial agents, antifungals, cytostatics, immunomodulators, vitamins, antivirals, antigens, ribonucleic acid, deoxyribonucleic acid, oligonucleotides, CPG sequences, plasmids, active compounds of protein nature, active compounds of polysaccharide nature, glucocerebrosidase, glycosaminoglycans, highly sulfated glycosaminoglycans, and derivatives and combinations thereof. In some embodiments, it is selected from the group consisting of insulins, unfractionated heparin, low molecular weight heparin, ultra low molecular weight heparins and heparinoids (Low- and ultra-low-molecular-weight heparins. *Best Pract. Res. Clin. Haematol.* 2004; 17: 77-87). In some embodiments, it is low molecular weight Tarja of the in. The unfractionated heparin is a heterogeneous mixture of sulfated mucopolysaccharide chains whose molecular mass is between 3,000 and 30,000 daltons. Its average molecular mass is 15,000 Daltons, and it corresponds to a heparin molecule of around 45 osidic units.

If a chemical or enzymatic depolymerisation is performed, heparins consisting of shorter chains, and consequently, with a lower molecular mass, between 1,000 and 10,000 daltons are produced. Their average molecular mass is 4,500 daltons. These compounds, called low molecular weight heparins (LMWH), are then distinguished from unfractioned heparins (UH) by a predominantly anti-Xa activity.

For the purposes of the present invention, "Low Molecular Weight Heparin" is a sulphated glycosaminoglycane salts with an average molecular weight less than 8000 Da and with a 60% of the molecules having a molecular weight less than 8000. These molecules have different chemical structures as well as different reducing and non-reducing ends of the polysaccharide chains. Standard heparin comprises fragments with a variable molecular mass of 2,000 to 30,000 Da, and therefore has activity on the two factors, Xa and IIa. Anti-factor Xa activity is not less than 70 IU per milligram of dry substance. Anti-factor Xa to anti-factor IIa is not less than 1.5. "Ultra-Low Molecular Weight Heparin" is a sulphated glycosaminoglycane salts with an average molecular weight less than 4000 Da. These molecules have different chemical structures as well as different reducing and non-reducing ends of the polysaccharide chains. Anti-factor Xa activity is not less than 70 IU per milligram of dry substance. Anti-factor Xa to anti-factor IIa is not less than 10.

In some preferred embodiments of the pharmaceutical form of the invention, the matrix comprises at least one polymer of cationic nature and at least another polymer of anionic or neutral nature.

According to some embodiments of the polymeric matrix of the pharmaceutical form, at least one polymer of anionic or neutral nature and at least one polymer of cationic nature are present in a proportion of at least 10% each in relation to the weight of the polymeric matrix, meaning the polymeric matrix comprises 10-90% by weight of at least one polymer of anionic or neutral nature and 10-90% of at least one polymer of cationic nature.

In some embodiments, the polymer matrix is such that the percentage of the polycationic polymer ranges between 1% and 99% relative to the biodegradable polymer. In some embodiments, the biodegradable polymer and the polycationic polymer are present in approximately the same or about equivalent amounts.

In some embodiments, the proportion of polymer of cationic nature to anionic polymer or neutral polymers ranges from 10% wt. to 90% wt. of cationic polymer based upon the total weight of cationic polymer plus anionic or neutral polymer. In other embodiments, the proportion of polymer of cationic nature to anionic polymer or neutral polymers ranges from 40% wt. to 60%/wt. wt. of cationic polymer based upon the total weight of cationic polymer plus anionic or neutral polymer. In some embodiments, the weight of cationic polymer approximates or is the same as the weight of anionic or neutral polymer.

In some embodiments, the polymer of cationic nature in the polymeric matrix of the pharmaceutical form is selected from polymers and copolymers derived from acrylic and methacrylic acids, and natural polymers.

For the purposes of the present invention, the biodegradable polymers and the polycationic polymers may or may not be gastroresistant (enteric).

In some embodiments, the polymer of anionic or neutral nature in the polymeric matrix of the pharmaceutical form is selected from the group consisting of: polyesters, polycaprolactones, polymers and copolymers derived from acrylic acid, polyethylene oxides, polypropylene oxides, polyethylene and polypropylene oxide copolymers, polyanhydrides, polyamides, polyurethanes, polycarbonates, polyacetals, polyorthoesters, polycyanacrilates, polydioxanones, poly($\alpha$-hydroxy acids), poly($\beta$-hydroxy acids) polyphosphazenes, natural polymers; mixtures, copolymers and terpolymers thereof. More particularly, the polymers of anionic or neutral nature the polyesters can be selected from the group consisting of: lactic acid polymers, glycolic acid polymers, lactic and glycolic acid copolymers; the polycaprolactone is poly-$\epsilon$-caprolactone; the acrylic acid derived polymers can be selected from the group of polymethylmethacrylates; and the natural polymers are selected from the group of cellulose derivatives formed by microcrystalline cellulose, hydroxypropylmethylcellulose and ethyl cellulose; mixtures, copolymers and terpolymers thereof. Even more particularly the polymers of anionic and neutral nature in the polymeric matrix are biodegradable.

In some embodiments, the polymeric matrix comprises polyesters and natural biodegradable polymers as polymers of anionic or neutral nature and methacrylic acid derivatives with quaternary ammonium groups as polymers of cationic nature. Particularly, the polymeric matrix comprises poly-$\epsilon$-caprolactone as a polymer of anionic or neutral nature and a polymer derived from methacrylic acid with quaternary ammonium groups as a polymer of cationic nature. More particularly, the polymer derived from methacrylic acid with quaternary ammonium groups is a trimethylammonioethyl methacrylate chloride copolymer.

In some embodiments, the nonenteric biodegradable polymer is selected from the group consisting of polyesters, especially lactic acid polymers, copolymers of lactic acid and of glycolic acid (PLGA), poly-$\epsilon$-caprolactone (PCL), polyanhydrides, poly(amides), poly(urethanes), poly(carbonates), poly(acetals), poly(ortho-esters) and natural polymers (collagen, polysaccharides, etc.).

In some embodiments, the biodegradable polymer is either PCL or PLGA, the molecular weight of said polymers being between 2,000 and 100,000.

In some embodiments, the polymeric matrix of the pharmaceutical form comprises a polyethylene and polypropylene oxide copolymer as polymer of neutral nature and a polymer derived from methacrylic acid with quaternary ammonium groups as polymer of cationic nature. In other embodiments, the polymeric matrix of the pharmaceutical form comprises a polylactic-co-glycolic acid copolymer as polymer of neutral nature and a polymer derived from methacrylic acid with monomers of trimethylamonioethyl methacrylate.

Among the solid forms used for the administration of active compounds, granules, coated granules and pellets are included. Therefore, in some embodiments, the pharmaceutical form of the invention is a granule, and in other embodiments, it is a pellet.

When the pharmaceutical form of the invention is a granule, it comprises a core and a polymeric matrix, wherein said core comprises at least an active compound and said polymeric matrix comprises at least one polymer of cationic nature. The polymeric matrix further may comprise at least one polymer of anionic or neutral nature.

In some embodiments, the polymeric matrix forms part of the core of the granule.

In some embodiments, the polymeric matrix in the granule forms a coating layer on or over the core. In embodiments wherein the polymeric matrix exerts an undesirable effect on the active compounds, the presence of an intermediate coating layer between the active compounds and the polymeric matrix is useful in order to avoid the contact. The intermediate coating layer may comprise any substance providing physical separation between the core and the polymeric matrix. Examples of coating substances can be, but need not be, limited to: cellulose derivatives, copolymers of acrylic or methacrylic acid polyethylene oxides, polypropylene oxides, polyethylene and polypropylene oxide copolymers, gelatin, lactose, mannitol. The intermediate coating layer may also comprise any one or more excipient(s) commonly used in surface coating such as glidants and plasticizers.

According to some embodiments, the core in the granule may comprise an inert seed wherein the active compound form part of a layer coating said seed. In this case, the core also may comprise an intermediate layer between the inert seed and the layer comprising at least an active compound. This intermediate layer is useful for sealing the inert seed in order to avoid the deleterious effect of moisture. Therefore, this layer comprises any compound intended to protect from moisture e.g. ethyl cellulose, hydroxypropyl methyl cellulose, neutral polymers derived from methacrylic acid e.g. Eudragit® NM or Eudragit® NE, poloxamers and high molecular weight polyethyleneglicols (e.g. PEG 8000), polyvinyl acetate phthalate, cellulose acetate phthalate and waxes.

In some embodiments, the cationic polymer (or polycationic polymer) is selected from the group consisting of cationic cellulose derivatives, the cationic copolymers of acrylic and methacrylic acid esters sold by the company Rhöm GmbH under the name Eudragit® and more particularly cationic methacrylic acid polyesters with a small proportion of trimethylammonioethyl methacrylate chloride (Eudragit® RS) or a larger proportion of trimethylammonioethyl methacrylate chloride (Eudragit® RL), chitosan and its derivatives, and polylysine.

Eudragit® RS 30 D (provided by Degussa; Darmstadt, Germany), is a copolymer of trimethylammonioethyl methacrylate chloride which has an overall positive charge with a low concentration in quaternary ammonium groups (from 8 to 12%). This polymer is a nonbiodegradable synthetic polymer. It is not absorbed nor metabolized, for which reason it is eliminated intact. It is insoluble in water but soluble in organic solvents. It is presented in the form of an aqueous suspension at a polymer concentration of 30% (m/v).

Aquacoat® ECD, kindly provided by FMC BioPolymer (Newark, Del., USA.), corresponds to a suspension of a synthetic polymer of ethyl cellulose, non-ionic, insoluble in water but soluble in organic solvents. Aquacoat® ECD is used in the pharmaceutical industry for the manufacturing of granules and matricial systems, as well as for coating tablets. It is also available in the form of an aqueous suspension at a polymer concentration of 30% (m/v).

Eudragit® RS PO is a copolymer of trimethylammonioethyl methacrylate chloride which has an overall positive charge with a low concentration in quaternary ammonium groups (from 8 to 12%). This polymer is a non-biodegradable synthetic polymer. It is not absorbed or metabolized, for which reason it is eliminated intact. It is insoluble in water but soluble in organic solvents. It is presented in the form of dry powder.

When the pharmaceutical form of the invention is a pellet, it comprises at least one active compound and a polymeric matrix, wherein said polymeric matrix comprises at least one polymer of cationic nature. The polymeric matrix further may comprise at least one polymer of anionic or neutral nature.

When the pharmaceutical form is a liquid it comprises at least one active principle in combination with a dissolution of a polymer in a pharmaceutical solvent, wherein the polymer dissolution comprises at least one polymer of cationic nature. The liquid form can be e.g. a suspension of at least one active principle in a dissolution of a polymer in a pharmaceutical solvent, wherein the polymer comprises at least one polymer of cationic nature.

The pharmaceutical dosage forms can be manufactured or produced by various different processes. By way of example and without limitation, the granules or pellets can be prepared by dry granulation, wet granulation, fluidized-bed spray granulation or spheronization.

In dry granulation, the form is produced by the aggregation of the powder components subjected to high pressure followed by a fragmentation or breaking into pieces and subsequent separation by sieving to achieve the desired granule size. The techniques more commonly used are slugging and roll compaction (Roll compaction/dry granulation: pharmaceutical applications. Kleinebudde, Peter. *European Journal of Pharmaceutics and Biopharmaceutics* (2004), 58(2), 317-326).

In wet granulation, a powder mixture is kneaded in the presence of a granulation liquid, e.g. water, organic solvent or combination thereof, which optionally comprises a binding agent dissolved or be incorporated with the other mixture components to favor the adhesion of particles once the granules have dried (Theophylline granule formulation prepared by the wet granulation method: comparison of in vitro dissolution profiles and estimation of in vivo plasma concentrations. Karasulu et al. *European Journal of Drug Metabolism and Pharmacokinetics* (2007), Volume 31(4), 291-298).

In fluidized bed spray granulation, the granulation liquid is sprayed on the particles suspended in air current (Experimental study of wet granulation in fluidized bed: Impact of the binder properties on the granule morphology. Rajniak, P et al. *International Journal of Pharmaceutics* (2007), 334(1-2), 92-102). This procedure also permits coating preformed granules as well as obtaining granules from inert seeds on which a suspension or dissolution of the active compound is applied (Preparation and evaluation of sustained release indomethacin nonpareil seeds. The-Mahrouk et al. *Drug Development and Industrial Pharmacy* (1993), 19(15), 1903-16) for example, nonpareil starch or sugar cores or microcrystalline cellulose spheres.

Spheronization can also be used to prepare the pharmaceutical form of the invention. (The preparation of pellets containing a surfactant or a mixture of mono- and di-glycerides by extrusion/spheronization. Newton, et al. *European Journal of Pharmaceutical Sciences* (2007), 30(3-4), 333-342).

The invention also provides a process for the preparation of the pharmaceutical dosage forms aforementioned, the process comprising combining at least an active compound and at least one polymer of cationic nature in conditions that a polymeric matrix is formed.

In some embodiments, the process comprises the step of subjecting a composition comprising at least one active compound to a granulation process to produce a core. Particularly, the composition further comprises at least one polymer of cationic nature. More particularly, the composition further comprises at least one polymer of anionic or neutral nature. Even more particularly, the process further comprises the step of coating the core with a composition comprising at least one polymer of cationic nature, and preferably, the composition of the coating further comprises at least one polymer of anionic or neutral nature.

According to some embodiments, the process for preparing a pharmaceutical form of the invention comprises the steps of:
a) coating an inert seed with a composition comprising at least one active compound to obtain a core; and
b) coating the core with a composition comprising at least a polymer of cationic nature.

In some embodiments, the process further comprises: in step a), coating the inert seed with a composition to form an intermediate coating layer before performing the coating with a composition comprising at least one active principle.

In some embodiments, the composition used in step b) further comprises at least one polymer of anionic or neutral nature. In some embodiments, a spray method is used in the coating performed in step b).

The processes described herein may further comprise the step of coating the core with a composition to form an intermediate coating layer. The presence of an intermediate layer protects the active compound when it can be affected by the polymers comprised in the matrix.

Some embodiments of the invention provide a process for preparing a pharmaceutical form, the process comprising:
a) mixing at least one active compound with at least one polymer of cationic nature to form a homogenized mixture; and
b) extruding the homogenized mixture.

In some embodiments, the active compound is further mixed with at least one polymer of anionic or neutral nature in step a).

When the pharmaceutical form is a liquid, one method for its manufacture can comprise:
a) preparing a dissolution comprising at least one polymer of cationic nature dissolved in a pharmaceutically acceptable dissolvent;
b) preparing a dissolution of at least one active principle dissolved in a pharmaceutically acceptable solvent; and
c) combining the dissolutions obtained in a) and b), thereby providing the liquid pharmaceutical form.

In some embodiments, the liquid form may be a suspension.

Generalized exemplary processes for preparation of the pharmaceutical dosage forms of the invention include:
Preparing granules comprising a core of active compound and microcrystalline cellulose with a coating representing a weight gain with respect to the uncoated granule of 4%, wherein the coating composition is selected from:
i. Eudragit® RS and polycaprolactone in a 1:1 ratio dissolved in acetone,
ii. Eudragit® RS and PLGA in 1:1 ratio dissolved in an organic solvent,
iii. Eudragit® RS and polyethylene and propylene oxide copolymer in a 1:1 ratio dissolved in acetone, or
iv. Eudragit® RS and Aquacoat™ in 1:1 ratio in aqueous suspension;
Preparing granules as above but further applying an intermediate coating of cellulose derivatives (cellulose acetate phthalate or hydroxypropyl methylcellulose phthalate), or Eudragit® L or S to confer gastroresistance and non-gastric release;
Preparing granules by wet granulation employing carboxymethylcellulose and heparin dissolved in water, and subjecting the granulate to secondary granulation with Eudragit® RS;
Preparing granules by wet granulation employing microcrystalline cellulose+active compound dissolved in water and an aqueous suspension of Eudragit® RS wherein the microcrystalline cellulose:Eudragit® RS is 1:0.8; or
Preparing a heparin pellet by extrusion/spheronization of microcrystalline cellulose and Eudragit® RS and 2.66:1 ratio.

The pharmaceutical form according to the present invention may be subsequently processed to obtain a pharmaceutical formulation which is the final product to be administrated to a patient. The features of the pharmaceutical formulation depend on the route of administration, particular release profiles, or other intended effects.

The route of administration of the pharmaceutical form, pharmaceutical composition, pharmaceutical formulation or pharmaceutical dosage form can be selected from oral, peroral, sublingual, intraduodenal, intrajejunal, intraileal, intracolonic, rectal, intravaginal, nasal, intrapulmonary, ocular and/or otic route.

The granules and pellets thus produced can be designed for the preparation of tablets and/or capsules (Characterization of 5-Fluorouracil Release from Hydroxypropylmethylcellulose Compression-Coated Tablets. Wu et al. *Pharmaceutical Development and Technology* (2007), 12(2), 203-210), or they can be subject to additional treatments such as polymeric coatings of granules produced to possess the properties of gastroresistance (In vitro dissolution studies of sodium diclofenac coated granules with Eudragit® L-30D-55 by fluidized-bed system. Silva, O R. et al. Drug Development and Industrial Pharmacy (2006), 32(6), 661-667) by employing, for example, polyvinyl acetate phthalate, hydroxypropyl methylcellulose phthalate, acrylic copolymers as methacrylic acid and methacrylic ester copolymers, hydroxypropylmethylcellulose acetate succinate, etc., or of mucoadhesion by employing, for example, chitosan, or other such materials bioadhesive materials.

Another aspect of the invention provides a pharmaceutical formulation comprising a pharmaceutical form as described herein. In some embodiments, the pharmaceutical formulation is a non-extended release formulation. In some embodiments, the formulation is a tablet, capsule, granule, sache, pellet, lyophile (lyophilate), serum, syrup, microparticulate powder, oily suspension, liposome, micelle, self-emulsifying system, and other dispersed systems.

Oral administration continues being an attractive route for the release of pharmacologically active molecules. Its easy administration, the absence of pain associated to the administration, the greater acceptance by the patient, and favorable cost/benefit ratio have turned these oral formulations into the most widely used for the administration of active compounds by oral route. In some embodiments, the pharmaceutical formulation is adapted for oral administration.

Another aspect of the invention provides the use of the pharmaceutical form, as described herein for the preparation of a pharmaceutical formulation. In some embodiments, the pharmaceutical formulation is not an extended release formulation.

Another aspect of the invention provides the use of a pharmaceutical form or a pharmaceutical formulation as defined herein, in the preparation of a medicament applicable to mucosa (mucosal tissue or membrane) selected from oropharyngeal mucosa, gastrointestinal mucosa, pulmonary mucosa, nasal mucosa and vaginal mucosa.

Another aspect of the invention provides the use of the pharmaceutical form or pharmaceutical formulation as a medicament applicable to mucosa selected from the group formed by oropharyngeal mucosa, gastrointestinal mucosa, pulmonary mucosa, nasal mucosa and vaginal mucosa.

By way of summary, the results disclosed by the present invention favors the absorption of molecules, particularly, those whose systemic bioavailability is more limited by the reduced permeability in the absorption barrier of the molecule, due to the reduced solubility thereof in the luminal fluids by mucosal route, preferably administered by oral route, especially for molecules which in the state of the art are commonly known for their low and/or erratic absorption by oral route.

The pharmaceutical forms (compositions) of the invention can be characterized according to, among other properties, method of preparation, morphology, average particle size (diameter), manufacturing yield during preparation, water content, in vitro drug release performance, nephelometry, drug content, etc.

The processes described herein for preparation of the pharmaceutical form achieve yields of incorporation of the active compound of at least 80%, which is an advantage over known microparticle and/or nanoparticle formulations. This means that at least 80% of the active compound that is added to other components forming the pharmaceutical form is incorporated in the final pharmaceutical form during preparation thereof. In some embodiments, at least 85%, at least 90%, at least 95% or at least 99% of the active compound is incorporated.

The manufacturing yield (amount of active agent incorporated into the granules as compared to the amount of active agent used to prepared the granules) for preparation of granules comprising enoxaparin (Example 2) was determined. The results are depicted in FIG. 3. Yields were greater than 85%, greater than 90%, greater than 95% or even up to 99%.

FIG. 4 depicts the decrease in water content over time during the drying stage of the primary granules and of those mixed with Eudragit® RS 30 D and Aquacoat® ECD 50/50 (Example 2), with little significant differences between the primary granules and the coated granules. An average water content of around 4% is obtained 24 h after drying for the two types of granules, with little difference between 8 h (from 4 to 6%) and 24 h (from 3 to 5%) of drying. The average water content for each form of enoxaparin granules prepared with different quantities of LMWH and later mixed with different proportions of polymer ranges from 2% to 4%.

This preliminary study has been performed in order to standardize the drying time of the primary granules and of the granules containing polymer mixture. This study shows a stable water content between 2 and 5% after 24 hours of drying, both for the primary granules and for the granules containing the polymer mixture. This drying time, in accordance with the general characteristics of the granules, is maintained for the other assays. The water content of the granules is a parameter which can affect the stability of the granules. In effect, prolonged drying at 40° C. can degrade the enoxaparin, and too high a water content may entail degradation of the polymers. The water can, indeed, play a role of plasticizer which modifies the physicochemical properties of the polymers, and thus reduces the stability of the drug form.

The 2-stage manufacturing process of Example 2, for granules containing a polymer mixture of the active compound and a polymer (dispersion of Low molecular weight heparin (enoxaparin) in the cellulose polymer and subsequent mixing with different polymers for the formation of the final granule), permits reaching high manufacturing yields with very little losses throughout the process. Accordingly, the invention provides a high production yield and low materials cost process for preparing pharmaceutical forms and compositions.

The results of the dissolution kinetics (release profiles) is expressed as percentage of enoxaparin released with respect to the initial quantity used during the preparation of the granules or in IU of enoxaparin released per gram of granules (FIG. 5). The dissolution kinetics all have the same profile characterized by an important initial phase called "burst" wherein practically all the enoxaparin which can be released, i.e. all of the enoxaparin which is available for immediate release, is released, and a second phase consisting of a plateau, wherein substantially no enoxaparin is released. Generally, the more Eudragit® RS 30 D that a formulation contains and the greater its percentage of the polymer, the lower the number of IU of enoxaparin released. In contrast, the more ethyl cellulose a formulation contains, the greater the release of heparin.

The data herein from the in vitro studies confirm the existence of electrostatic interactions between the quaternary ammonium groups of Eudragit® RS 30 D and the carboxyl and sulfate groups of enoxaparin. In brief, it is believed that the more Eudragit® RS 30 D the granules contain, the less enoxaparin they release. In contrast, for the primary granules constituted by the mixture of microcrystalline cellulose and mixed with ethyl cellulose, the in vitro dissolution studies show a total release of the enoxaparin, which suggests an absence of interaction between enoxaparin and ethyl cellulose, a polymer without overall charge. Furthermore, for the same quantity of Eudragit® RS 30 D, the greater the increase in the quantity of enoxaparin used during the preparation of the granules, the greater quantity of enoxaparin released (FIG. 5). If we take as an example the primary granules of microcrystalline cellulose mixed with an aqueous dispersion which contains 100% Eudragit® RS 30 D (FIG. 6), no release of enoxaparin occurs in our experimental conditions when 500 and 1,000 units of anti-Xa have been used to prepare the granules, while there appears a release for the granules which contain 2,000, 3,000, 4,000 or 5,000 IU of enoxaparin. Without being held to a particular mechanism, we believe that the quantity of Eudragit® RS 30 D is sufficient to fix/bind all the 500 and 1,000 IU enoxaparin by electrostatic bonds that are difficult to break in the dissolution conditions of this assay. In general, the lower the amount of heparin present, the more chains thereof can be fixed/bound to several points on the quaternary ammonium groups of Eudragit® RS 30 D, thereby not favoring release of the final amounts of heparin remaining in the granules.

Accordingly, the invention provides a pharmaceutical form comprising: an active compound as defined herein, at least one cationic polymer, and at least one anionic or neutral polymer, wherein a first portion of the active compound is ionically bound to the cationic polymer and is not released following administration. In general, about 40-99%, or at least 40%, at least 50% or at least 70%, of the total amount of active compound present in the pharmaceutical form is available for immediate release. In general, about 1-60%, or less than 60%, less than 50%, or less than 30%, of the total amount of active compound present in the pharmaceutical form is not available for immediate release. The amount of heparin that is available for immediate release can also be calculated in vitro, but as heparin disappears from the release medium (e.g. because of absorption or degradation) after administration in vivo, the equilibrium is displaced toward the rupture of the ionic interaction between heparin and the polymeric matrix of the pharmaceutical form and thus 100% of heparin might be released at the extend of an extended period of time.

The pharmaceutical form of the invention provides high loading capacity for active compound. In some embodiments, the active compound is present in an amount of at least about 5% and can be present in amounts up to 20% by weight of the pharmaceutical form. The amount of active compound present in the pharmaceutical form can be varied as needed to provide dosage forms and compositions containing therapeutically effective amounts of active compound therein.

In some embodiments, the particulate vector or pharmaceutical form is adapted for administration of heparin at a dose of between 2,000 IU and 20,000 IU/day or LMWH at a dose of between 600 IU and 4,200 IU/day.

The invention also provides a method of treating a disorder therapeutically responsive to any one or more active compounds by administration of a pharmaceutical composition comprising a therapeutically relevant dose (or effective dose), of said one or more compounds, according to a predetermined dosing regimen. It should be noted that a therapeutic response can be a full or partial response at therapeutically relevant doses to a subject according to a predetermined dosing regimen. A therapeutically relevant dose will vary from subject to subject according to the active compound administered as well as a variety of established pharmacologic, pharmacodynamic and pharmacokinetic principles.

A therapeutically relevant dose can be administered according to any clinically acceptable dosing regimen typically used in the treatment of diseases or disorders. The therapeutically relevant dose is administered according to a predetermined dosing regimen, which can be modified as need according to a subject clinical response. A therapeutically relevant dose can be administered once, twice, thrice or more daily. It can be administered every other day, every third day, every fourth day, semiweekly, weekly, biweekly, every three weeks, every four weeks, monthly, bimonthly, semimonthly, every three months, every four months, semiannually, annually, or according to a combination of any of the above. For example, a therapeutically relevant dose can be administered once daily for one or more weeks. A predetermined dosing regimen is a dosing regimen prescribed by a caregiver, such as a clinician, specifying the frequency of administration of therapeutically relevant doses throughout a treatment period and specifying the duration of such treatment period. For example, a predetermined dosing regimen can include repeated administration of one or more predetermined therapeutically relevant doses at predetermined time intervals for a predetermined treatment period. The therapeutically relevant dose, predetermined time interval and treatment period can be changed dependently or independently of one another as needed and as determined by a caregiver.

An effective amount or therapeutically relevant amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of active ingredient which is enough for the required or desired therapeutic response, or in other words, the amount, which is sufficient to elicit an appreciable biological response when, administered to a patient.

The appreciable biological response may occur as a result of administration of single or multiple unit doses of an active substance. A unit dose may comprise one or more dosage forms. It will be understood that the specific dose level for any patient will depend upon a variety of factors including the indication being treated, severity of the indication, patient health, age, sex, weight, diet, pharmacological response, the specific dosage form employed, and other such factors.

The particle size of the pharmaceutical form is advantageous, as it allows for higher active compound loading per unit of surface area as compared to prior art microparticles or nanoparticles, which inherently possess very high surface areas per unit weight. The particle size is actually a measure of the particle's diameter. The particle size can be expressed as average or mean particle size. The processes described herein generally provide a mass of particles possessing a distribution of many particle size, and the mean or average size is determined in relation to the distribution of particle sizes using conventional particle size measurement techniques.

The particle size distribution of the pharmaceutical form can be generally described as follows: a) at least 95% of the particles are greater than 0.1 mm in diameter and at least 96% of the particles are less than 1.0 mm in diameter; b) at least 96% of the particles are greater than 0.125 mm in diameter and at least 98% of the particles are less than 1.25 mm in diameter; c) at least 95% of the particles are less than 1.0 mm in diameter, d) at least 40% of the particles are between 0.710 and 0.315 mm in diameter In some embodiments, the particle size distribution (determined by sieve analysis, or laser light scattering, e.g. Malvern™ Mastersizer™ apparatus) of the pharmaceutical form can be expressed as detailed in the following table, which includes the weight percentages for the individual size ranges:

| Particle Size Range (mm) | 1 | 2 | 3 | 4 |
| --- | --- | --- | --- | --- |
| <0.125 | 18% | 2% | 3% | 4% |
| 0.315-0.125 | 50.5% | 12% | 42% | 23% |
| 0.710-0.315 | 20% | 39% | 32% | 46% |
| 1.0-0.710 | 10% | 34.5% | 17% | 23% |
| 1.25-1.0 | 1.0% | 11% | 5% | 3% |
| 1.5-1.25 | 0.5% | 1% | 0.5% | 0.5% |
| 2.0-1.5 | | 0.5% | 0.5% | 0.5% |
| >2.0 | | | | |

The particle size can also be expressed according to the average particle diameter of the particles in the pharmaceutical form. Accordingly, some embodiments of the invention provide those wherein: a) the average particle size ranges from 0.1-1.2 mm, 0.125-1 mm, 0.125-0.315 mm, 0.125-0.710 mm, 0.315-0.710 mm, 0.315-1.0 mm, 0.315-1.2 mm, 0.710-1.0 mm, 0.710-1.2 mm, 0.100-0.150 mm. In some embodiments, the average particle size of the pharmaceutical form is 0.100-0.150 mm, 0.5-0.8 mm, 0.8-1.2 mm.

The absorption, via the mucosa, of active compound from the pharmaceutical form following administration thereof to a subject can vary according to the mode and site of administration. In general, a substantial portion of the active compound that is present in the pharmaceutical form and that is available for immediate release will be absorbed via the mucosa following administration. The substantial portion can be at least 20%, at least 30%, at least 40%, at least 50%, at least 60%, at least 70%, at least 80% or at least 90%.

Whenever the pharmaceutical form is administered orally, the active compound therein might undergo gastric degradation/digestion. By virtue of its composition and construction (in particular, disposition of the active compound, such as having a majority of the active compound within instead of on the surface of the pharmaceutical form), the pharmaceutical form provides reduced gastric degradation of the active compound after oral administration. In some embodiments, less than 20%, less than 10%, less than 5%, less than 2.5%, or less than 1% of the active compound present in the pharmaceutical form is degraded in the gastric region following oral administration thereof to a subject.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

EXAMPLE 1

Preparation of Granules Comprising Heparin

The heparin granules have been prepared by dispersing a heparin solution in microcrystalline cellulose (MCC) in order to produce primary granules which, then, have been mixed with the aid of an organic solution of Eudragit® RS (ERS) and poly-$\epsilon$-caprolactone (PCL) both in equivalent quantities.

As an alternative procedure, the heparin granules have been prepared by wetting the polymers with an aqueous solution containing heparin. The first stage consists of dispersing a heparin solution within a microcrystalline cellulose powder. The primary granules, produced during this stage, are then remixed with the aid of an aqueous suspension of Eudragit® RS and ethyl cellulose.

In vitro studies were performed in order to determine the manufacturing yields and the water contents of the manufactured granules, and of evaluating the in vitro release kinetics of the active compound. Finally, a preliminary study was performed in vivo on New Zealand White rabbits after oral administration of these heparin granules, in order to evaluate the absorption and oral bioavailability of heparin.

EXAMPLE 2

Preparation of Granules Comprising Enoxaparin

Enoxaparin is a low molecular weight heparin (4,500±1,000 Daltons) whose antithrombotic and anticoagulant activities are dissociated. It is characterized by higher anti-Xa activity than anti-IIa activity, the proportion between both activities being 3.6. The form used for our experiments is an aqueous solution of LOVENOX® dosed at 10,000 IU of anti-Xa/mL and commercially designed for the subcutaneous route.

The polymers used for the creating the polymeric matrix include: cellulose (a direct compression excipient; natural homopolysaccharide formed by units of $\alpha$-D-glucopyranose bound together by a 1-4 glucosidic bond), Eudragit® RS 30 D and Aquacoat® ECD.

The procedures used to granulate are described below:
Primary Granulation Stage

The first stage (FIG. 1A), termed primary granulation, consists of mixing the aqueous solution of enoxaparin (2 mL at 2,000, 3,000, 4,000 or 5.000 IU of anti-Xa) with 1 g of microcrystalline cellulose (MCC). After drying for 2 hours 30 in the oven at 40° C., the agglomerates are forced to pass through a metal sieve with a mesh opening of 600 µm. The primary granules thus produced are then dried for 24 hours in the oven at 40° C.

Addition of Polymers

The second stage (FIG. 1B), termed regranulation, consists of adding an aqueous suspension of polymers to the primary granules. The primary granules are then directly mixed with different proportions (100/0, 75/25, 50/50, 25/75, 0/100) of aqueous suspensions of aquacoat® ECD (AqC) and/or Eudragit® RS 30 D (RS) corresponding to 400 mg of polymers. The product is dried in the oven at 40° C. for 30 minutes. Once dry, the agglomerates are forced to pass through the metal sieve with a mesh opening equal to 600 µm. The granules produced are dried in the oven at 40° C. for 24 hours.

The "virgin" (control) granules, without heparin, have been prepared in the same manner, substituting the heparin solution for water. The primary granules prepared with 500 and 1,000 IU of anti-Xa are also mixed with 100% Eudragit® RS 30 D.

Finally, the primary granules produced with 500 mg of MCC and 5,000 IU of anti-Xa of enoxaparin (2 mL), and then mixed with 100% Eudragit® RS 30 D, have also been formulated according to the same procedure.

EXAMPLE 3

Characterization of the Granules

Morphology and Size

The granules were observed and photographed with an optical microscope as a dry granulate (FIG. 2A) and after having been dispersed in a 4% PVA solution (FIG. 2B). After acquisition of the image, it was analyzed by a computer program (Kappa programme) in order to determine the particle diameter of the granules.

Manufacturing Yield

The preparation yield is calculated with respect to the initial masses of cellulose, the addition polymers and enoxaparin.

Water Content

The water content of the different granules prepared was determined obtained by potentiometry using the Karl Fisher method. The water content measurements were made in duplicate for each sample. These measurements were made with the aid of model 756 KF, Metrohm SA potentiometer (Herisau, Switzerland).

In order to optimize the drying time of the primary granules and of those containing polymer mixture, the water content of the granules without heparin was measured over time after 2, 4, 8 and 24 hours of drying. With regard to the water content of the heparin granules, it was measured after 24 hours of drying.

In Vitro Release Kinetics

The objective of this assay was to determine the quantity of enoxaparin, or other pharmaceutical active, released by the granules over time. This in vitro release should be performed in defined conditions called "sink", i.e. those wherein the maximum concentration of active compound which can be released in a release medium is lower than 30% of the saturation concentration, so that the concentration gradient can be considered non-limiting.

The release assays were conducted in a water bath held at 37° C. while suspending, with gentle magnetic stirring (200 rpm), 50 mg of each batch of enoxaparin granules in 20 mL of phosphate buffer (PBS, 0.011 M and NaCl, 0.15 M) at pH 7.4.

1.5 mL sample aliquots were taken with an automatic pipette after 5, 10, 15, 30, 45 minutes, and after 1, 2, 4, 6, 8 and 24 hours. The volumes collected were substituted by 1.5 mL of fresh buffer in order to maintain a constant volume in the flasks. These aliquots were then filtered with a MILLIPORE filter with 0.22 μm porosity.

The quantities of enoxaparin released were evaluated by nephelometry, and then the curves which represent the release kinetics of enoxaparin in accordance with time were calculated. The release kinetics measurement were performed in duplicate for each one of the samples (n=2).

Nephelometric Determination

The nephelometric determination method is based on the capacity of numerous sulfate and carboxylate groups of enoxaparin to complex with quaternary ammonium groups of a 0.1% (m/v) cetylpyridinium chloride solution in the presence of an acetate buffer. The presence of the complex produced is evaluated by absorption spectrophotometry at 500 nm.

A calibration scale is made from a 10 IU/mL enoxaparin stock solution prepared in a 0.1%% phosphate buffer.

Acetate buffer (500 μL)r and cetylpyridinium chloride (2 mL) are successively added to 500 μL of each enoxaparin concentration or samples to dose. The combination is incubated at 37° C. in a water bath for one hour and then the absorbance is determined at 500 nm with the aid of a spectrometer (Uvikon 922 spectrophotometer Kontron instruments).

The release proportion is estimated form the following formula:

$$\text{Proportion released (\%)} = \frac{[(\text{units released in time } t \times 20) \uparrow (\text{units released in } t-1 \text{ per mL})] \times 100}{(\text{units encapsulated per gram of polymer}) \times 0.05 \text{ g}}$$

EXAMPLE 4

In Vivo Studies Using Granules Comprising Enoxaparin

Size 0 capsules containing enoxaparin granules were administered at a dose of 600 IU/kg to male rabbits of New Zealand White breed after a 12 hour fast, but with free access to water. Blood samples have been taken (1.5 mL) from the marginal vein of the ear at regular time intervals after oral administration (2, 4, 6, 8, 10 and 24 hours). The blood was collected in citrated tubes (1 volume of sodium citrate per 9 volumes of blood). After centrifuging the blood samples at 3,000 g during 10 minutes, the blood plasma was removed and the anti-Xa plasma activity was determined with the aid of a STAGO automaton. Granules prepared with 1 g of MCC and 5,000 IU of anti-Xa and then mixed with Eudragit® RS 30 D, with Aquacoat® ECD and with a mixture 50/50 of the two polymers, were tested.

Assay Principle of Anti-Xa Activity:

The determination was carried out together with purified antithrombin III (ATIII) as a control in order for the results not to depend on a possible lack in this protein. The principle is based on the in vitro inhibition of factor Xa by ATIII-heparin complexes by an amidolytic procedure on the chromogen substrate, according to Teien (Evaluation of an amidolytic heparin assay method: increased sensitivity by adding purified antithrombin III. Teien and Lie. *Thromb Res.* 1977; 10: 399-410).

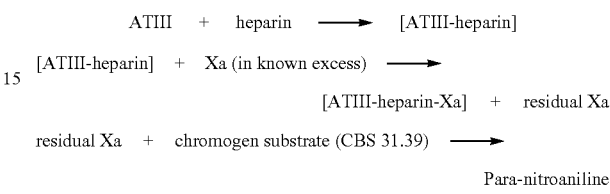

When factor Xa is fixed to a chromogen substrate, this releases para-nitroaniline, its quantity being inversely proportional to the quantity of heparin present in the initial medium. The para-nitroaniline is determined by absorption spectrophotometry at 405 nm.

A calibration scale of 0 to 0.8 IU of anti-Xa/mL is made after dilution of the enoxaparin stock solution in the Orwen Koller buffer (Stago). The measurements of the points on the scale and the plasma samples are carried out with a Strachrom kit and with the aid of a STA automaton (Stago Diagnostica).

EXAMPLE 5A

Calculation of the Relative Bioavailability Drug Using Granules Comprising Enoxaparin Bioavailability is a parameter which characterizes the proportion and rate at which an active compound is absorbed in the organism with respect to the dose administered. Normally, it is characterized by the monitoring of the unaltered molecule in the blood. The comparison of the areas under the curves after oral and subcutaneous administrations leads to the relative bioavailability, which discloses the quantity absorbed by oral route with respect to the quantity absorbed by subcutaneous route, corrected by the dose administered. The rate parameter is generally measured indirectly, measuring the time until the maximum time (Tmax) and the maximum concentration (Cmax). The relative bioavailability is calculated according to the formula:

$$\text{Relative bioavailability} = \frac{\text{area under the curve, oral} \times \text{subcutaneous dose}}{\text{area under the curve, subcutaneous oral dose}}$$

The area under the curve is quantified and used as a measure to determine the relative bioavailability of pharmaceutical compositions and formulations of the invention.

EXAMPLE 5B

Calculation of the Manufacturing Yield for Granules Comprising Enoxaparin

The average manufacturing yields of each granule formulation are indicated in FIG. 3 and vary between 90% and 99%. However, they are slightly lower and are between 88% and 92% for the granules prepared with 2,000 IU of heparin anti-Xa with more significant standard deviations. The manufacturing yield was calculated by quantifying the IU's of heparin anti-Xa recovered from the granules as compared to the IU's used in preparing the same granules.

Figure 6:
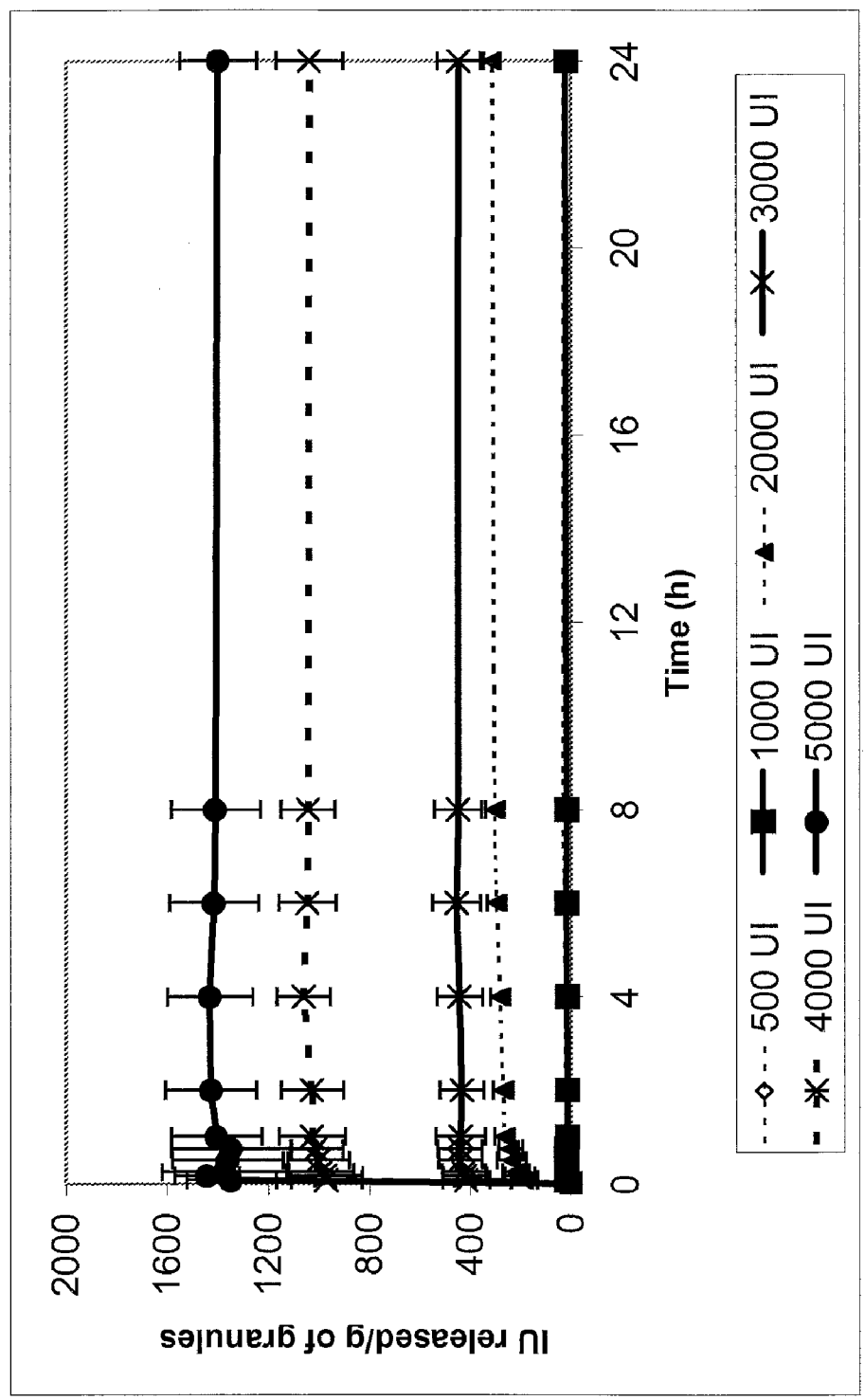
FIG. 6: depicts release profiles for release enoxaparin from primary granules prepared with different quantities of enoxaparin and later mixed with an aqueous suspension containing 100% Eudragit® RS 30 D (n=6± standard deviation).

Furthermore, for the primary granules mixed with Eudragit® RS 30 D, associated or not to Aquacoat® ECD, the lower the initial quantity of enoxaparin used the lower the quantity of heparin released. This result is additionally confirmed by the fact that when 500 or 1,000 units of enoxaparin anti-Xa are used for the primary granules mixed with an aqueous suspension which contains 100% Eudragit® RS 30 D, the release of LMWH further decreases, until reaching zero (FIG. 6).

Whatever the quantity of enoxaparin in the granulates, the release profiles are all characterized by a more or less important immediate release, followed by a plateau. The initial release of enoxaparin may lead to the dissolution of the chains of enoxaparin not fixed on the Eudragit® RS 30 D, this quantity being more important the higher the quantity of enoxaparin in the granulates. Furthermore, the incomplete release of the heparin after 24 hours could be due to the fact that the interactions that bond the enoxaparin to the polymer are strong and, in any case, do not break in our experimental dissolution conditions. These results demonstrate that rising quantities of Eudragit® RS 30 D present in the granulate matrix decrease the quantity of active compound released.

After the oral administration of granules mixed with aqueous suspensions containing 100% Eudragit® RS 30 D, 100% Aquacoat® ECD and a 50/50 mixture of Eudragit® RS 30 D/Aquacoat® ECD, an oral absorption of enoxaparin is observed, which demonstrates that there is no direct correlation between the in vitro and in vivo studies. In effect, the in vitro studies show that the primary granules of MCC only mixed with ethyl cellulose have the best release profile, whilst in vivo these same formulations have very low anti-Xa activities. In contrast, the primary granules of MCC only mixed with Eudragit® RS 30 D have the greatest oral absorption profiles. This last result demonstrates the existence of possible interactions between the positive charges of the quaternary ammonium groups of Eudragit® RS and the negative charges of the intestinal mucosa, thus confirming the mucoadhesive properties of the polyacrylic derivatives (Jiao et al., 2002(c)). The adhesion of the granules on the digestive wall may create a concentration gradient which would facilitate the release of enoxaparin in the proximities of the intestinal mucosa. On the other hand, Eudragit® RS 30 D, polycationic polymer, may perhaps, such as chitosan, favor the opening of the tight bonds, and thus permit the passage of enoxaparin by paracellular route. The presence for its part of MCC on the surface would favor the release of sufficient quantities of active compound, demonstrating that the combined presence of both polymers on the surface balances the necessary relation between affinity for the absorption mucosa and the release of active compound.

These results allow the enoxaparin granules to occupy an interesting place among the group of other strategies which demonstrate the administration of heparins by oral route. These results show a strong potential, which have also been confirmed by the in vivo administration of formulations constituted by a primary granule formed by an aqueous dispersion of Low Molecular Weight Heparins on a MCC core which is subsequently coated by the coating in fluidized bed technique with an organic solution of a mixture of Eudragit® RS PO and Polycaprolactone in a 50/50 proportion.

EXAMPLE 6

In Vivo Studies of Granules with Enoxaparin

Measurement of Anti-Xa Activity

Figure 7:
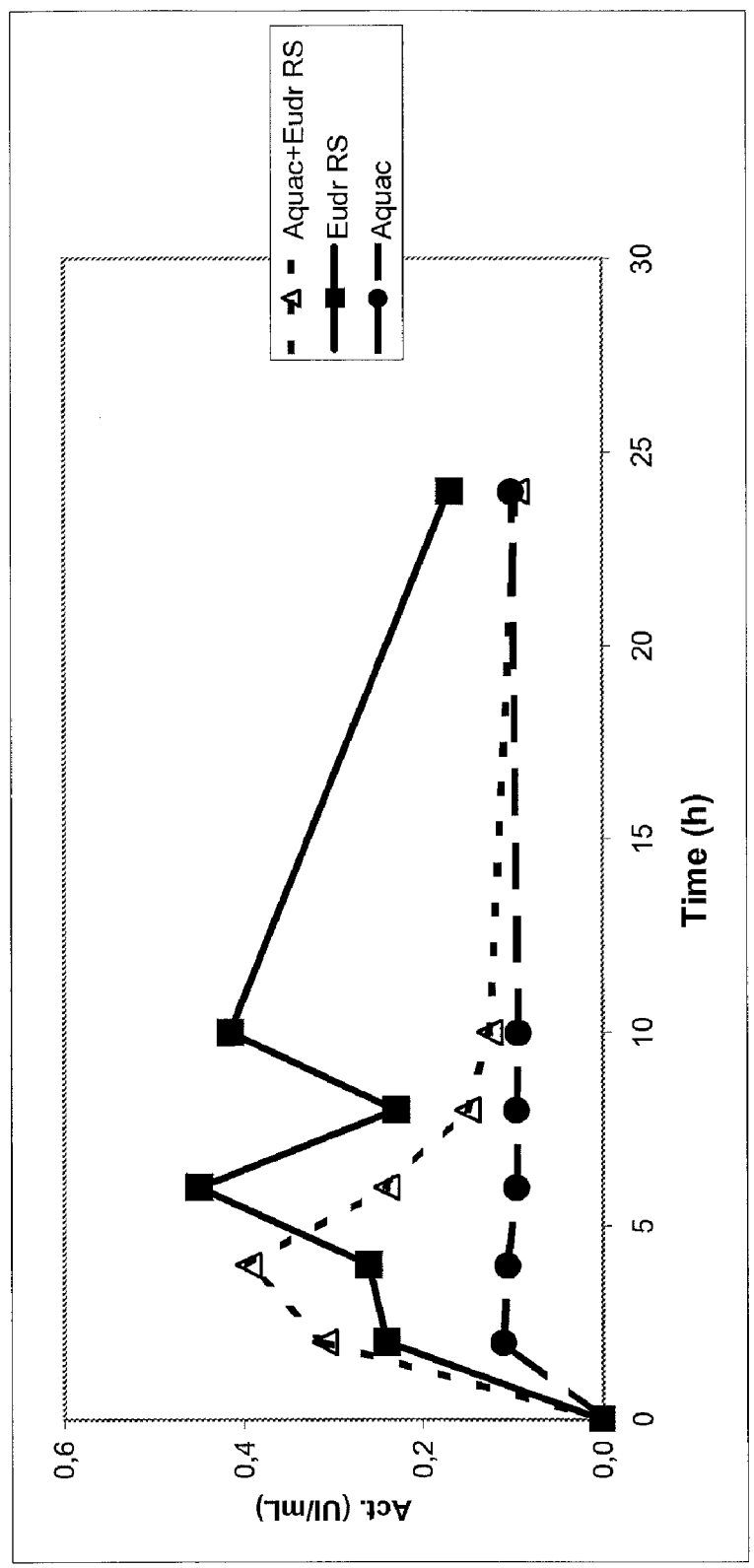
FIG. 7: depicts a plot of the time-dependent Anti-Xa activity per ml in plasma of New Zealand White rabbits after the oral administration of 600 IU anti-Xa/kg enoxaparin granules in gelatine capsules. The groups correspond to MCC cores mixed respectively with a suspension which contains Aquacoat® and Eudragit® RS (Aquac+Eudr RS), a suspension of Eudragit® RS (Eudr RS) and a suspension of Aquacoat® (Aquac) (n=3).

FIG. 7 compares the plasma anti-Xa activities after oral administration to rabbits of enoxaparin granules (600 IU/kg) and after a subcutaneous injection of commercial enoxaparin solution (300 IU/kg). It can be observed that the primary granules of MCC only mixed with ethyl cellulose (Aquacoat) have a very low anti-Xa activity, indeed almost zero. In contrast, the primary granules of MCC only mixed with Eudragit® RS 30 D, which generate the most prolonged activity and the highest values of Cmax (Cmax =0.45 ±0.12 IU of anti-Xa/mL), correspond to a Tmax of 6 hours. The primary granules of MCC mixed with the aqueous suspension of Eudragit® RS and ethyl cellulose in 50/50 proportion lead to a slightly lower Cmax (Cmax =0.4 ±0.12 IU of anti-Xa/mL) corresponding to a Tmax of 4 hours.

Relative Bioavailabilities

After calculating the areas under the curve using the trapezoidal method, the relative bioavailabilities calculated 8 hours after oral administration of the granules have given the following values: 6.1% for the primary granules of MCC only mixed with ethyl cellulose, 17.8% for the primary granules of MCC mixed with Eudragit® RS, and 17.3% for the primary granules of MCC mixed with the Eudragit® RS/ethyl cellulose 50/50 mixture.

Whatever the quantity of enoxaparin in the granulates, the release profiles are all characterized by a more or less important immediate release, followed by a plateau. The initial release of enoxaparin may lead to the dissolution of the chains of enoxaparin not fixed on the Eudragit® RS 30 D, this quantity being more important the higher the quantity of enoxaparin in the granules. Furthermore, the incomplete release of the heparin after 24 hours could be due to the fact that the interactions that bond the enoxaparin to the polymer are strong and, in any case, do not break in our experimental dissolution conditions.

After the oral administration of primary granules of MCC mixed with aqueous suspensions containing 100% Eudragit® RS 30 D, 100% Aquacoat® ECD and a 50/50 mixture of Eudragit® RS 30 D/Aquacoat® ECD, an oral absorption of enoxaparin is observed, which demonstrates that there is no direct correlation between the in vitro and in vivo studies. Indeed, the in vitro studies show that the primary granules of MCC only mixed with ethyl cellulose have the best release profile, whilst in vivo these same formulations have very low anti-Xa activities. In contrast, the primary granules of MCC only mixed with Eudragit® RS 30 D have the greatest oral absorption profiles. This last result demonstrates the existence of possible interactions between the positive charges of the quaternary ammonium groups of Eudragit® RS and the negative charges of the intestinal mucosa, thus confirming the mucoadhesive properties of the polyacrylic derivatives, whilst the cellulose derivative would permit the release of sufficiently high levels of active compound. The adhesion of granulates on the digestive wall may create a concentration gradient which would facilitate the release of enoxaparin in the proximities of the intestinal mucosa. On the other hand, Eudragit® RS 30 D, polycationic polymer, such as chitosan, probably favors the opening of the tight bonds, and thus permits the passage of enoxaparin by paracellular route.

These first results permit the enoxaparin granulates to occupy and interesting place among the group of other strategies which demonstrate the administration of heparins by oral route. These results show a strong potential of the formulations prepared in the present invention.

EXAMPLE 7

Preparation of Granules Containing Tinzaparin

Tinzaparin is a low molecular weight heparin whose antithrombotic and anticoagulant activities are dissociated. It is characterized by higher anti-Xa activity than anti-IIa activity, the proportion between both activities being 1.8.

The form used for our experiments is an aqueous solution of INNOHEP® dosed at 18,000 IU of anti-Xa/0.9 mL and commercially designed for the subcutaneous route.

The polymers used for the creation of the polymeric matrix are:
Cellulose:
In this example its solid form dissolved in acetone at different concentrations has been used.
Poly-ε-Caprolactone (PCL):
PCL is a semicrystalline aliphatic polyester with a molecular mass of 42000 g/mol. It is a biodegradable polymer, for which hydrolysis gives rise to the formation of water soluble monomers which are eliminated in the urine (Chen D R et al. Polycaprolactone microparticles and their biodegradation. Polymer degradation and stability, 2000, 52: 117-126). PCL is insoluble in water and soluble in organic solvents such as acetone. The PCL has been obtained from Sigma-Aldrich.

The processes used for granulation have been the following:

The manufacturing of the granulates is carried out in two stages. The first stage, called primary granulation, consists of mixing the aqueous solution of tinzaparin (5,000 IU of anti-Xa) with 1 g of microcrystalline cellulose (MCC). After drying the mass, the agglomerates are forced to pass through a metal sieve with mesh opening of 600 μm. The primary granulates thus produced are then dried for 5 minutes in the oven at 40° C.

The second stage, of regranulation, consists of adding a solution of Eudragit® RS and PCL in equivalent proportions in acetone (100 mg/ml of each of the two polymers) to the granules. The addition of different quantities of this polymer mixture to the primary granules of cellulose and tinzaparin has been studied. Thus, by varying the volume of organic solution added to the previously produced primary granules, granules have been obtained with quantities of the Eudragit® RS and PCL mixture in quantities of 200, 400, 600 and 800 mg per gram of cellulose. The combination is dried in the oven at 40° C. for 30 minutes. Once dry, the agglomerates are forced to pass through the metal sieve with a mesh opening equal to 600 μm. The granules produced are dried in the oven at 40° C. for 5 minutes.

The proportions of the different polymers thus produced are shown in the following table:

| Formulation | % Cellulose | % Eudragit ® RS | % PCL |
|---|---|---|---|
| 1 | 83.33 | 8.33 | 8.33 |
| 2 | 71.43 | 14.28 | 14.28 |
| 3 | 62.50 | 18.75 | 18.75 |
| 4 | 55.55 | 22.22 | 22.22 |

The "virgin" granules, without heparin, have been prepared in the same manner, substituting the heparin solution for water.

In an alternative regranulation process, a solution of Eudragit® RS in acetone (200 mg/ml) is added to the primary granules. The addition of different quantities of this Eudragit® RS solution to the primary granules of cellulose and tinzaparin has been studied. Thus, by varying the volume of organic solution added to the previously produced primary granules, granules have been obtained with quantities of Eudragit® RS in quantities of 200, 400, 600 and 800 mg per gram of cellulose. The combination is dried in the oven at 40° C. for 30 minutes. Once dry, the agglomerates are forced to pass through the metal screen with a mesh opening equal to 600 μm. The granules produced are dried in the oven at 40° C. for 5 minutes.

The proportions of the different polymers thus produced are shown in the following table:

| Formulation | % Cellulose | % Eudragit ® RS |
|---|---|---|
| 5 | 83.33 | 16.66 |
| 6 | 71.43 | 28.57 |
| 7 | 62.50 | 37.50 |
| 8 | 55.55 | 44.44 |

The "virgin" (control) granules, without heparin, have been prepared in the same manner, substituting the heparin solution for water.
Characterization of the Granules Produced:
Morphology and Size The particle size of the granules has been determined by the laser diffraction technique in a Malvern Mastersizer apparatus. The primary granules are resuspended in pH 7.4 phosphate buffer. During the measurement, the suspension is maintained by stifling the measuring basin.

Figure 8B:
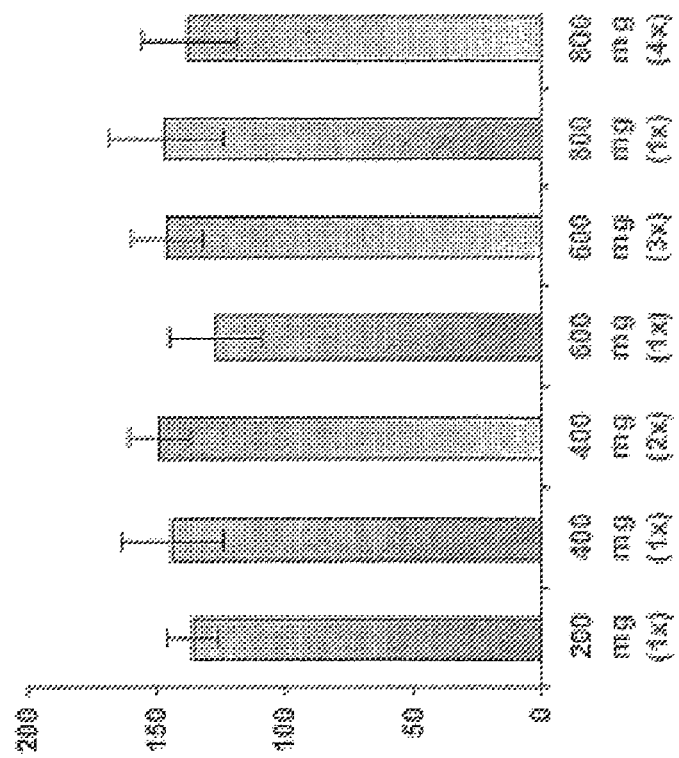
FIGS. 8A-8B: depict plots of the average size of the granules produced by addition of Eudragit® RS (FIG. 8A) or by the addition of Eudragit® RS and PCL in equivalent quantities (FIG. 8B) (n=3± standard deviation). (1×) corresponds to the quantity added in one stage. (2×) corresponds to the quantity added in two stages of 200 mg of polymers (in the case of Eudragit® RS and PCL mixture) or polymer (in the case of the addition of Eudragit® RS alone) each. (3×) corresponds to the quantity added in three stages of 200 mg each. (4×) corresponds to the quantity added in four stages of 200 mg each. This example demonstrates how particles that are functionally equivalent can be obtained by adding the polymers in a single or multiple step process.
Figure 8A:
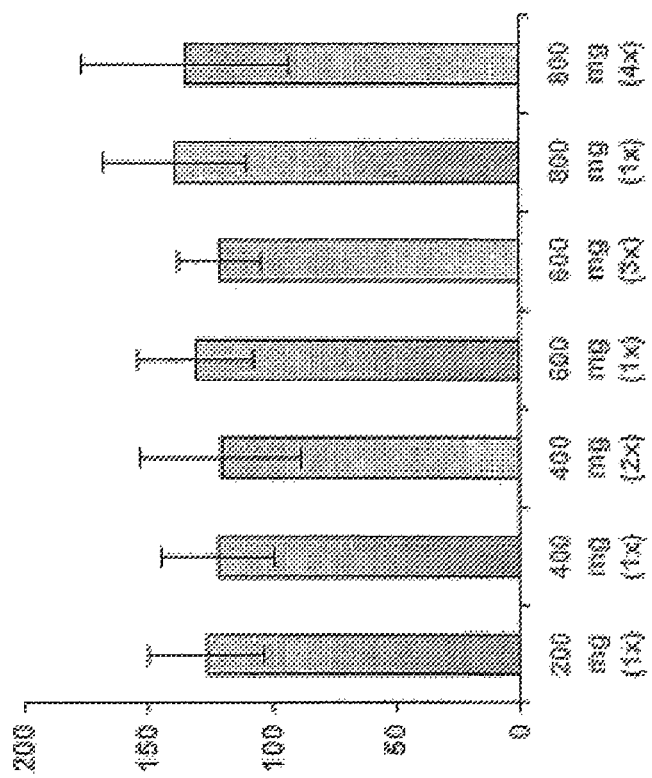
Figure 10A:
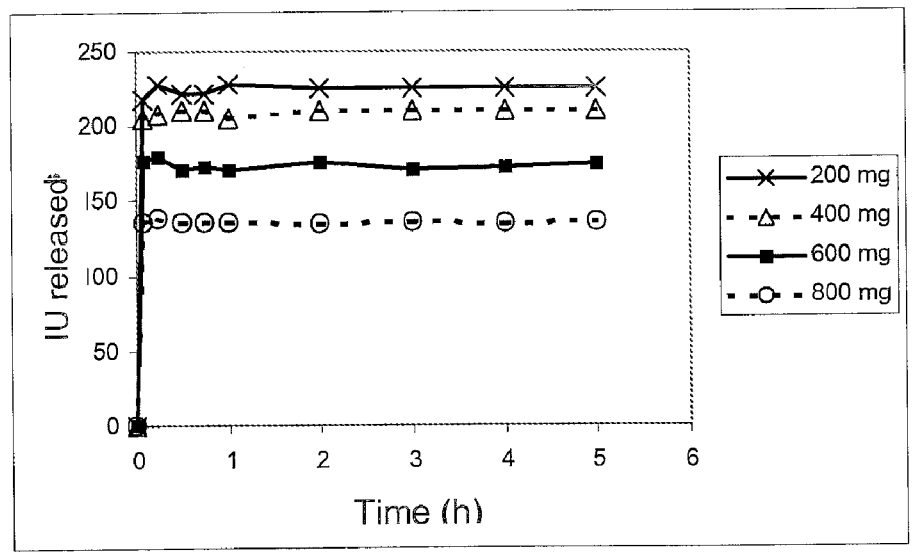
FIGS. 10A-10B: depict release profiles for the release of tinzaparin from primary granules mixed with different quantities of Eudragit® RS and PCL dissolved in acetone (n=3). The graph on the left (FIG. 10A) corresponds to the addition of Eudragit® and PLC in a single stage, and the graph on the right (FIG. 10B) corresponds to the addition of the polymer mixture in stages of 200 mg each.
Figure 10B:
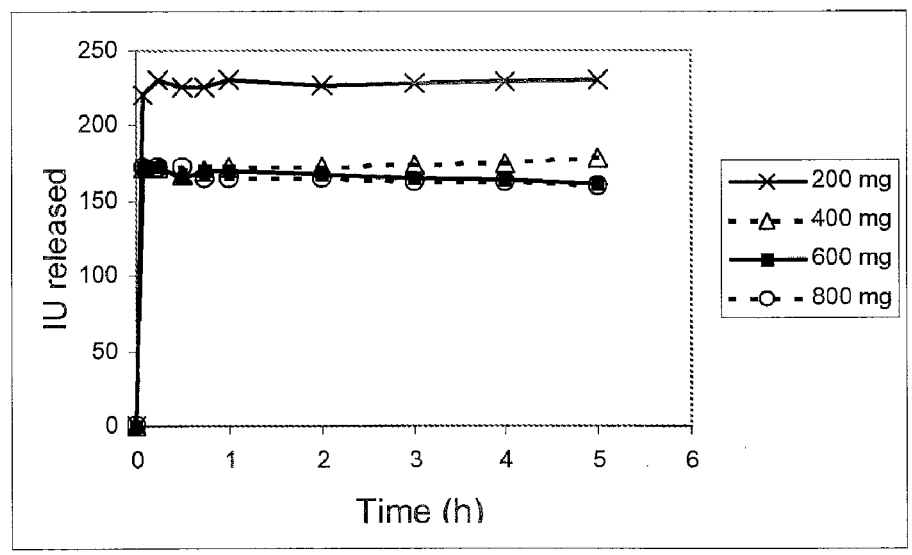

The average size of the granules produced has been in all cases between 100 and 150 μm as depicted in FIG. 8.
In Vitro Release Kinetics The objective of this assay is to determine the quantity of tinzaparin released by the granules over time. This in vitro release should be performed in defined conditions called "sink", i.e. those wherein the maximum concentration of active compound which can be released in a release medium is less than 30% of the saturation concentration, so that the concentration gradient can be considered non-limiting.

The release assays have been carried out in a water bath thermostatted at 37° C., suspending with gentle magnetic stirring (300 rpm) 50 mg of each batch of tinzaparin granules in 20 mL of phosphate buffer (PBS, 0.011 M and NaCl, 0.15 M) at pH 7.4 containing 0.1% Tween 80.

1 mL samples were taken with the automatic pipette after 5, 10, 15, 30, 45 minutes, and after 1, 2, 3, 4, 5, 6, 7, 8 and 24 hours. The volumes collected were substituted by 1 mL of fresh buffer in order to maintain a constant volume in the flasks. These aliquots were then filtered with a MILLIPORE filter with 0.22 μm porosity.

The quantities of tinzaparin released were evaluated by nephelometry, and then the curves which represent the release kinetics of tinzaparin in accordance with time are established. The release kinetics were performed in triplicate for each of the samples (n=3). The results are shown in FIGS. 9A-9B and FIGS. 10A-10B.

The granules produced have a two-phase release profile, with a rapid initial release followed by a sustained release. As can be seen in FIGS. 9A-9B and FIGS. 10A-10B, a greater quantity of polymers added to the primary core reduces the release of the tinzaparin contained therein. This fact also occurs both in the primary granules mixed with Eudragit® RS as well as in those mixed with the Eudragit® RS and PCL solution, and in both it is certainly related to the increase in interaction between tinzaparin and Eudragit® RS.

EXAMPLE 8

In Vivo Studies of Granules with Tinzaparin

Measurement of the Anti-Xa Activity

Figure 11:
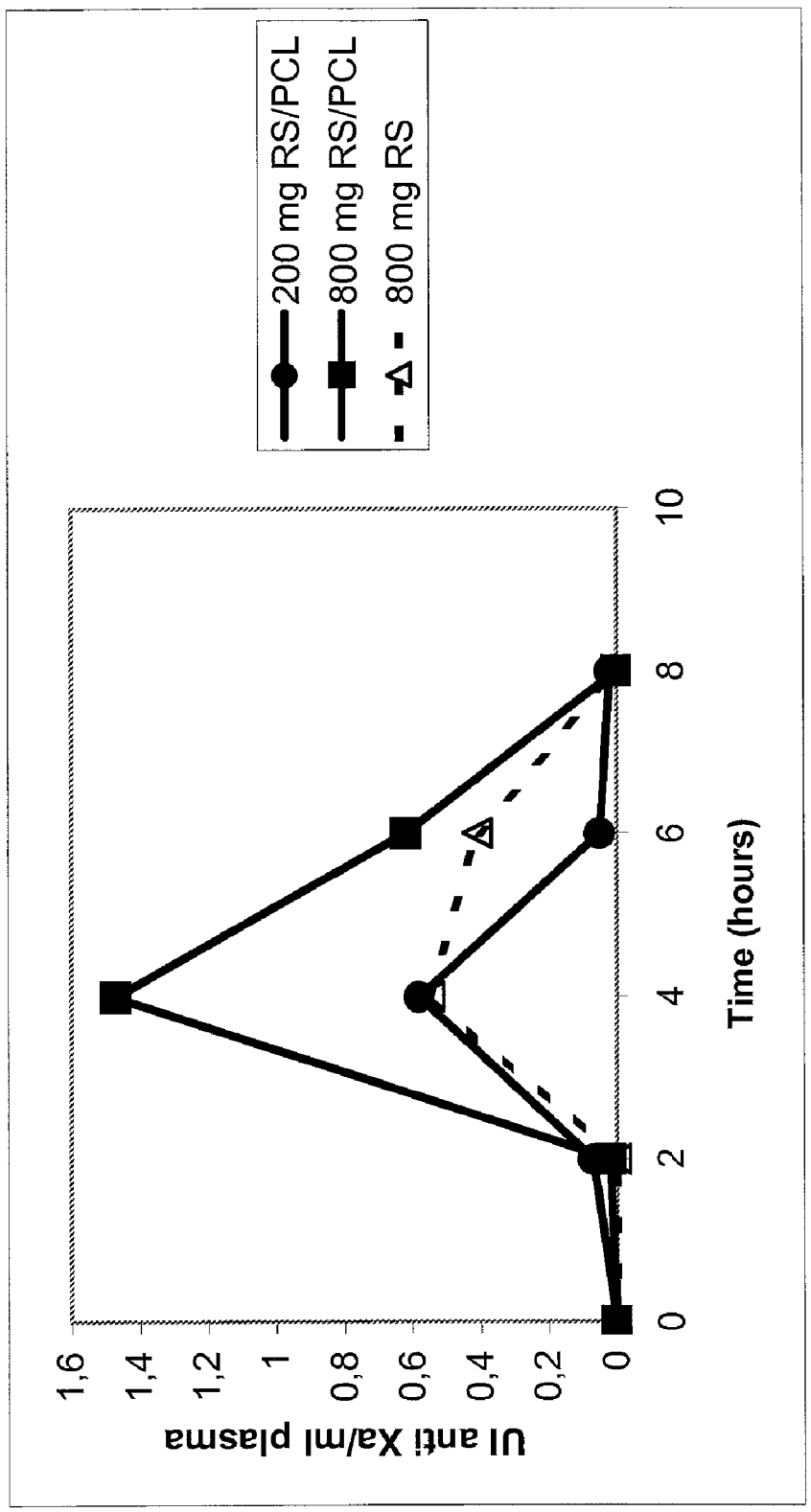
FIG. 11: depicts a plot of the time-dependent Anti-Xa activity per ml in plasma of New Zealand White rabbits after the oral administration of 600 IU anti-Xa/kg of tinzaparin granules in gelatine capsules. Two groups correspond to primary granules of MCC with tinzaparin mixed respectively with 200 and 800 mg of a Eudragit® RS and PCL solution in acetone (200mg RS/PCL and 800mg RS/PCL) and the third group corresponds to primary granules of MCC with tinzaparin mixed with 800 mg of Eudragit® RS (n=3).

FIG. 11 compares plasma anti-Xa activity after the oral administration to rabbits of granules with tinzaparin (600 IU/kg). It has been observed that the primary granules of MCC mixed with 800 mg of Eudragit® RS and PCL in equivalent quantities generate a much higher tinzaparin absorption than that obtained with the primary granules mixed with 200 mg of the Eudragit® RS and PCL solution. In light of these results, the increase in the percentage of Eudragit® RS polycation with respect to the presence of polymers with a negative or neutral charge (8.33% in the formulation wherein 200 mg are added and more than 22% in the formulation wherein 800 mg are added) is clearly demonstrated. This increase in absorption is shown through a higher Cmax value (1.58 compared with 0.57 IU anti-Xa/ml) as well as through an increase in the area under the curve and the bioavailability (F=28.26 compared with F=15.46). As can be clearly observed, the increase in bioavailability is not related to a greater quantity of active compound released from the formulations, since the formulations constituted by primary granules of MCC which are mixed with 200 mg of the Eudragit® RS and PCL polymeric solution release more tinzaparin and at a greater rate than the formulations that are mixed with 800 mg of the Eudragit® RS and PCL solution.

The in vivo assay demonstrates that tinzaparin, normally not absorbable after its oral administration in the form of solution, is absorbed in significantly high quantities when it is administered in the form of granules when they have a suitable composition. The increasing quantities of Eudragit® RS favor a greater interaction of the granule with the intestinal wall and mainly with the negatively charged mucosa that covers it, whilst the presence of the biodegradable polyester, PCL, favors the in vivo release of tinzaparin in suitable quantities. This hypothesis is supported by the fact that the primary granules mixed with 800 mg of Eudragit® RS and PCL have a greater absorption profile than the primary granules of MCC which are mixed with 800 mg of Eudragit® RS.

EXAMPLE 9

Preparation of Granules Containing Bemiparin

Bemiparin is a low molecular weight heparin whose antithrombotic and anticoagulant activities are dissociated. It is characterized by higher anti-Xa activity than anti-IIa activity, the proportion between both activities being between 2 and 4.

The form used for our experiments is an aqueous Bemiparin solution starting from lyophilized Bemiparin (ROVI laboratories) dosed at 5,000 IU of anti-Xa/mL.

The manufacturing of the granules is carried out in two stages. The first stage, called primary granulation, consists of mixing the aqueous Bemiparin solution (5,000 IU of anti-Xa in 1 ml) with 1 g of microcrystalline cellulose (MCC). After drying the mass, the agglomerates are forced to pass through a metal sieve with mesh opening of 600 μm. The primary granules thus produced are then dried for 5 minutes in the oven at 40° C.

The second stage, of regranulation, consists of adding an aqueous dispersion of Eudragit® RS (Eudragit® RS 30 D) to the primary granules. The combination is dried in the oven at 40° C. for 30 minutes. Once dry, the agglomerates are forced to pass through the metal sieve with a mesh opening equal to 600 μm. The granules produced are dried in the oven at 40° C. for 5 minutes.

The proportions of the different polymers thus produced are shown in the following table:

| Formulation | % Cellulose | % Eudragit ® RS |
|---|---|---|
| 1 | 55.55 | 44.44 |

Characterization of the Granules Produced:
Morphology and Size

The particle size of the granules has been determined by laser diffraction technique in a Malvern Mastersizer apparatus. The granules are first resuspended in pH 7.4 phosphate buffer. During the measurement, the suspension is maintained by stifling the measuring basin.

The average size of the granules produced is of around 150 μm.

In Vivo Studies of Granules with Bemiparin
Measurement of the Anti-Xa Activity

Figure 12:
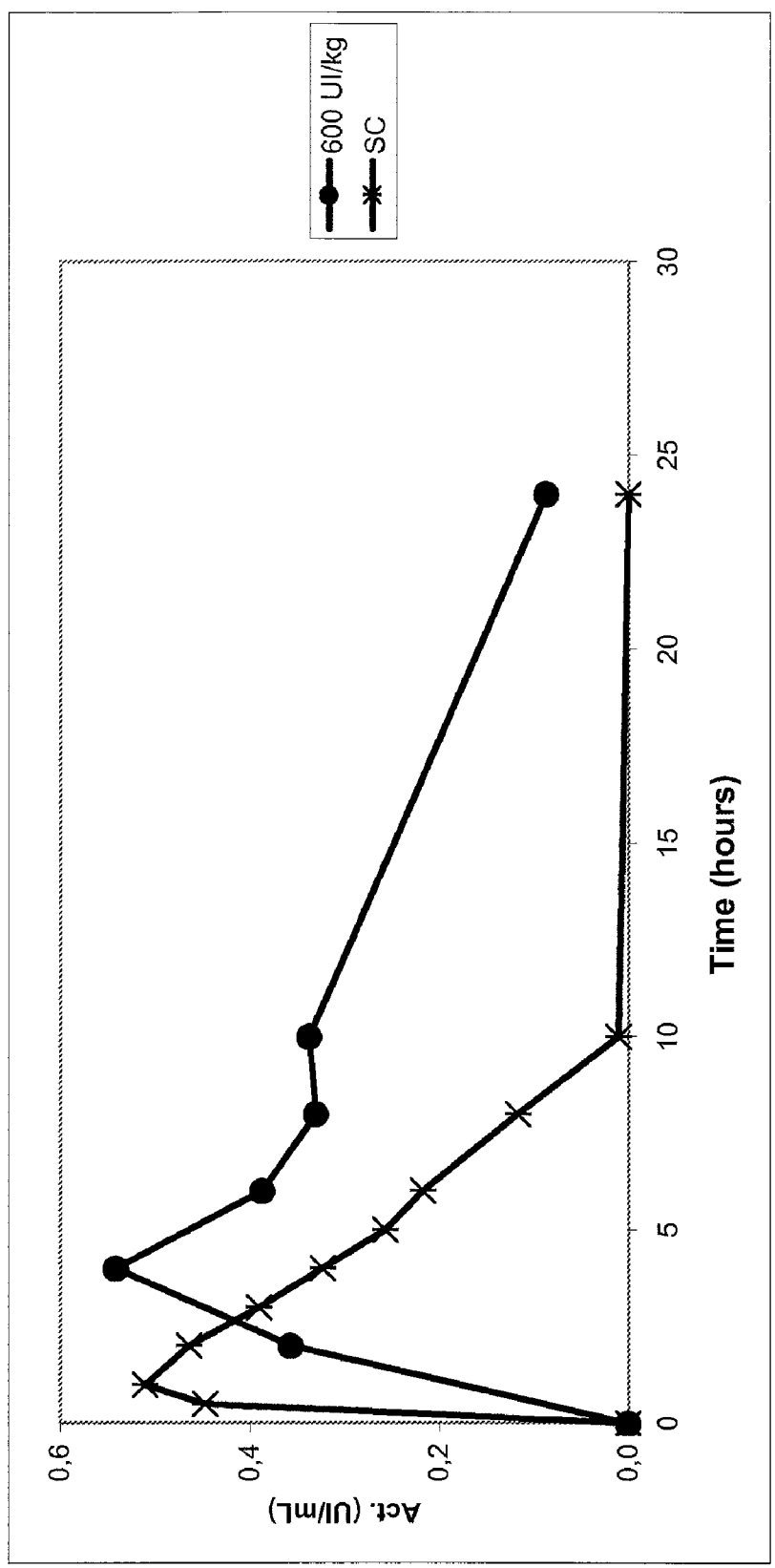
FIG. 12: depicts a plot of the time-dependent Anti-Xa activity per ml in plasma of New Zealand White rabbits after the oral administration of 600 IU anti-Xa/kg of bemiparin granules in gelatine capsules. SC corresponds to the administration of 150 IU/kg of Bemiparin dissolved in 1 ml of distilled water by subcutaneous route (n=3).

FIG. 12 compares the plasma anti-Xa activities after the oral administration to rabbits of granules with bemiparin at a dose of 600 IU/kg. Similarly to that produced with enoxaparin and tinzaparin granules, the granules containing Bemiparin give rise to significantly high plasma levels. The bioavailability relative to the subcutaneous administration of Bemiparin dissolved in water at a dose of 150 IU/kg was 60.94%, and the Cmax of 0.54 IU/ml in plasma after 4 hours.

EXAMPLE 10

Preparation of Pellets Containing Enoxaparin

The form used for the experiments is an aqueous solution of LOVENOX® dosed at 10,000 IU of anti-Xa/mL and commercially designed for the subcutaneous route.

The following table shows the composition of the pellets in percentage with respect to the final solid mass. Likewise, the quantity of water used in the preparation of the pellets is included in the table by way of illustration:

| Eudragit ® RS 30D[a] | Acetyltriethylcitrate plasticizer | MCC | Lactose | Enoxaparin sodium[a, b] |
|---|---|---|---|---|
| 20.76% | 0.4% | 55.23% | 21.10% | 2.51% |

Comments:
[a]Calculated as mass of the solid
[b]LOVENOX ®: Enoxaparin sodium at a concentration of 10000 IU/ml
Eudragit ® RS 30D dispersion - 69.20 g, of which 20.76 g correspond to the dry mass of the polymer and 48.44 g correspond to the liquid phase
Enoxaparin solution (LOVENOX) - 24.03 g, of which 2.51 g correspond to dry enoxaparin and 21.52 g correspond to water First, the MCC, the lactose and the plasticizer are mixed for 2 minutes in a mixer (Tefal Kaleo, France). Then the Eudragit® RS dispersion at a flow of 10 ml/min and the aqueous solution of enoxaparin are gradually added, subjecting the combination to homogenization for 1 minute. The mass produced is extruded through 0.6 mm pores (thickness of the extruded mass is 1 mm) and subsequently it is spheronized for 15 minutes at 640 rpm. The resulting pellets are dried in a ventilated oven at 40° C. during 48 hours.

The granules thus produced contain 25.1 mg of Enoxaparin per gram of pellets.

Despite the fact that all components of the pellet are homogeneously distributed throughout the formulation, the proportion of polymers that form the matrix and, therefore, are on the surface is significantly high (55.23% of MCC and 20.76% of Eudragit® RS). Their non-presence in greater quantity is probably the cause that the bioavailability obtained is not at the level of the granules, as it will become apparent below.

Characterization of the Pellets Produced:

Morphology and Size

The particle size of the pellets produced has been determined by optical microscope. The procedure permits preparing pellets with diameters between 0.5 and 1.2 mm. For the in vitro and in vivo assays, the mass of pellets is sieved to separate them into two portions with sizes comprised between 0.5-0.8 mm and 0.8-1.2 mm.

In Vitro Release Kinetics

The objective of this assay is to determine the quantity of enoxaparin released by the pellets over time. This in vitro release should be performed under defined conditions called "sink", i.e. those wherein the maximum concentration of active compound which can be released in a release medium is lower than 30% of the saturation concentration, so that the concentration gradient can be considered non-limiting.

The release assays have been carried out in a bath thermostatted at 37° C., suspending with gentle magnetic stirring (300 rpm) 50 mg of each batch of enoxaparin pellets in 20 mL of phosphate buffer (PBS, 0.011 M and NaCl, 0.15 M) at pH 7.4, containing 0.1% of Tween 80.

1 mL samples have been taken with the automatic pipette after 5, 15, and 30 minutes, and after 1, 2, 4 and 24 hours. The volumes collected are substituted by 1 mL of new buffer in order to maintain a constant volume in the flasks. These aliquots are then filtered with a MILLIPORE filter with 0.22 µm porosity.

The quantities of enoxaparin released are evaluated by nephelometry, and then the curves which represent the release kinetics of enoxaparin as a function of time are established. The release kinetics have been performed in triplicate for each one of the samples (n=3).

The pellets produced have a two-phase release profile, with a rapid initial release followed by a sustained release. As can be seen in FIGS. 13A and 13B, no relevant differences are observed in relation to the release rate of the active compound in accordance with the pellet size, in all cases quickly releasing the enoxaparin.

EXAMPLE 11

In Vivo Studies of Pellets with Enoxaparin

Measurement of the Anti-Xa Activity

Figure 14:
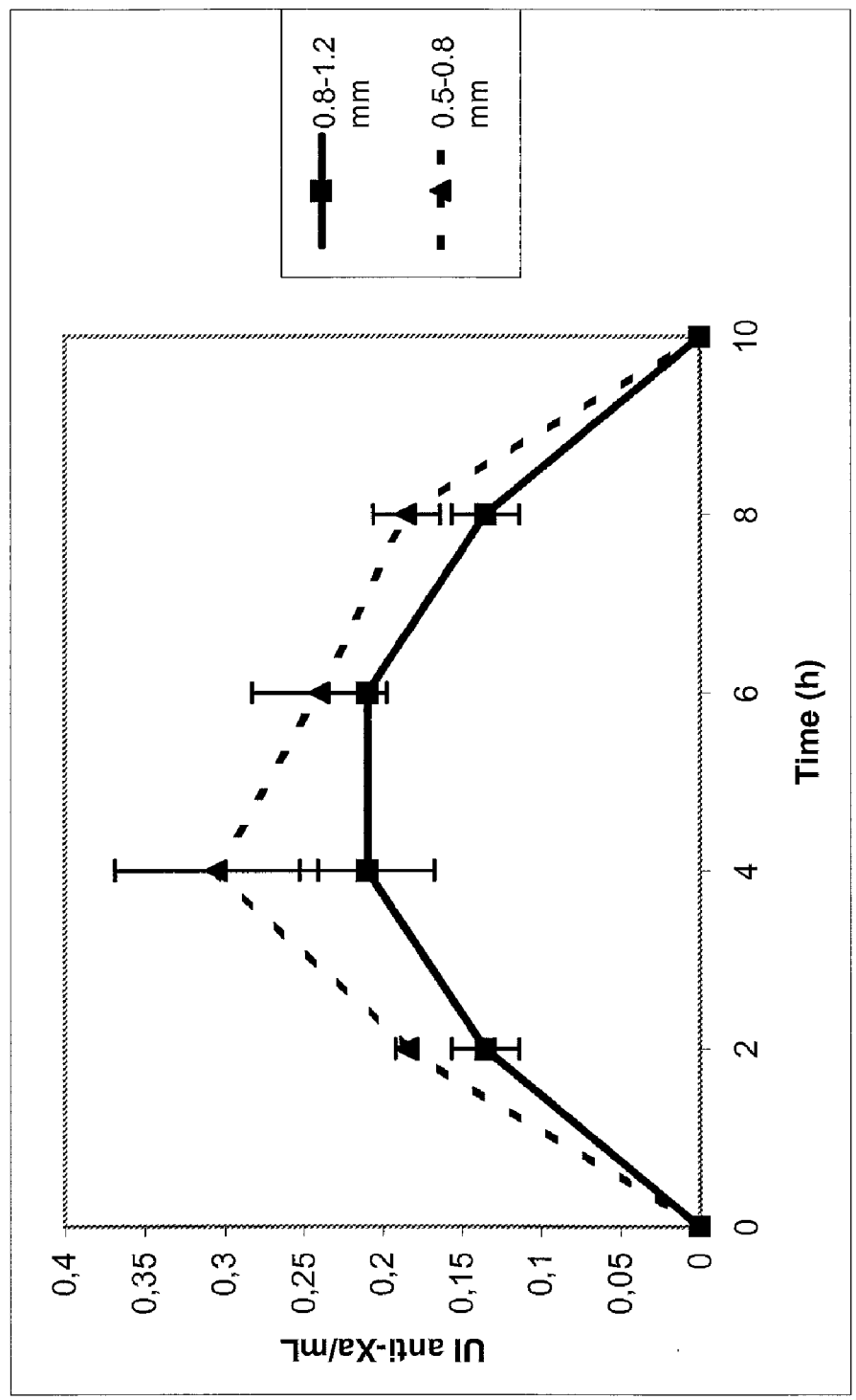
FIG. 14: depicts a plot of the time-dependent Anti-Xa activity per ml in plasma of New Zealand White rabbits after the oral administration of 600 IU anti-Xa/kg of enoxaparin pellets in gelatin capsules. One group corresponds to pellets with an average diameter between 0.5 and 0.8 mm and another group corresponds to pellets with an average diameter between 0.8 and 1.2 mm (n=3 ± standard deviation).

FIG. 14 compares the plasma anti-Xa activities after the oral administration to rabbits of pellets with enoxaparin (600 III/kg). As it can be observed in the figure, the oral administration to NZW rabbits of the pellets, with sizes between 0.5-0.8 mm and 0.8-1.2 mm provide significantly high absorptions, with plasma levels which are maintained over a period of 10 hours. The Cmax obtained with pellets of size between 0.5 and 0.8 mm is 0.305 IU/ml after 4 hours, whilst that obtained with pellets of size between 0.8 and 1.2 mm is 0.21 IU/ml after 4-6 hours. The values of absolute bioavailability obtained are respectively 13.7% for pellets of size Between 0.5-0.8 mm and 10.4% for pellets of size between 0.8-1.2 mm. Despite the fact that the pellets of smaller size provide greater bioavailability than the larger ones, it is surprising to obtain bioavailabilities of this magnitude with such large particles.

This in vivo assay demonstrates that the appropriate use of polymers in the preparation of formulations permits achieving the absorption of enoxaparin in significant quantities after its administration by oral route. The combined effect of a sufficient adhesion to the mucosal wall and an efficient release of the active compound provided by Eudragit® RS and Microcrystalline cellulose is sufficiently significant to permit active compounds poorly permeable to the absorption barrier to pass through it, despite the large size of the pellets which may exceed the millimeter in diameter. This observation is surprising in light of the information that may be found today in the state of the art, which continually stresses the need to reduce the formulation size to produce more efficient dispersions with a greater contact time with the absorption mucosa. It is also obvious for a person skilled in the art that the formulations included in the examples herein have further undeniable advantages over the production of microparticles and nanoparticles, since they are produced by processes commonly used in the pharmaceutical industry, they have less variability in interbatch production and are easily scalable to industrial batches, unlike what happens with other formulations.

EXAMPLE 12

Formation of Coated Granules Containing Bemiparin

The manufacturing of the granules is carried out in two stages. The first stage, called core preparation, consists of preparing primary bemiparin granules with microcrystalline cellulose (MCC). A high-speed Zanchetta Rotolab® granulator/mixer has been used to prepare the granules.

Composition:

| Avicel pH 101 | 100 g | 95.24% |
|---|---|---|
| Bemiparin | 5 g | 4.76% |
| Water milli-Q | q.s. | |

Preparation Procedure:
1. Dissolve the Bemiparin in 50 mL of milli-Q water and place it in the dropping funnel.
2. Weigh the exact quantity of avicel and place it in the granulator container.
3. Add the Bemiparin solution to the avicel in movement due to the drive blade
4. Check the degree of wetting of the avicel and the formation of granules.
5. Add the necessary quantity of milli-Q water until the granules are formed.
6. Remove the granules from the equipment and sieve them through a sieve with a mesh opening of 1 mm.
7. Dry in oven at 37° C. for 2 hours and then at ambient temperature.

Equipment Conditions:

| Speed of the impeller (drive blade) | 250-300 rpm |
|---|---|
| Chopper | Off |
| Heating jacket | Off |

The second stage, of coating, consists of adding a polymer mixture to the primary granules, either dissolved or in suspension, by spraying of the primary cores in fluidized bed (Mini Glatt® with microkit accessory). The primary granules are then coated directly with different proportions of each of the polymers.

Composition:

| Coating solution: | Eudragit ® RS PO | 2.5 g |
|---|---|---|
| | PCL | 2.5 g |
| | Acetone | 100 mL |

To perform the coating of the previously produced primary granules, we introduce 30 grams thereof in the granulator to coat them with the aforementioned coating solution wherein both polymers are in a 1:1 ratio. Granules have been prepared with different coating percentages (2.5, 4 and 8% w/w in relation to the initial mass of primary granules introduced). The same concentration of solids has been used in all of them, 5% by weight with respect to the acetone volume, and the greater or lesser degree of coating is achieved by varying the solution volume used to coat the primary granule.

Preparation Procedure:

1. Place the inner core (30 g) in the product filling tubulator of the fluidized bed
2. Fill the hose with the coating solution until the spray nozzle.
3. Switch on the equipment and adjust the process parameters
4. Perform the coating and remove the end product from the tubulator.

Process Parameters:

| Temperature (° C.) | Pump index | Air pressure of the process (bars) | Spray air pressure (bars) | Air temperature of the process (° C.) |
|---|---|---|---|---|
| Ambient | 1.0 | 0.08-0.15 | 0.50 | 25 |

Once the spraying of the polymeric solution has concluded, the process air is maintained during 20 seconds for the coating to dry.

Characterization of the Granules Produced:
Morphology and Size

Figure 15:
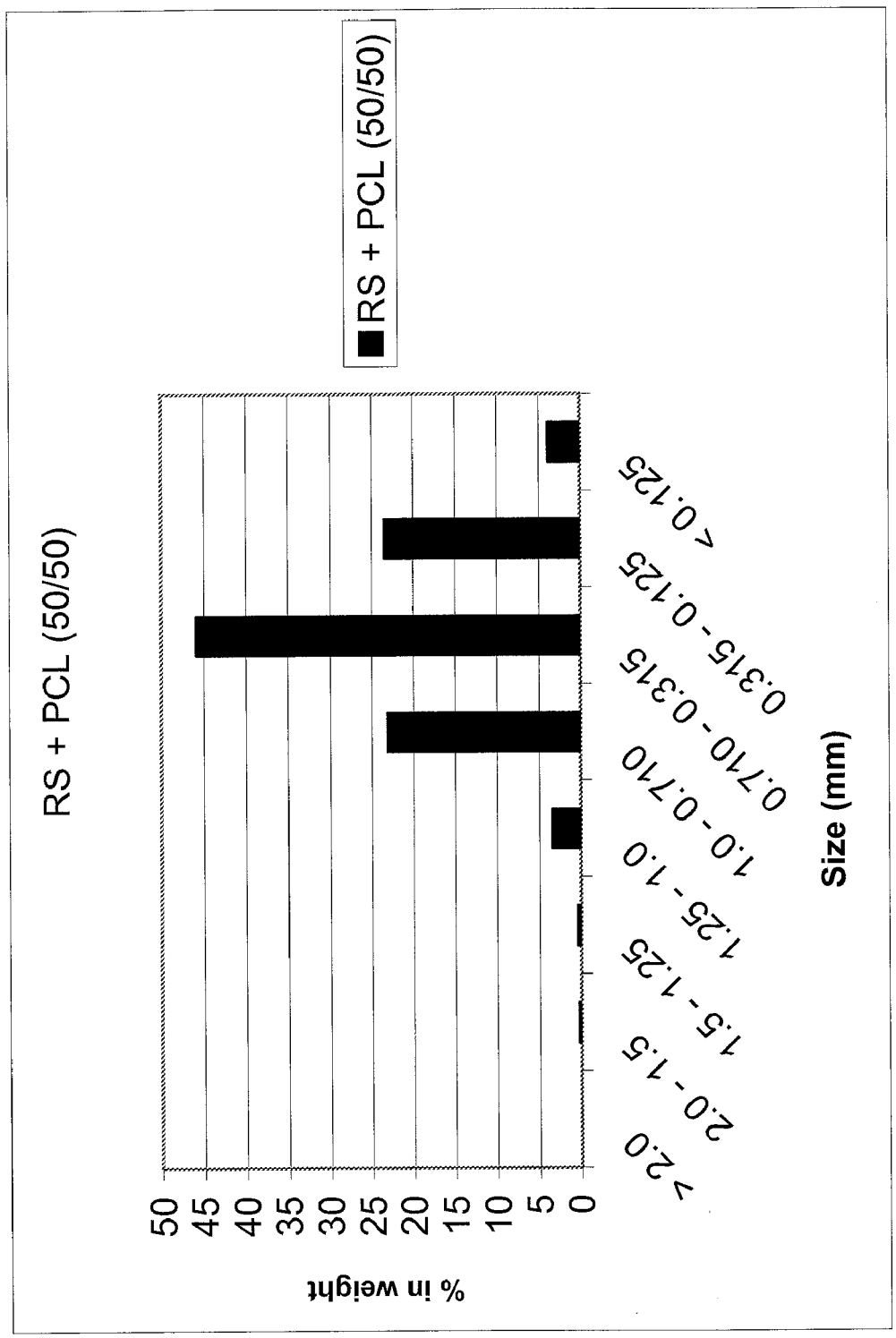
FIG. 15: depicts a plot of the particle size distribution of the granules provided by the invention. The bars represent the percentage (%) by mass of the different fractions obtained after the sieving process based upon the total mass of the particles.

The granulates coated with the Eudragit® RS and PCL matrix, the coating representing a gain of 4% over the weight of the primary MCC and Bemiparin granule, have been observed under the optical microscope in these conditions and after having been dispersed in a 4% PVA solution. The size has been determined by separation by sieving, using sieves with mesh openings of 2, 1.5, 1.25, 1, 0.71, 0.315 and 0.125 mm. The result is expressed in percentage of the total mass measured which the different fractions obtained represent. The distribution of sizes obtained can be observed in FIG. 15.

As can be observed in the figure, 72.82% of total mass of the granulates have a particle size over 0.315 mm, the main fraction being that which has a size between 0.71 and 0.315 mm, which constitutes 45.85% of the total mass of the granulate.

In Vitro Release Kinetics

The release assays have been performed in sink conditions in a 6-vessel dissolution apparatus with water bath thermostatted at 37° C. 166 mg of granules produced (with 4% coating) have been introduced in a hard number 1 gelatine capsule and the capsules have been introduced in spinner baskets which are immersed in the dissolution medium (400 ml of pH 6.8 phosphate buffer). The spinner basket rotation rate has been maintained at 100 rpm.

1.5 mL samples have been taken with the automatic pipette after 30 minutes, and after 1, 1.5, 2, 4, 6 and 24 hours. The volumes collected are substituted by 1.5 mL of new buffer in order to maintain a constant volume in the vessels. These aliquots are then filtered with a MILLIPORE filter with 0.22 μm porosity.

The quantities of bemiparin released are evaluated by nephelometry, and then the curves which represent the release kinetics of bemiparin as a function of time are established. The release kinetics have been performed in duplicate for each one of the samples (n=2).

Figure 16:
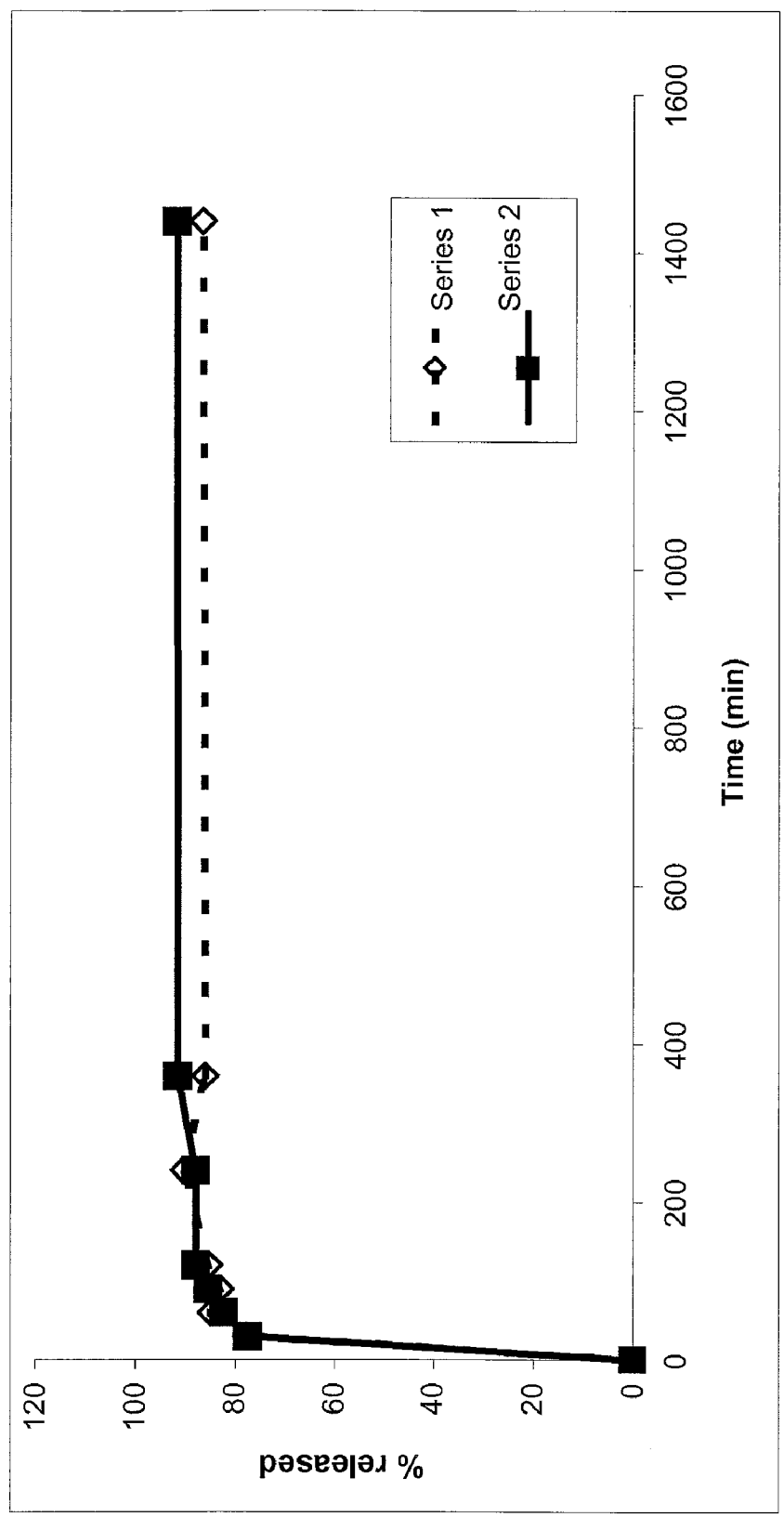
FIG. 16: depicts a release profile for the release of Bemiparin from the granules of the invention. The figure represents the percentage (%) of Bemiparin released over the total as a function of time. The dissolution medium is phosphate buffer at pH 6.8 (n=2; series 1 and 2).

As can be observed in FIG. 16, the release profile is two-phase, similar to that produced with the granules prepared by mixing. In the two measurements made the percentages released after an hour exceed 80% of the total incorporated. In this case it can be observed that the quantity of Eudragit® RS and PCL is very low in the granule with respect to that incorporated in the formulations produced by mixing. Nevertheless, the polymeric coating containing the Eudragit® RS and PCL matrix is capable of releasing the active compound in a similar way to that produced with the previous formulations. Despite the fact that certain retention of Bemiparin in the granule is observed, probably due to its interaction with the cationic polymer, the quantity of active compound is sufficient for it to be released in significantly high quantities.

EXAMPLE 13

In Vivo Studies of Granules with Bemiparin

Measurement of the Anti-Xa Activity

Figure 17:
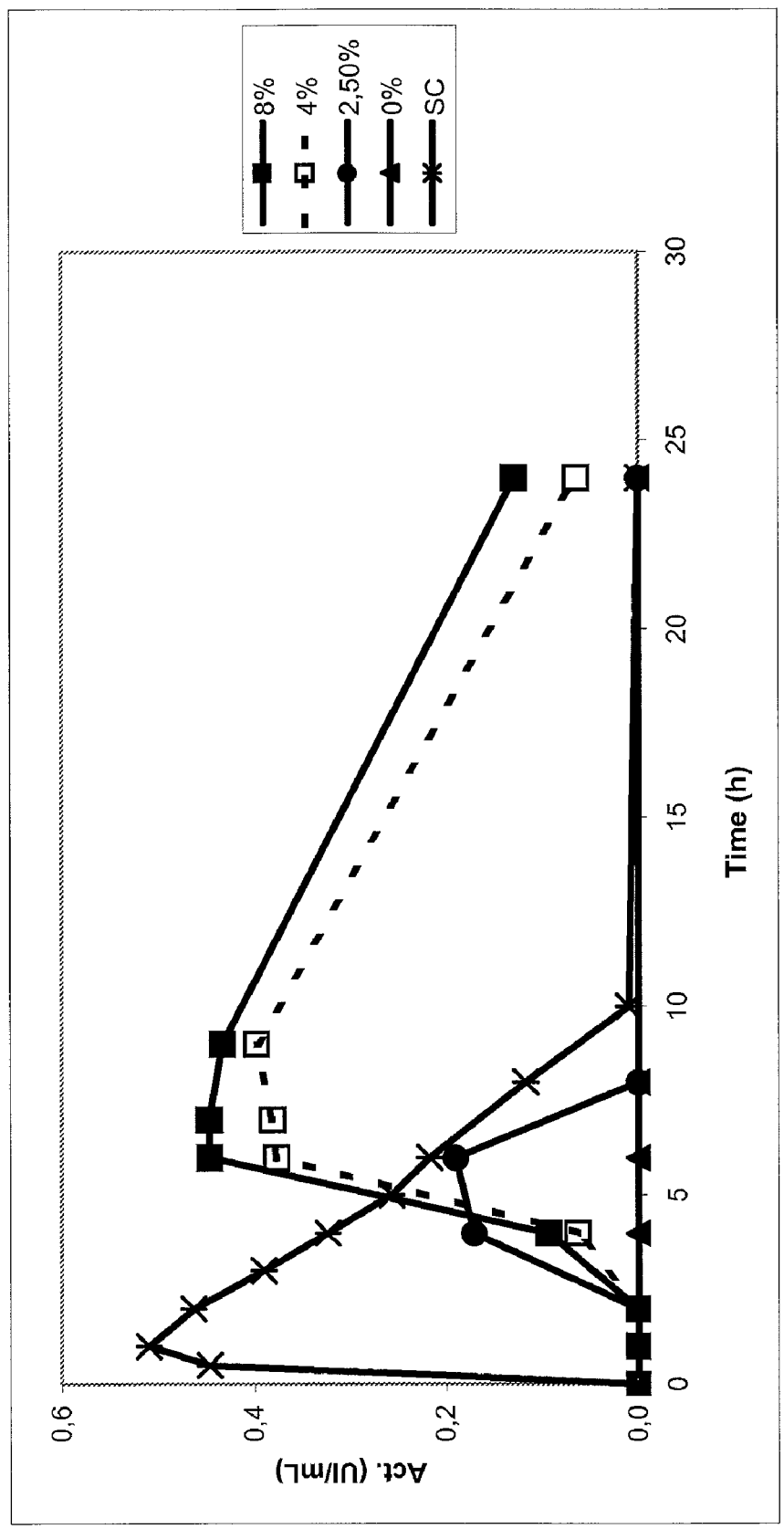
FIG. 17: depicts a plot of the time-dependent Anti-Xa activity per ml in plasma of New Zealand White rabbits after the oral administration of 600 IU anti-Xa/kg bemiparin granules in gelatine capsules. The groups correspond to granules with percentages of coating of the polymer mixture of 8, 4 and 2.5% respectively (n=3). 0% corresponds to the administration of primary granules (uncoated) in hard gelatine capsules at a dose of 600 IU/kg. SC corresponds to the administration of 150 IU/kg of Bemiparin dissolved in 1 ml of distilled water by subcutaneous route (n=3).

FIG. 17 compares the plasma anti-Xa activities after the oral administration to rabbits of hard gelatine capsules (with enteric coating of Eudragit® L) containing Bemiparin granules produced according to example 12 (600 IU/kg). As can be observed in the figure, the polymeric coating plays an extremely important role in the biological activity of the administered formulations, since the oral administration of bemiparin in uncoated MCC granules does not cause the appearance of plasma levels of the active compound. Likewise, a clear influence is observed of the coating thickness in the biological activity of the granules produced. Despite the fact that the coating of the primary granule with a 2.5% weight gain of the mixture of Eudragit® RS and PCL gives rise to the presence of detectable plasma levels, probably the quantity of coating added is not sufficient to completely coat primary granulate. However, additions of the polymer mixture which represent a weight gain of 4 and 8% provide high absorptions, with plasma levels which are maintained for a 24-hour period. The Values of Cmax and the relative bioavailabilities obtained for each one of these formulations are reflected in the following table.

| % coating | Cmax | F(%) relative to 150 IU/kg sc |
|---|---|---|
| 0 | 0 | 0 |
| 2.5 | 0.90 | 5.58 |
| 4 | 0.3978 | 39.59 |
| 8 | 0.447 | 47.66 |

It is important to highlight that in these examples Eudragit® RS and the PCL are found in equivalent quantities on the surface. The combined effect of a sufficient adhesion to the mucosal wall and an efficient release of the active compound provided by Eudragit® RS and PLC is sufficiently important to permit active compounds poorly permeable to the absorption barrier to pass through it.

For the purposes of clarifying the results obtained and demonstrating the activity achieved with the suitable polymeric material, the incorporation of excipients commonly used in granulation procedures has been avoided intentionally (both for the core and for the coating) but it is also obvious for a person skilled in the art that this preparation procedure can also be performed using any of the excipients that may be required to optimize the granulation process.

Additionally, anti-Xa activity has been studied in the plasma of NZW rabbits after the oral administration of 600 IU/kg of bemiparin granules prepared according to the procedure described in example 18 with a 5% coating on non-enteric gelatine capsules.

Figure 18:
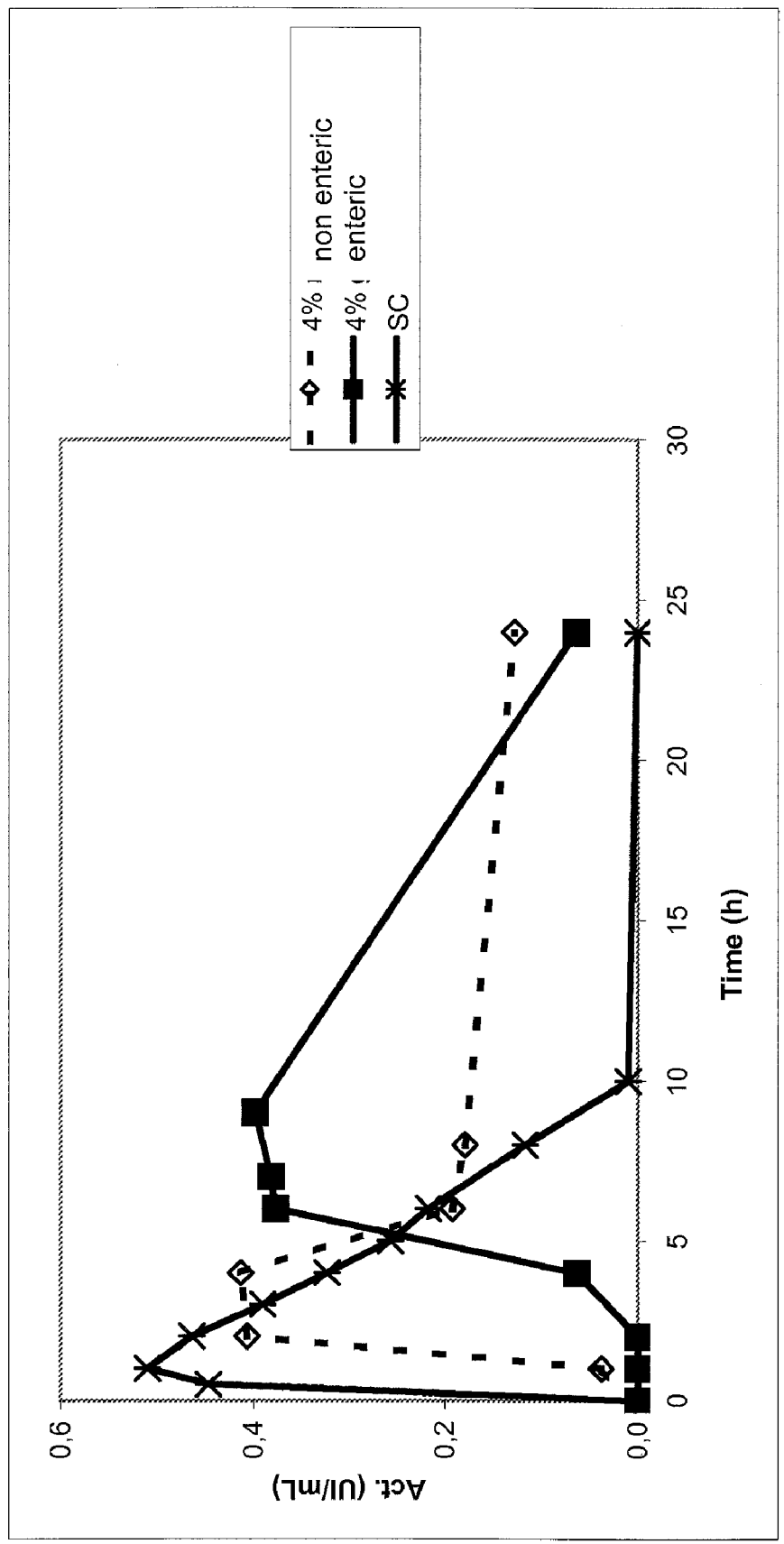
FIG. 18: depicts a plot of the time-dependent Anti-Xa activity per ml in plasma of New Zealand White rabbits after the oral administration of 600 IU anti-Xa/kg bemiparin granules in gelatine capsules. The groups correspond to granules with percentages of coating of the polymer mixture of 4% which are incorporated respectively in non-enteric and enteric gelatine capsules (n=3). SC corresponds to the administration of 150 IU/kg of Bemiparin dissolved in 1 ml of distilled water by subcutaneous route (n=3).

As can be seen in FIG. 18, the enteric coating modifies the kinetic profile obtained only in relation to the appearance time of the anti-Xa activity plasma levels, but neither the Cmax obtained nor the bioavailability significantly vary with the use of enteric coatings in the gelatine capsules. Therefore, it is sufficiently demonstrated that the absorption of bemiparin obtained is not related to the release of formulations in the intestinal tract, but the formulations enable the absorption of bemiparin after a single oral administration. The delay observed in the appearance of plasma levels in the case of the enteric capsules is directly related to the time necessary for the capsule to pass through the digestive cavity and to start to disintegrate in a suitable pH environment in the duodenum.

EXAMPLE 14

Formation of Coated Granules Containing Bemiparin

The manufacturing of the granules is carried out in two stages. The first stage, called core preparation, consists of preparing primary bemiparin granules with microcrystalline cellulose (MCC). A high-speed Zanchetta Rotolab® granulator/mixer has been used to prepare the granules.
Composition:

| Avicel pH 101 | 100 g | 95.24% |
|---|---|---|
| Bemiparin | 5 g | 4.76% |
| Water milli-Q | q.s. | |

Preparation Procedure:
1. Dissolve the Bemiparin in 50 mL of milli-Q water and place it in the dropping funnel.
2. Weigh the exact quantity of avicel and place it in the granulator container.
3. Add the Bemiparin solution to the avicel in movement due to the drive blade
4. Check the degree of wetting of the avicel and the formation of granulate.
5. Add the necessary quantity of milli-Q water until the granulate is formed.
6. Remove the granulate from the equipment and sieve it through a sieve with a mesh opening of 1 mm.
7. Dry in oven at 37° C. for 2 hours and then at ambient temperature.

Equipment Conditions:

| Speed of the impeller (drive blade) | 250-300 rpm |
|---|---|
| Chopper | Off |
| Heating jacket | Off |

The second stage, of coating, consists of adding a polymer mixture to the primary granulates, either dissolved or in suspension, by spraying of the primary cores in fluidized bed (Mini Glatt® with microkit accessory). The primary granulates are then coated directly with different proportions of each of the polymers.
Composition:

| Coating solution: | Eudragit ® RS PO | 4.5 g |
|---|---|---|
| | PCL | 0.5 g |
| | Acetone | 100 mL |

To perform the coating of the previously produced primary granules, 30 grams thereof are introduced in the granulator to coat them with the aforementioned coating solution wherein the Eudragit® RS PO: PCL ratio is 9:1. Granules have been prepared with a coating percentage of 5% w/w in relation to the initial mass of the primary granules introduced.
Preparation Procedure:
1. Place the inner core (30 g) in the product filling tubulator of the fluidized bed
2. Fill the hose with the coating solution until the spray nozzle.
3. Switch the equipment on and adjust the process parameters
4. Perform the coating and remove the end product from the tubulator.

Process Parameters:

| Temperature (° C.) | Pump index | Air pressure of the process (bars) | Spray air pressure (bars) | Air temperature of the process (° C.) |
|---|---|---|---|---|
| Ambient | 1.0 | 0.08-0.15 | 0.50 | 25 |

Figure 19:
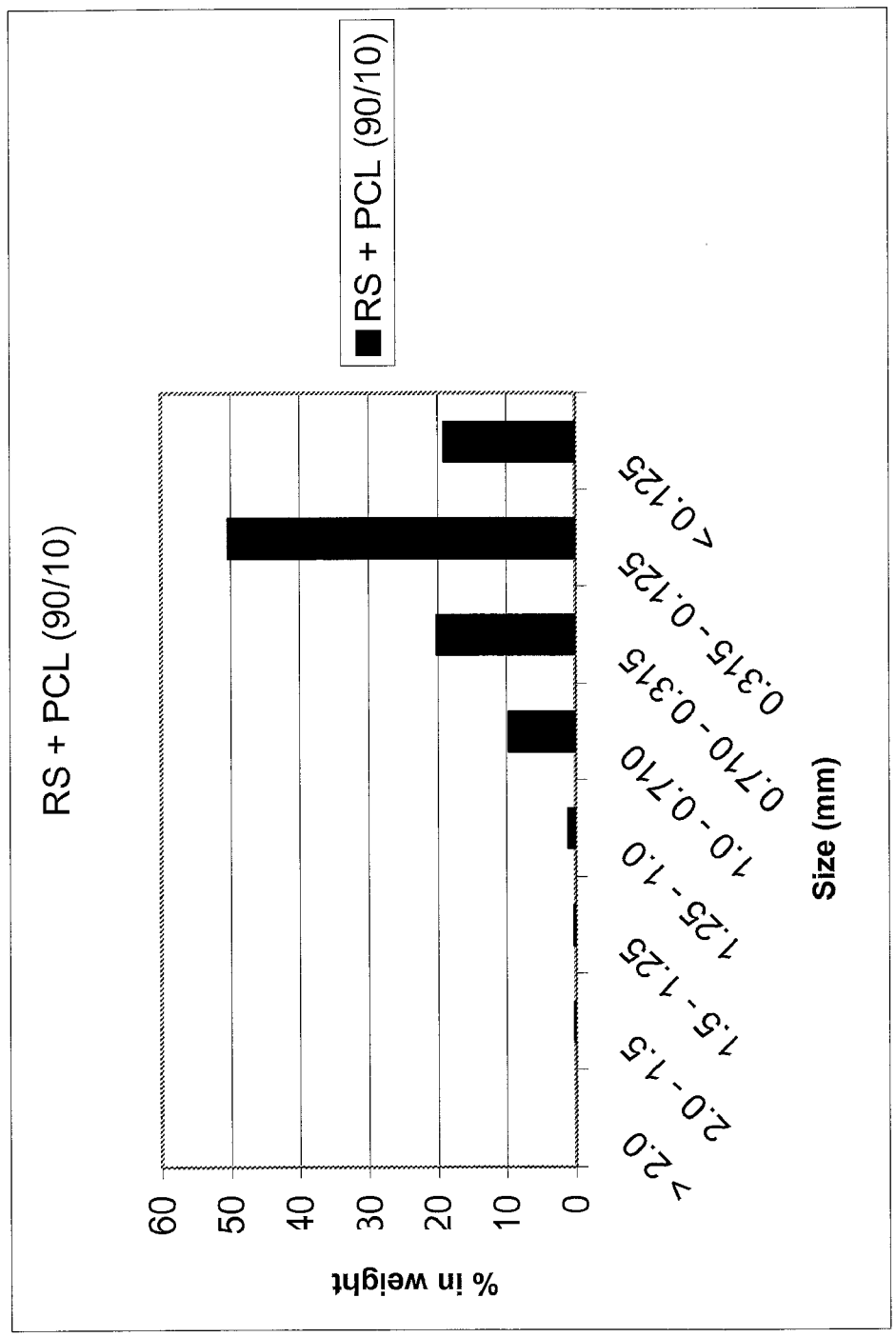
FIG. 19: depicts a plot of the particle size distribution for granules produced according to the invention. The bars represent the percentage (%) by mass of the different fractions obtained after the sieving process.

Once the spraying of the polymeric solution has concluded, the process air is maintained during 20 seconds for the coating to dry.
Characterization of the Granules Produced:
Morphology and Size The granulate coated with the Eudragit® RS and PCL matrix (in 9:1 ratio), the coating representing a gain of 4% over the weight of the primary MCC and Bemiparin granule, have been observed under the optical microscope in these conditions and after having been dispersed in a 4% PVA solution. The size has been determined by separation by sieving, using sieves with mesh openings of 2, 1.5, 1.25, 1, 0.71, 0.315 and 0.125 mm. The result is expressed in percentage of the total mass measured which the different fractions obtained represent. The distribution of sizes obtained can be observed in FIG. 19.

As can be observed in the figure, the resulting particle size is smaller when a 1:1 ratio is used between the Eudragit® RS and the PCL present in the coating. A 50.30% of the total mass of the granules has a particle size between 0.315 mm and 0.125 mm.

EXAMPLE 15

In Vivo Studies of Granules with Bemiparin of Example 14

Measurement of the Anti-Xa Activity

Figure 20:
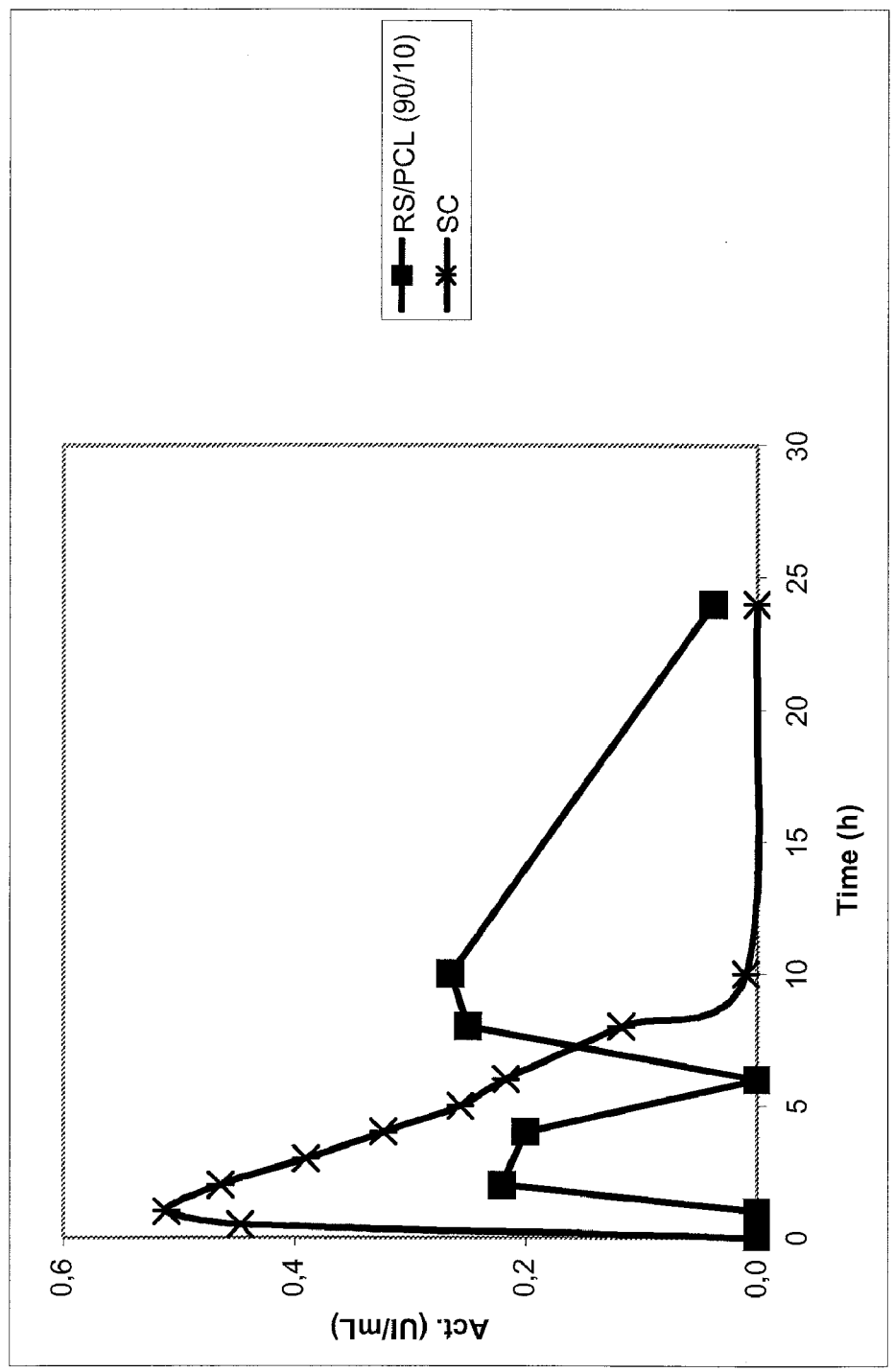
FIG. 20: depicts a plot of the time-dependent Anti-Xa activity per ml in plasma of New Zealand White rabbits after the oral administration of 600 IU anti-Xa/kg of bemiparin granules in gelatine capsules. The groups correspond to granules coated with a mixture of Eudragit® RS and PCL in 9:1 proportion (n=3). SC corresponds to the administration of 150 IU/kg of Bemiparin dissolved in 1 ml of distilled water by subcutaneous route (n=3).

FIG. 20 compares the plasma anti-Xa activities after the oral administration to rabbits of hard gelatine capsules (with enteric coating of Eudragit® L) containing Bemiparin granules produced according to example 14 (600 IU/kg). As can be observed in the figure, the increase of the proportion of Eudragit® RS on the surface up to a ratio of 9:1 in relation to the PCL gives rise to clearly lower levels of plasma activity than those obtained with the administration of granules which have equivalent surface quantities of Eudragit® RS and PCL. However, significantly high absorptions can still be reached in this ratio. The greater presence of Eudragit® RS and the greater interaction produced with the Bemiparin contained in the granule conditions the release of the active compound and, therefore, the absorption thereof, despite the greater bioadhesiveness this polymer gives to the formulation. Values of Cmax and the relative bioavailabilities obtained are reflected in the following table.

| % coating | Cmax | F(%) relative to 150 IU/kg sc |
|---|---|---|
| 5 | 0.265 | 25.37 |

EXAMPLE 16

Formation of Coated Granules Containing Bemiparin and Having an Intermediate Coating Layer The formulations included in this example aim to demonstrate the possibility of adding subcoats with polymers between the primary core and the outer coating with the Eudragit® RS and PCL polymer mixture to avoid contact between the active compound and the polymers that enable the absorption thereof without the activity of the polymeric coating as promoter of Bemiparin absorption varying significantly. The manufacturing of granulates is carried out in three stages. The first stage, called core preparation, consists of preparing primary bemiparin granules with microcrystalline cellulose (MCC). A high-speed Zanchetta Rotolab® granulator/mixer has been used to prepare the granules.

Composition:

| Avicel pH 101 | 100 g | 95.24% |
|---|---|---|
| Bemiparin | 5 g | 4.76% |
| Water milli-Q | q.s. | |

Preparation Procedure:
1. Dissolve the Bemiparin in 50 mL of milli-Q water and place it in the dropping funnel.
2. Weigh the exact quantity of avicel and place it in the granulator container.
3. Add the Bemiparin solution to the avicel in movement due to the drive blade
4. Check the degree of wetting of the avicel and the formation of granulate.
5. Add the necessary quantity of milli-Q water until the granulate is formed.
6. Remove the granulate from the equipment and sieve them through a sieve with a mesh opening of 1 mm.
7. Dry in oven at 37° C. for 2 hours and then at ambient temperature.

Equipment Conditions:

| Speed of the impeller (drive blade) | 250-300 rpm |
|---|---|
| Chopper | Off |
| Heating jacket | Off |

The second stage, of subcoat, consists of adding a polymer mixture to the primary granules, either dissolved or in suspension, by spraying of the primary cores in fluidized bed (Mini Glatt® with microkit accessory). The primary granules are then coated directly with the polymer until obtaining a weight gain of 4%.

Composition:

| Coating solution: | Eudragit ® L | 5 g |
|---|---|---|
| | Acetone | 100 mL |

To perform the coating of the previously produced primary granules, 30 grams thereof are introduced in the granulator to coat them with the aforementioned subcoat solution.

Preparation Procedure:
1. Place the inner core (30 g) in the product filling tubulator of the fluidized bed
2. Fill the hose with the coating solution up to the spray nozzle.
3. Switch the equipment on and adjust the process parameters
4. Perform the coating and remove the end product from the tubulator.

Process Parameters:

| Temperature (° C.) | Pump index | Air pressure of the process (bars) | Spray air pressure (bars) | Air temperature of the process (° C.) |
|---|---|---|---|---|
| Ambient | 1.0 | 0.08-0.15 | 0.50 | 25 |

Once the spraying of the polymeric solution has concluded, the process air is maintained during 20 seconds for the coating to dry.

The third stage, of coating, consists of adding to the primary granules a polymeric coating containing Eudragit® RS PO and PCL in a proportion of 1:1, by spraying of the cores produced in the second step in a fluidized bed (Mini Glatt® with microkit accessory). The granulates with subcoat are then directly coated with the polymer mixture until obtaining a weight gain of 4%. The coating procedure and parameters are identical to those of the subcoating stages.

Characterization of the Granules Produced:

Morphology and Size

The granules coated with the Eudragit® RS and PCL matrix and with a subcoat of Eudragit® L on the primary MCC and Bemiparin granule have been observed under the optical microscope in these conditions and after having been dispersed in a 4% PVA solution. The size has been determined by separation by sieving, using sieves with mesh openings of 2, 1.5, 1.25, 1, 0.71, 0.315 and 0.125 mm. The result is expressed in percentage of the total mass measured which the different fractions obtained represent. The distribution of sizes obtained can be observed in FIG. 21.

Figure 21:
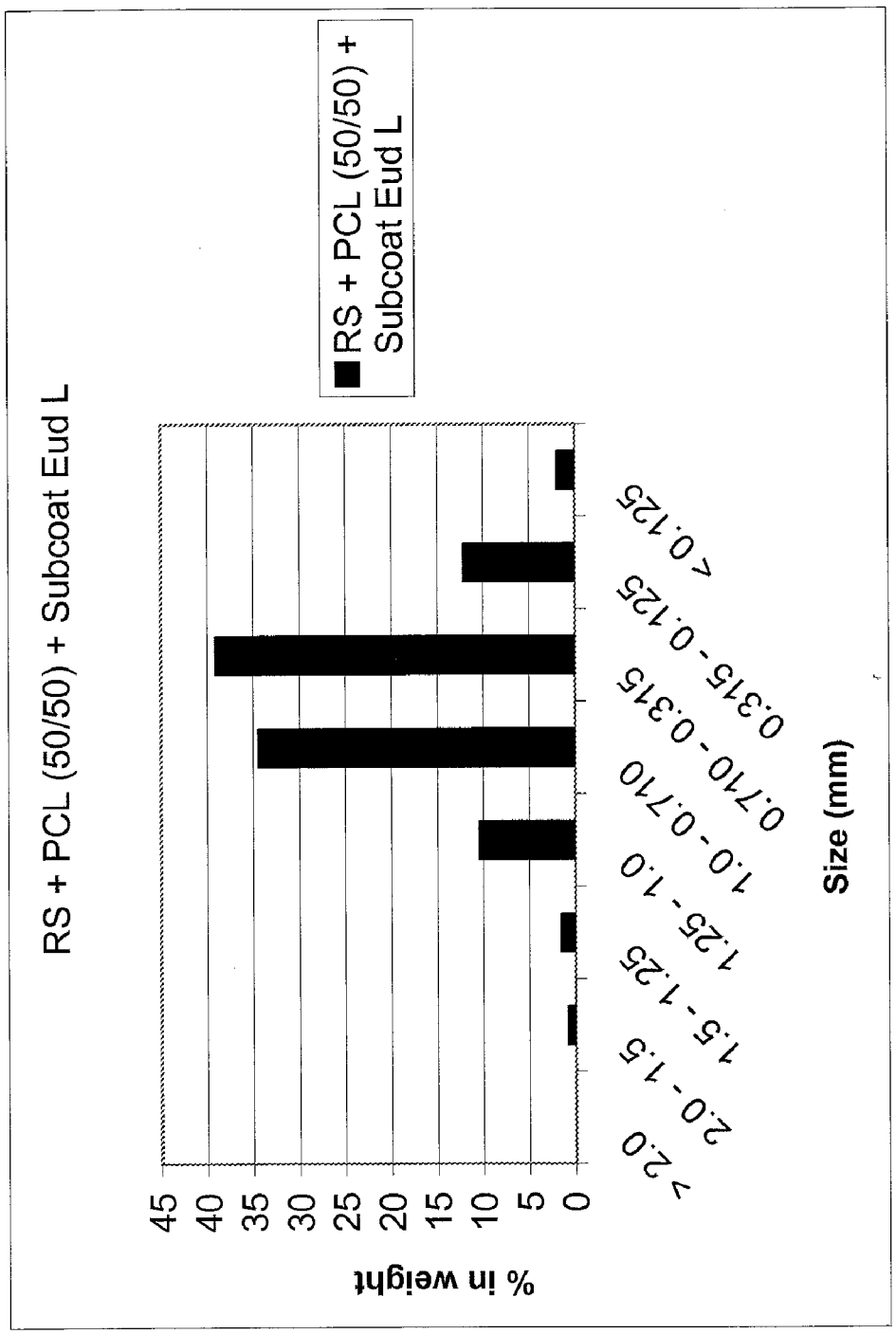
FIG. 21: depicts a plot of the particle size distribution of granules produced according to the invention. The bars represent the % by mass of the different fractions obtained after the sieving process.

As can be observed in FIG. 21, the addition of a subcoat increases the particle size of the granules produced, the fraction which has a particle size over 0.315 mm being 86.10% of the total mass of the granules. The main fraction is that which represents particles between 0.71 and 0.315 mm, with 39.01% of the total.

EXAMPLE 17

Figure 22:
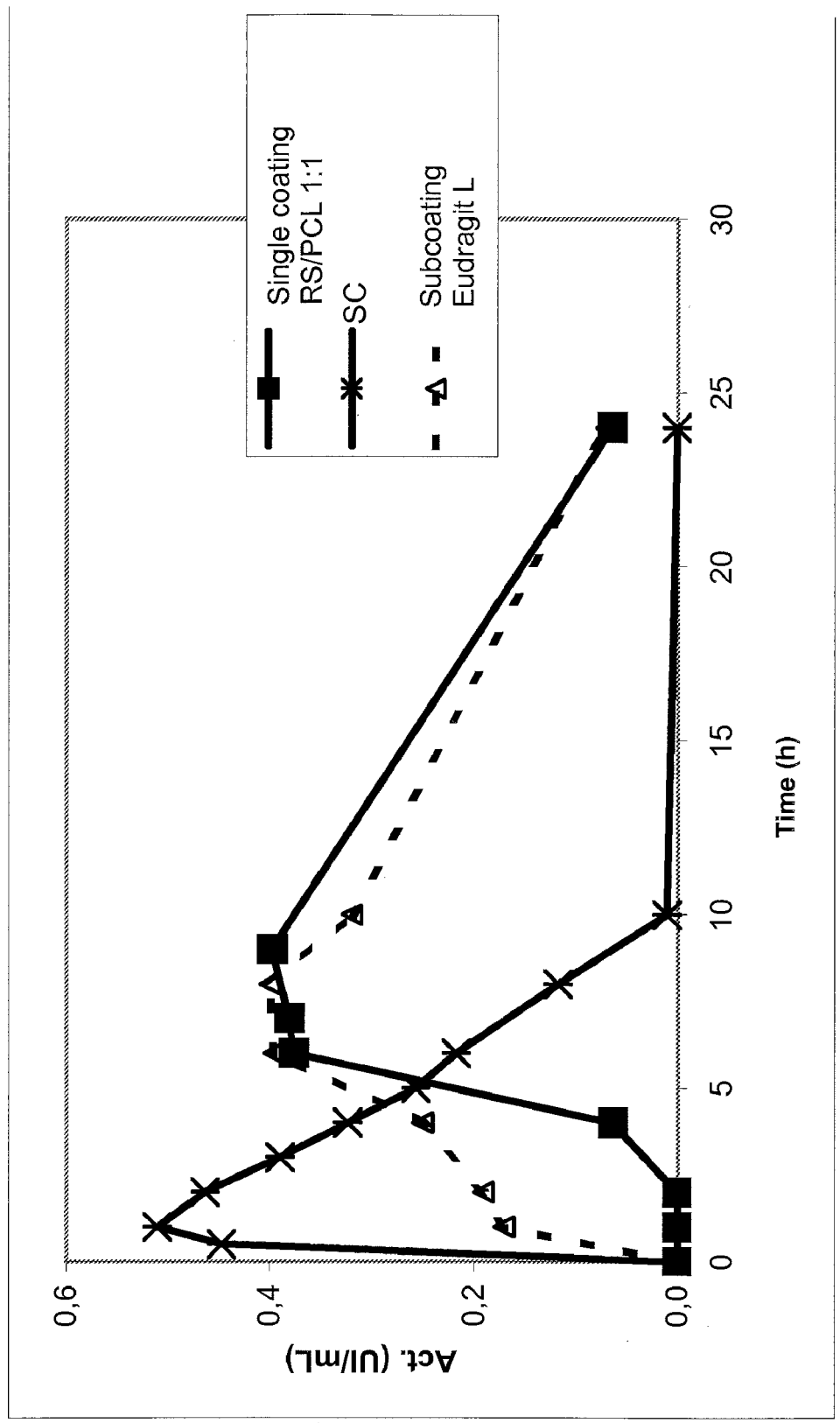
FIG. 22: depicts a plot of the time-dependent Anti-Xa activity per ml in plasma of New Zealand White rabbits after the oral administration of 600 IU anti-Xa/kg of bemiparin granules in gelatine capsules. The groups correspond to granules with or without subcoating with Eudragit® L and coated by a mixture of Eudragit® RS and PCL in 1:1 proportion (n=3). SC corresponds to the administration of 150 IU/kg of Bemiparin dissolved in 1 ml of distilled water by subcutaneous route (n=3).

In Vivo Studies of Coated Granules Containing Bemiparin and Having an Intermediate Coating Layer Measurement of the Anti-Xa Activity FIG. 22 compares the plasma anti-Xa activities after the oral administration to rabbits of non-enteric hard gelatine capsules containing Bemiparin granules produced according to example 16 and their comparison with bemiparin granules only containing the outer coating of Eudragit® RS and PCL in a proportion of 1:1 according to example 12 (600 IU/kg). As is evident in the figure, the application of a subcoat in the granule structure maintains the Bemiparin absorption levels obtained without a subcoat. In this case it is evident that the presence of active compound on the surface is not structurally necessary for the vehicle to achieve the absorption of the active compound, as there is a physical separation between the active compound and the polymeric mixture on the surface. Once the formulation is administered, the granule is hydrated and the Bemiparin starts to diffuse outwards, and it is the suitable ratio between the interaction of the polymeric coating with the digestive tract wall and the release of the active compound which achieves that Bemiparin is absorbed in sufficiently high quantities. Likewise, it is evident that the absorption of Bemiparin achieved in the granule using the same compositions on the surface is equivalent and independent of the internal structure of the particulate vehicle provided that the active compound is quickly released Values of Cmax and the relative bioavailabilities obtained for each one of these formulations are reflected in the following table:

| % coating | Cmax | F (%) relative to 150 IU/kg sc |
|---|---|---|
| 4 (only outer) | 0.3978 | 39.59 |
| 4 (subcoat) + 4 (outer) | 0.400 | 45.63 |

Despite the fact that the subcoat has been prepared by spraying a polymer solution in acetone, it can be easily deduced by any person skilled in the art that similar results can be obtained using any other polymer solvent or by spraying an aqueous suspension thereof that the company (Degussa, Germany) markets under the name Eudragit® L 30D For the purposes of clarifying the results obtained and demonstrating the activity achieved with the suitable polymeric mixture, the incorporation of excipients commonly used in granulation procedures has been avoided intentionally (both for the core and for the coating) but it is also obvious for a person skilled in the art that this preparation procedure can also be performed using any of the excipients that may be required to optimize the granulation process.

EXAMPLE 18

Formation of Coated Granules Containing Bemiparin

The manufacturing of the granules is carried out in two stages. The first stage, called core preparation, consists of preparing primary bemiparin granules with microcrystalline cellulose (MCC). A high-speed Zanchetta Rotolab® granulator/mixer has been used to prepare the granules.

Composition:

| Avicel pH 101 | 90 g | 85.71% |
|---|---|---|
| Bemiparin | 15 g | 14.29% |
| Water milli-Q | q.s. | |

Preparation Procedure:
1. Dissolve the Bemiparin in 50 mL of milli-Q water and place it in the dropping funnel.
2. Weigh the exact quantity of avicel and place it in the granulator container.
3. Add the Bemiparin solution to the avicel in movement due to the drive blade
4. Check the degree of wetting of the avicel and the formation of the granulate.
5. Add the necessary quantity of milli-Q water until the granulatee is formed.
6. Remove the granulate from the equipment and sieve them through a sieve with a mesh opening of 1 mm.
7. Dry in oven at 37° C. for 2 hours and then at ambient temperature.

Equipment Conditions:

| Speed of the impeller (drive blade) | 250-300 rpm |
|---|---|
| Chopper | Off |
| Heating jacket | Off |

The second stage, of coating, consists of adding a polymer mixture to the primary granules, either dissolved or in suspension, by spraying of the primary cores in fluidized bed (Mini Glatt® with microkit accessory). The primary granulates are then coated directly with different proportions of each of the polymers.

Composition:

| Coating solution: | Eudragit ® RS PO | 2.5 g |
|---|---|---|
| | Pluronic F68 | 2.5 g |
| | Acetone | 100 mL |

To perform the coating of the previously produced primary granules, we introduce 30 grams thereof in the granulator to coat them in the aforementioned coating solution wherein both polymers are in a 1:1 ratio. Granules have been prepared with a coating percentage of 5% w/w in relation to the initial mass of primary granules introduced.

Preparation Procedure:
1. Place the inner core (30 g) in the product filling tubulator of the fluidized bed
2. Fill the hose with the coating solution up to the spray nozzle.
3. Switch on the equipment and adjust the process parameters
4. Perform the coating and remove the end product from the tubulator.

Process Parameters:

| Temperature (° C.) | Pump index | Air pressure of the process (bars) | Spray air pressure (bars) | Air temperature of the process (° C.) |
|---|---|---|---|---|
| Ambient | 1.0 | 0.08-0.15 | 0.50 | 25 |

Once the spraying of the polymeric solution has concluded, the process air is maintained during 20 seconds for the coating to dry.

Characterization of the Granules Produced:

Morphology and Size

Figure 23:
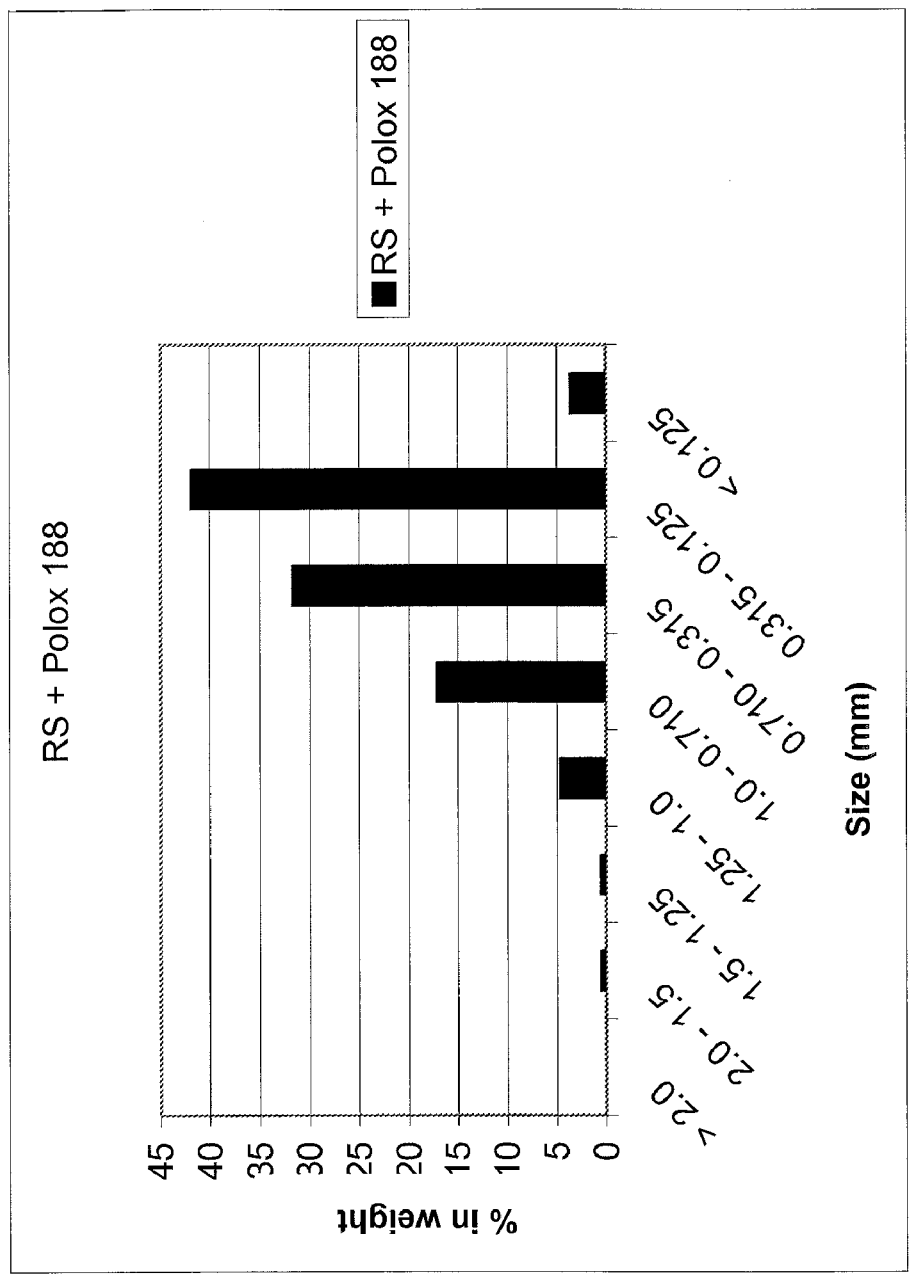
FIG. 23: depicts a plot of the particle size distribution of granules produced according to the invention. The bars represent the percentage (%) by mass of the different fractions obtained after the sieving process.

The granules coated with the Eudragit® RS and Pluronic F68 matrix (in 1:1 ratio), the coating representing a gain of 4% over the weight of the primary MCC and Bemiparin granule, have been observed under the optical microscope in these conditions and after having been dispersed in a 4% PVA solution. The size has been determined by separation by sieving, using sieves with mesh openings of 2, 1.5, 1.25, 1, 0.71, 0.315 and 0.125 mm. The result is expressed in percentage of the total mass measured which the different fractions obtained represent. The distribution of sizes obtained can be observed in FIG. 23.

As can be observed in the figure, 96.44% of the total mass of the granulate have a particle size over 0.125 mm.

In Vitro Release Kinetics

The release assays have been performed in sink conditions in a 6-vessel dissolution apparatus with water bath thermostatted at 37° C. 166 mg of granules produced (with 4% coating) have been introduced in a hard number 1 gelatin capsule and the capsules have been introduced in spinner baskets which are immersed in the dissolution medium (400 ml of pH 6.8 phosphate buffer). The spinner basket rotation rate has been maintained at 100 rpm.

1.5 mL samples have been taken with the automatic pipette after 30 minutes, and after 1, 1.5, 2, 4, 6 and 24 hours. The volumes collected are substituted by 1.5 mL of fresh buffer in order to maintain a constant volume within the vessels. These aliquots are then filtered with a MILLIPORE filter of 0.22 µm porosity.

The quantities of bemiparin released are evaluated by nephelometry, and then the curves which represent the release kinetics of bemiparin as a function of time are established. The release kinetics have been performed in duplicate for each one of the samples (n=2).

Figure 24:
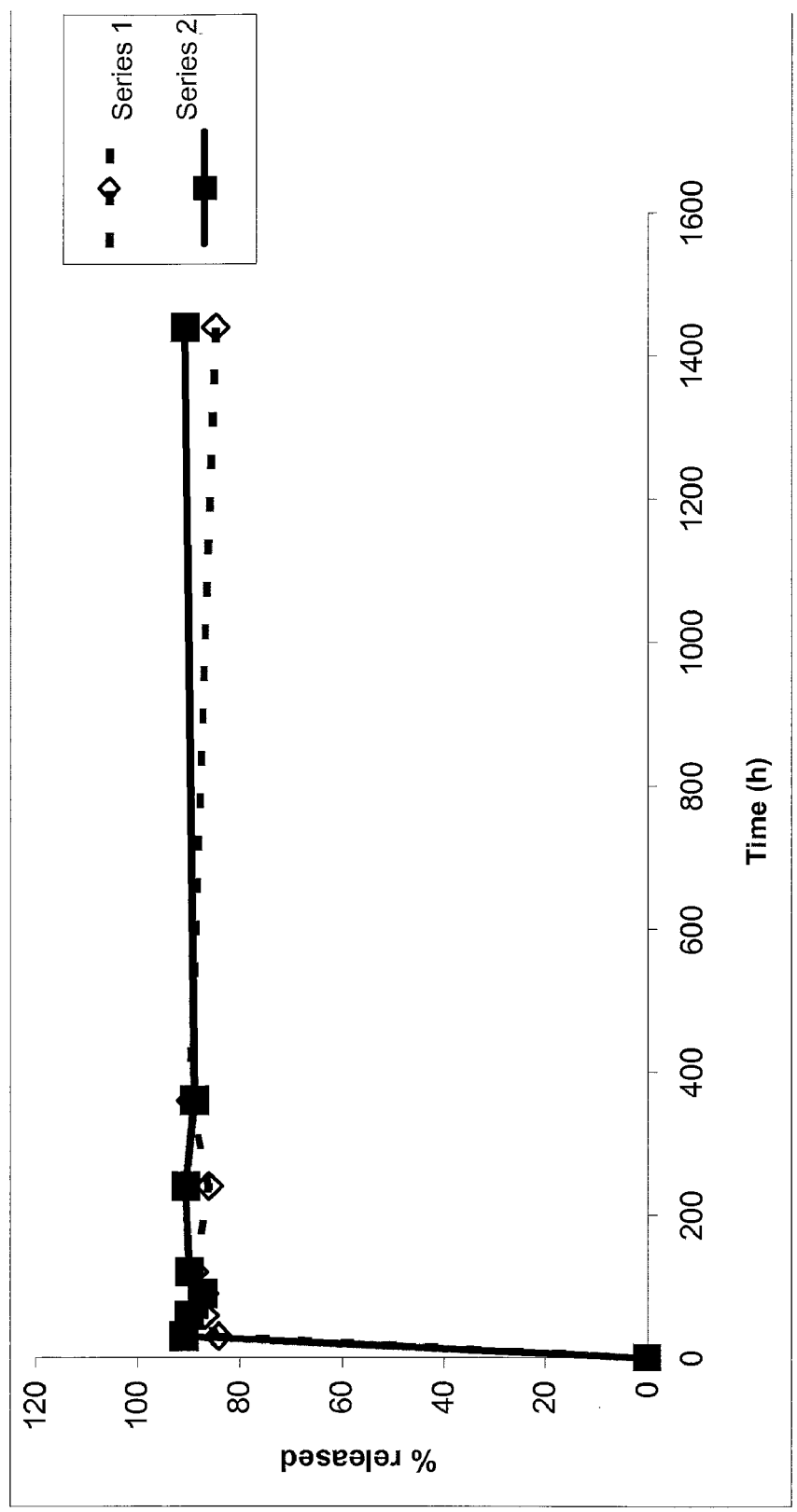
FIG. 24: depicts a release profile for release of Bemiparin from the granules of the invention. The figure represents percentage (%) of Bemiparin released over the total as a function of time. The dissolution medium is phosphate buffer pH 6.8 (n=2; series 1 and 2).

FIG. 24 shows that the release profile of these formulations is two-phase. In this case, the initial release represents more than 80% in all the measurements made. It can be clearly observed that Poloxamer 188, which is a polymer which shows avidity for water, facilitates the hydration of the granule and the release of the bemiparin contained therein.

EXAMPLE 19

In Vivo Studies of Granules with Bemiparin of Example 18

Measurement of the Anti-Xa Activity

Figure 25:
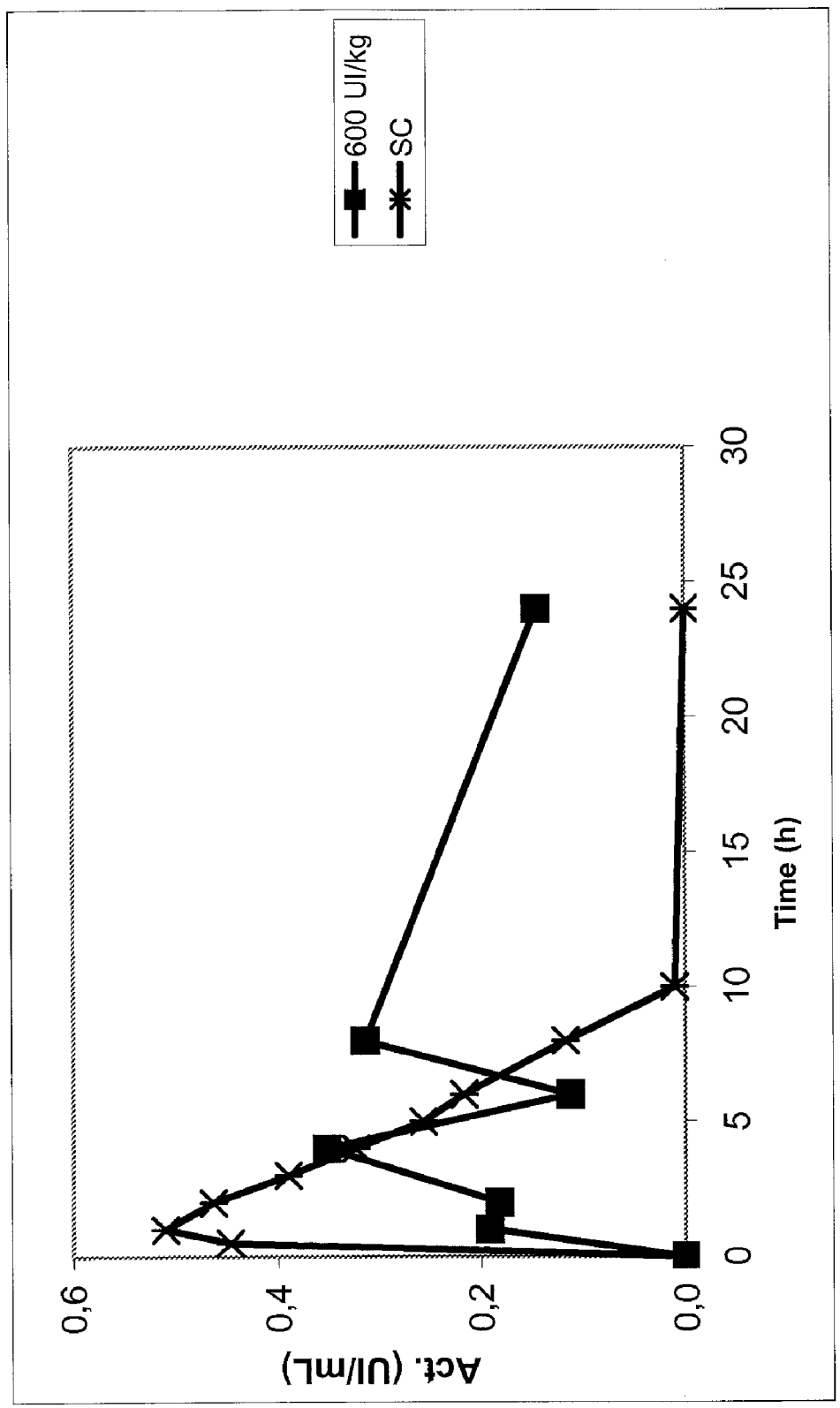
FIG. 25: depicts a plot of the time-dependent Anti-Xa activity per ml in plasma of New Zealand White rabbits after the oral administration of 600 IU anti-Xa/kg of bemiparin granules in gelatine capsules. The granules have on the surface a Eudragit® RS and Pluronic F68 matrix in 1:1 proportion (n=3). SC corresponds to the administration of 150 IU/kg of Bemiparin dissolved in 1 ml of distilled water by subcutaneous route (n=3).

FIG. 25 compares the plasma anti-Xa activities after the oral administration to rabbits of hard gelatine capsules (with enteric coating of Eudragit® L) containing Bemiparin granules produced according to example 18 (600 IU/kg). As can be observed in the figure, the administration of bemiparin granules which present in the coating a polymeric matrix constituted by Eudragit® RS and Pluronic F68 in 1:1 proportion gives rise to significantly high levels of plasma activity. Values of Cmax and the relative bioavailabilities obtained are reflected in the following table:

| % coating | Cmax | F (%) relative to 150 IU/kg sc |
|---|---|---|
| 5 | 0.352 | 41.20 |

By way of conclusion, it can be highlighted that the appropriate use of polymers in the preparation of formulations permits achieving the absorption of poorly permeable active compounds in significant quantities after their administration by oral route. The combined effect of a sufficient adhesion to the mucosal wall and an efficient release of the active compound provided by Eudragit® RS and the polymers that combine with it in suitable proportions is sufficiently important to permit active compounds, poorly permeable to the absorption barrier to pass through it, despite the large size of the formulations presented by way of example which may exceed one millimetre in diameter. This observation is surprising in light of the information that may be found today in the state of the art, which continually stresses the need to reduce the formulation size to produce more efficient dispersions with a greater contact time with the absorption mucosa. It is also obvious for a person skilled in the art that the formulations included in the examples herein have further undeniable advantages over the production of microparticles and nanoparticles, since they are produced by processes commonly used in the pharmaceutical industry, they have less variability in the interbatch production and are easily scalable to industrial batches, unlike what happens with the other formulations.

EXAMPLE 20

Bemiparin Suspension in a Dissolution of Eudragit® RS PO and Polycaprolactone

The suspension was obtained in three steps. In a first step, 9.25 mg of Eudragit® RS PO and 9.25 mg of PCL were dissolved in 1.85 mL of acetone. Subsequently, a dissolution of Bemiparin in water (18.5 mg of Bemiparin in 200 µL of water) was prepared. Finally, the aqueous dissolution was added to the dissolution of Eudragit® RS PO and PCL in acetone, and the whole mass was subjected to magnetic stifling for 5 minutes.

The suspension of Bemiparin in acetone (without polymers) was performed as follows: a dissolution of 18.5 mg of Bemiparin in 200 µL of water was added to 1.85 mL of acetone. The whole mass was subjected to magnetic stifling for 5 minutes.

EXAMPLE 21

In Vivo Studies of the Bemiparin Suspension of Example 20

Measurement of the Anti-Xa Activity

Figure 26:
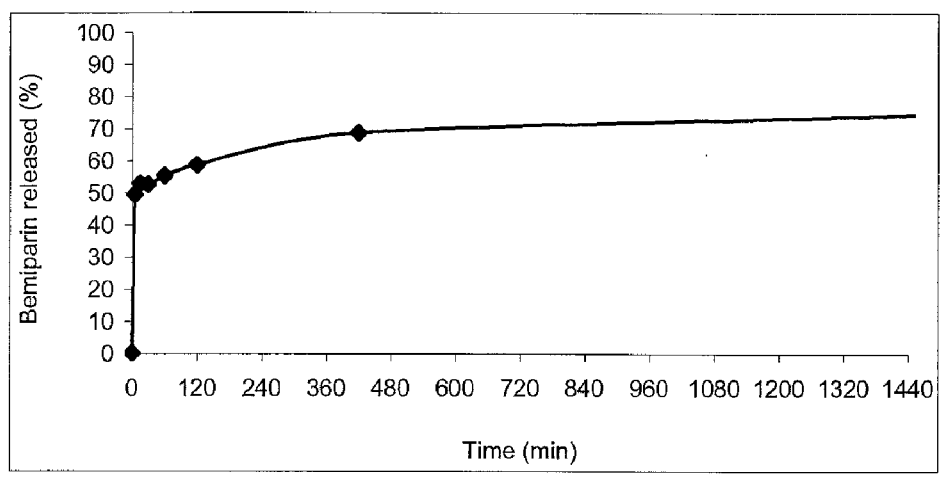
FIG. 26: depicts a plot of the time-dependent anti Xa activity per ml in plasma of New Zealand White rabbits after the oral administration of 600 IU anti-Xa/kg of bemiparin suspension in an Eudragit® RS/PCL polymer solution (black boxes), and bemiparin suspension in acetone (black circkes). (n=3). White triangles corresponds to the administration of 150 IU/kg of Bemiparin dissolved in 1 ml of distilled water by subcutaneous route (n=3).

FIG. 26 shows the plasma anti-Xa activities after the oral adminsitration to rabbits of suspensions obtained according to example 20 (600 IU/kg). As it can be observed in the figure, the administration of Bemiparin suspension in a dissolution of Eudragit® RS PO and PCL in acetone (in a ratio of polymers of 1:1) gives rise to significantly high levels of plasma anti-Xa activity. Values of Cmax and the relative bioavailability obtained are reflected in the following table:

| Cmax | F (%) relative to 150 UI/kg sc |
|---|---|
| 0.218 | 25.00 |

Likewise, it can be observed that the administration of the Bemiparin suspension in acetone without either Eudragit® RS PO or PCL does not give rise to the apparition of levels of plasma anti-Xa activity in rabbits. This shows that the acetone by itself, does not excert any effect on the absorption of Bemiparin upon its oral administration.

The diffusion of acetone toward the gastrointestinal fluids produces the precipitation of Eudragit® RS PO and PCL, conforming a solid matrix which encompasses Bemiparin. The active principle diffuses from the matrix and upon its absorption, it passes into systemic circulation.

EXAMPLE 22

(Comparative): Preparation of Eudragit® RS and PLGA Microparticles Containing Bemiparin Microparticles containing Bemiparin were prepared by a W/O/W emulsification/solvent extraction method. Briefly, 4 ml of an aqueous solution having 5% (w/v) Bemiparin were emulsified into 20 ml of an Eudragit® RS and PLGA solution in ethyl acetate (each polymer at 2,5% w/v) by sonication during 30 s at 11 W. Then this emulsion was poured into 80 ml of a 0.1% (w/v) PVA solution in water under magnetic stirring. Magnetic stirring was maintained during 1 min and then the whole content was poured into 1600 ml 0.1% (w/v) PVA solution in water and the whole mass was kept under mechanical agitation during 1 h. Then microparticles were separated by filtration, washed with water and dried in a vacuum oven at 37° C. during 2 days.

Relative proportions of each of the two polymers are shown in the following table:

| % PLGA | % Eudragit ® RS |
|---|---|
| 50 | 50 |

Microparticle Characterization:
Particle Size

Particle size was determined by laser diffraction techniques by using a Malvern Mastersizer apparatus. Microparticles were first resuspended in phosphate buffer at pH 7.4. During the measurement, the suspension was maintained by mechanical agitation of the measurement cell.

Mean average size of the obtained microparticles was 71.4 µm.

In Vitro Release Profile

The objective in this trial is to determine the amount of bemiparin released from microparticles along the time. This measurement must be done under "sink" conditions, i.e., the release medium must have a volume in which the maximum drug concentration is less than 30% of the saturation concentration of this drug, in order to avoid limiting effects of drug concentration gradients from microparticles surface.

Release studies have been done by resuspending (magnetic stifling at 300 rpm) 50 mg of each batch of microparticles in 20 ml phosphate buffer (PBS, 0.011 M and NaCl 0.15 M) at pH 7.4 having 0.1% (w/v) Tween 80 at 37° C.

Figure 27:
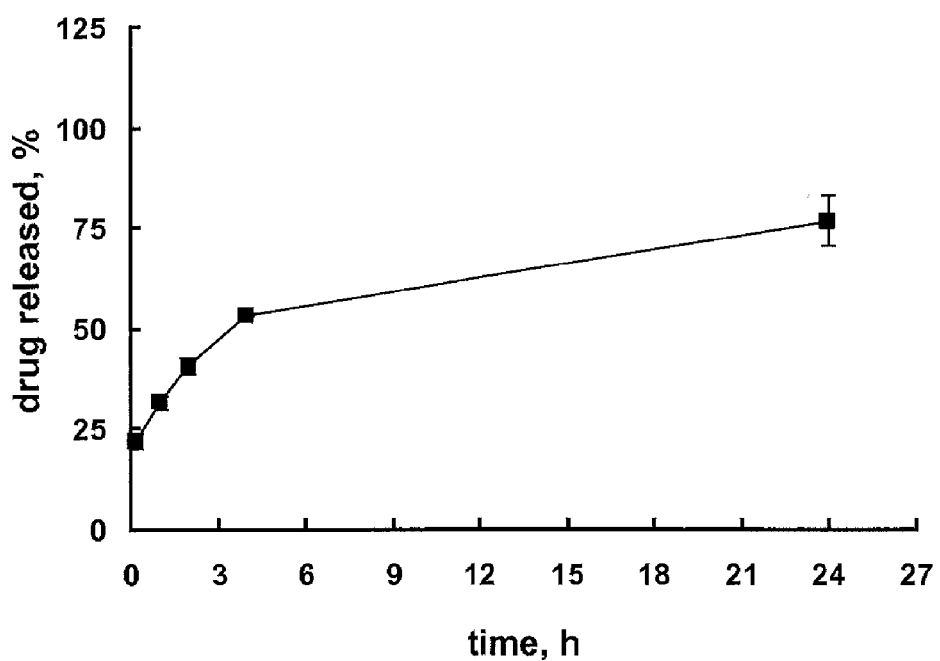
FIG. 27: depicts a release profile for in vitro release of Bemiparin from microparticles containing Eudragit® RS and PLGA, as prepared by a W/O/W emulsification/solvent extract method (n=3), the particles having an average diameter of 71.4 µm.

1 mL samples were collected at 5, 15 and 30 minutes and then at 1, 2, 7 and 24 hours. Collected volumes were substituted in the medium by 1 mL of fresh buffer in order to keep volume constant. Samples were then filtrated (0.22 µm pore size, Millipore). Bemiparin amount in samples is determined by nephelometry. Determined release profiles (n=3) are shown in FIG. 27.

Bemiparin microparticles provided a two phase release profile, with an initial fast release followed by a second slow-release phase. As can be seen in the figure, more than 50% of encapsulated bemiparin is being released from microparticles during the first 60 minutes. This should allow the drug to be released in significantly high amounts once the microparticles are being placed in the gastrointestinal tract.

In Vivo Studies with Bemiparin Microparticles
Study in New Zealand White Rabbits Bemiparin microparticles were orally administered to New Zealand White rabbits weighing an average of 3 kg. The dose of Bemiparin was 600 IU anti Xa per Kg and the required amount of microparticles was orally given to rabbits into hard gelatin capsules. 2 groups of three rabbits were used, and each group received hard gelatin capsules containing PLGA/Eudragit® RS microparticles loaded with Bemiparin with the following variables:

Group 1: Bemiparin microparticles into not gastrorresistant hard gelatin capsules Group 2: Bemiparin microparticles into gastrorresistant hard gelatin capsules Blood samples were collected after oral administration at times 1, 2, 4, 6, 8, 10 and 24 hours. Bemiparin presence in plasma of rabbits was determined by measuring plasma anti Xa factor levels.

Oral administration of Eudragit® RS and PLGA microparticles having bemiparin did not provide detectable levels of anti Xa activity in plasma of rabbits in none of the animals studied.

Study in Cynomolgus Monkeys

Bemiparin containing microparticles were orally administered to Cynomolgus monkeys having an average weight of 3 Kg. Bemiparin dose was 10,000 IU anti Xa per animal.

Blood samples were collected at 8 and 24 hours after oral administration of microparticles and presence of Bemiparin in plasma of monkeys was determined by measuring anti Xa factor activity in plasma.

Oral administration of Eudragit® RS and PLGA microparticles containing bemiparin did not provide detectable plasma levels of anti Xa activity in none of the animals studied.

EXAMPLE 23

(Comparative): Preparation of Eudragit® RS and Polycaprolactone Microparticles Containing Bemiparin Microparticles containing Bemiparin were prepared by a W/O/W emulsification/solvent extraction method. Briefly, 4 ml of an aqueous solution having 5% (w/v) Bemiparin were emulsified into 20 ml of an Eudragit® RS and PLGA solution in ethyl acetate (each polymer at 2,5% w/v) by sonication during 30 s at 11 W. Then this emulsion was poured into 80 ml of a 0.1% (w/v) PVA solution in water under magnetic stirring. Magnetic stirring was maintained during 1 min and then the whole content was poured into 1600 ml 0.1% (w/v) PVA solution in water and the whole mass was kept under mechanical agitation during 1 h. Then microparticles were separated by filtration, washed with water and dried in a vacuum oven at 37° C. during 2 days.

The relative proportion of each of the two polymers is shown in the

| % PLGA | % Eudragit ® RS |
|---|---|
| 50 | 50 |

Microparticle Characterization:
Particle Size

Particle size was determined by laser diffraction techniques by using a Malvern Mastersizer apparatus. Microparticles were first resuspended in phosphate buffer at pH 7.4. During the measurement, the suspension was maintained by mechanical agitation of the measurement cell.

Mean average size of the obtained microparticles was 76.5 μm.

In Vitro Release Profile

The objective in this trial is to determine the amount of bemiparin released from microparticles as a function of time. This measurement must be done under "sink" conditions, i.e., the release medium must have a volume in which the maximum drug concentration is less than 30% of the saturation concentration of this drug, in order to avoid limiting effects of drug concentration gradients from microparticles surface.

Release studies have been done by resuspending (magnetic stifling at 300 rpm) 50 mg of each batch of microparticles in 20 ml phosphate buffer (PBS, 0.011 M and NaCl 0.15 M) at pH 7.4 having 0.1% (w/v) Tween 80 at 37° C.

1 mL samples were collected at 5, 15 and 30 minutes and then at 1, 2, 4 and 24 hours. Collected volumes were substituted in the medium by 1 mL of fresh buffer in order to keep volume constant. Samples were then filtrated (0.22 μm pore size, Millipore). Bemiparin amount in samples is determined by nephelometry. Determined release profiles are depicted in FIG. 27 (n=3).

Figure 28:
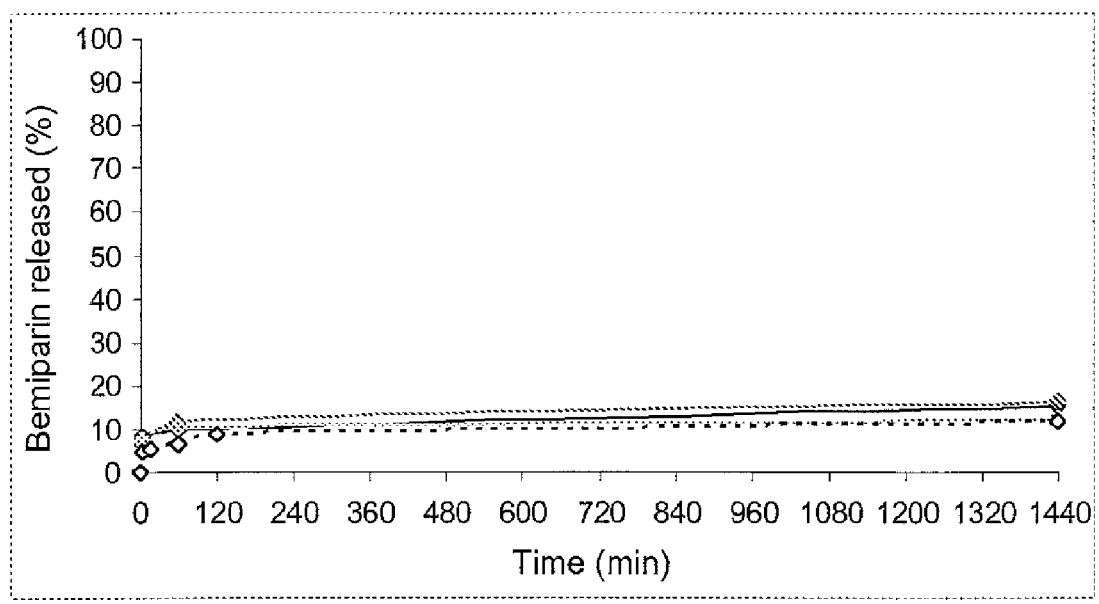
FIG. 28: depicts a release profile for in vitro release of Bemiparin from microparticles containing Eudragit® RS and PCL, as prepared by a W/O/W emulsification/solvent extract method (n=3), the particles having an average diameter of 76.5 µm.

The more hydrophobic nature of Polycaprolactone compared to PLGA delays microparticle hydration and, consequently, bemiparin is being released more slowly on the first hours (FIG. 28). This delay in the initial release should allow the release of clinically relevant amounts of bemiparin in the gastrointestinal tract once the microparticles have been released from the hard gelatin capsule.

In Vivo Studies with Bemiparin Microparticles
Study in New Zealand White Rabbits Bemiparin microparticles were orally administered to New Zealand White rabbits weighing an average of 3 kg. The dose of Bemiparin was 600 IU anti Xa per Kg and the required amount of microparticles was orally given to rabbits into hard gelatin capsules. 2 groups of three rabbits were used, and each group received hard gelatin capsules containing PCL/Eudragit® RS microparticles loaded with Bemiparin with the following variables:

Group 1: Bemiparin microparticles into not gastrorresistant hard gelatin capsules
Group 2: Bemiparin microparticles into gastrorresistant hard gelatin capsules Blood samples were collected after oral administration at 1, 2, 4, 6, 8, 10 and 24 hours. Bemiparin presence in the plasma of rabbits was determined by measuring plasma anti Xa factor levels.

Oral administration of Eudragit® RS and PCL microparticles having bemiparin did not provide detectable levels of anti Xa activity in plasma of rabbits in none of the animals studied.

Study in Cynomolgus Monkeys

Bemiparin containing microparticles were orally administered to Cynomolgus monkeys having an average weight of 3 Kg. Bemiparin dose was 10,000 IU anti Xa per animal.

Blood samples were collected at 8 and 24 hours after oral administration of microparticles and presence of Bemiparin in plasma of monkeys was determined by measuring anti Xa factor activity in plasma.

Oral administration of Eudragit® RS and PCL microparticles containing bemiparin did not provide detectable plasma levels of anti Xa activity in none of the animals studied.

EXAMPLE 24

(Comparative): Preparation of Eudragit® RS and PLGA Microparticles Containing Bemiparin In order to reduce particle size of microparticles fabricated according to example 22, microparticles containing Bemiparin were prepared by a small change in W/O/W emulsification/solvent extraction method described in example 22. Briefly, 4 ml of an aqueous solution having 5% (w/v) Bemiparin were emulsified into 20 ml of an Eudragit® RS and PLGA solution in ethyl acetate (each polymer at 2,5% w/v) by sonication during 30 s at 11 W. Then this emulsion was poured into 50 ml of a 8% (w/v) PVA solution in water under magnetic stifling. Magnetic stifling was maintained during 1 min and then the whole content was poured into 100 ml 2% (w/v) Isopropanol solution in water and the whole mass was kept under mechanical agitation during 1 h. Then microparticles were separated by filtration, washed with water and dried in a vacuum oven at 37° C. during 2 days.

The relative proportion of each of the two polymers is shown in the following table:

| % PLGA | % Eudragit ® RS |
|---|---|
| 50 | 50 |

Microparticle Characterization:
Particle Size

Particle size was determined by laser diffraction techniques by using a Malvern Mastersizer apparatus. Microparticles were first resuspended in phosphate buffer at pH 7.4. During the measurement, the suspension was maintained by mechanical agitation of the measurement cell.

Mean average size of the obtained microparticles was 2.2 μm.

In Vitro Release Profile

The objective in this trial is to determine the amount of bemiparin released from microparticles along the time. This measurement must be done under "sink" conditions, i.e., the release medium must have a volume in which the maximum drug concentration is less than 30% of the saturation concentration of this drug, in order to avoid limiting effects of drug concentration gradients from microparticles surface.

Release studies have been done by resuspending (magnetic stifling at 300 rpm) 50 mg of each batch of microparticles in 20 ml phosphate buffer (PBS, 0.011 M and NaCl 0.15 M) at pH 7.4 having 0.1% (w/v) Tween 80 at 37° C.

1 mL samples were collected at 5, 15 and 30 minutes and then at 1, 2 and 24 hours. Collected volumes were substituted in the medium by 1 mL of fresh buffer in order to keep volume constant. Samples were then filtrated (0.22 μm pore size, Millipore). Bemiparin amount in samples is determined by nephelometry. Determined release profiles are depicted in FIG. 28 (n=4).

Figure 29:
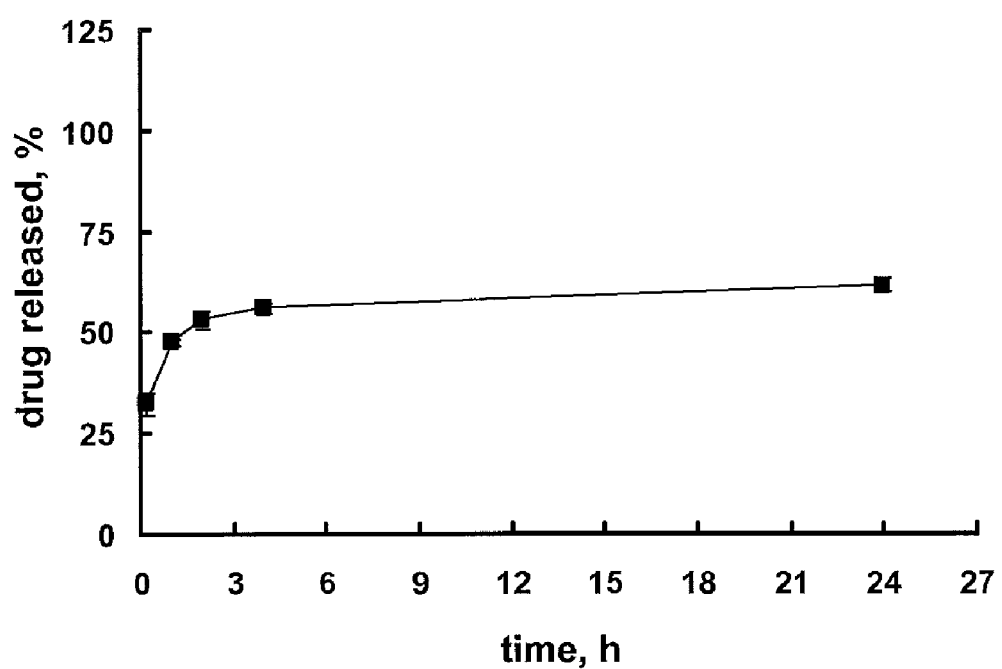
FIG. 29: depicts a release profile for in vitro release of Bemiparin from microparticles containing Eudragit® RS and PLGA, as prepared by a W/O/W emulsification/solvent extract method (n=3), the particles having an average diameter of 2.2 µm. The results are presented as individual release profiles for each of the four measurements taken.

The figure shows how microparticles fabricated according to the new procedure provide a slower initial release of Bemiparin (FIG. 29). A slower matrix forming polymer precipitation rate could lead to the formation of less porous matrixes.

In Vivo Study in New Zealand White Rabbits

Bemiparin microparticles were orally administered to New Zealand White rabbits weighing an average of 3 kg. The dose of Bemiparin was 600 IU anti Xa per Kg and the required amount of microparticles was orally given to rabbits into hard gelatin capsules.

Blood samples were collected after oral administration at times 1, 2, 4, 6, 8, 10 and 24 hours. Bemiparin presence in plasma of rabbits was determined by measuring plasma anti Xa factor levels.

Oral administration of Eudragit® RS and PLGA microparticles having bemiparin did not provide detectable levels of anti Xa activity in plasma of rabbits in none of the animals studied.

EXAMPLE 25

(Comparative): Preparation of Eudragit® RS and PLGA Microparticles Containing Bemiparin In order to increase particle size of microparticles fabricated according to example 22, microparticles containing Bemiparin were prepared by a small change in W/O/W emulsification/solvent extraction method described in example 22. Briefly, 4 ml of an aqueous solution having 5% (w/v) Bemiparin and 20% PEG1500 were emulsified into 20 ml of an Eudragit® RS and PLGA solution in ethyl acetate (each polymer at 2,5% w/v) by mechanical agitation (Ultraturrax T25 at 9500 rpm). Then this emulsion was poured into 80 ml of a 0.1% (w/v) PVA solution in water under magnetic stifling. Magnetic stifling was maintained during 1 min and then the whole content was poured into 1400 ml 0.1% (w/v) PVA solution in water and the whole mass was kept under mechanical agitation during 1 h. Then microparticles were separated by filtration, washed with water and dried in a vacuum oven at 37° C. during 2 days.

Microparticle Characterization:

Particle Size

Particle size was determined by laser diffraction techniques by using a Malvern Mastersizer apparatus. Microparticles were first resuspended in phosphate buffer at pH 7.4. During the measurement, the suspension was maintained by mechanical agitation of the measurement cell.

Mean average size of the obtained microparticles was 168.4 µm.

In Vitro Release Profile

The objective in this trial is to determine the amount of bemiparin released from microparticles along the time. This measurement must be done under "sink" conditions, i.e., the release medium must have a volume in which the maximum drug concentration is less than 30% of the saturation concentration of this drug, in order to avoid limiting effects of drug concentration gradients from microparticles surface.

Release studies have been done by resuspending (magnetic stifling at 300 rpm) 50 mg of each batch of microparticles in 20 ml phosphate buffer (PBS, 0.011 M and NaCl 0.15 M) at pH 7.4 having 0.1% (w/v) Tween 80 at 37° C.

1 mL samples were collected at 5, 15 and 30 minutes and then at 1, 2 and 24 hours. Collected volumes were substituted in the medium by 1 mL of fresh buffer in order to keep volume constant. Samples were then filtrated (0.22 µm pore size, Millipore). Bemiparin amount in samples is determined by nephelometry. Determined release profiles are depicted in FIG. 29 (n=4).

Figure 30:
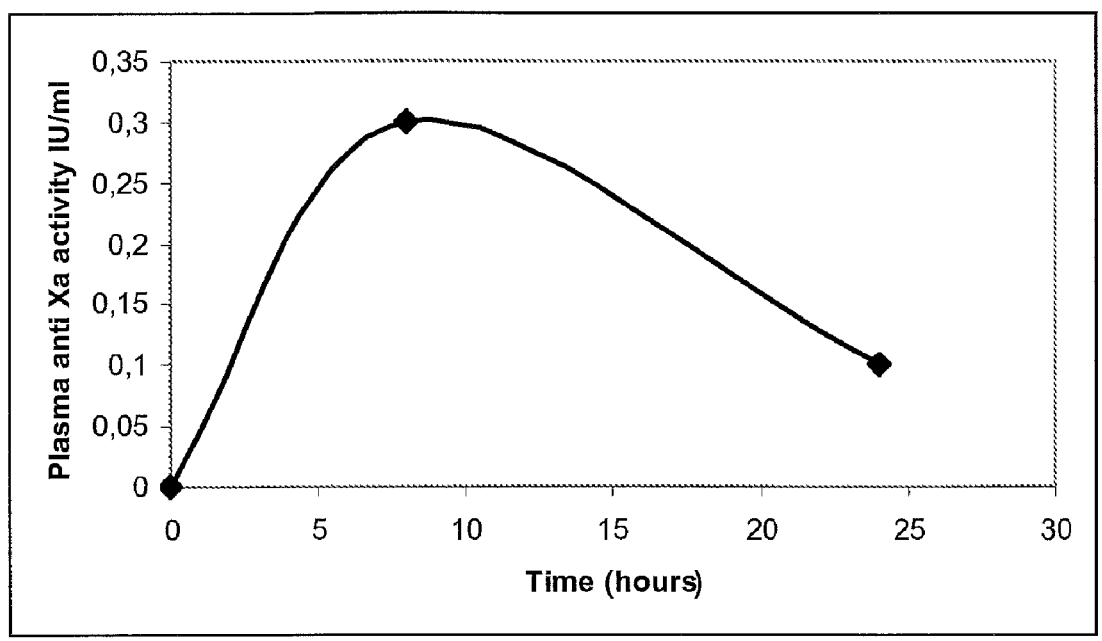
FIG. 30: depicts a release profile for in vitro release of Bemiparin from microparticles containing Eudragit® RS and PLGA, as prepared by a W/O/W emulsification/solvent extract method (n=3), the particles having an average diameter of 168.4 µm.

Even though these particles have a bigger particle size, the release profile of bemiparin is very similar to that obtained with microparticles having an average size of 71.4µ. As can be seen in the figure, more than 50% of encapsulated bemiparin is released during the first hour (FIG. 30), which should allow for significant amounts of bemiparin released once microparticles are released into the gastrointestinal tract.

In Vivo Study in New Zealand White Rabbits

Bemiparin microparticles were orally administered to New Zealand White rabbits weighing an average of 3 kg. The dose of Bemiparin was 600 IU anti Xa per Kg and the required amount of microparticles was orally given to rabbits into hard gelatin capsules.

Blood samples were collected after oral administration at times 1, 2, 4, 6, 8, 10 and 24 hours. Bemiparin presence in plasma of rabbits was determined by measuring plasma anti Xa factor levels.

Oral administration of Eudragit® RS and PLGA microparticles having bemiparin did not provide detectable levels of anti Xa activity in plasma of rabbits in none of the animals studied.

EXAMPLE 26

In Vivo Oral Administration to Cynomolgus Monkeys of Granules Described in Example 12

Bemiparin containing granules having an external coating of a PCL and Eudragit® RS polymer matrix were orally administered to Cynomolgus monkeys having an average weight of 3 Kg. Bemiparin dose was 10,000 IU anti Xa per animal.

Blood samples were collected at 8 and 24 hours after oral administration of microparticles and presence of Bemiparin in plasma of monkeys was determined by measuring anti Xa factor activity in plasma.

Figure 31:
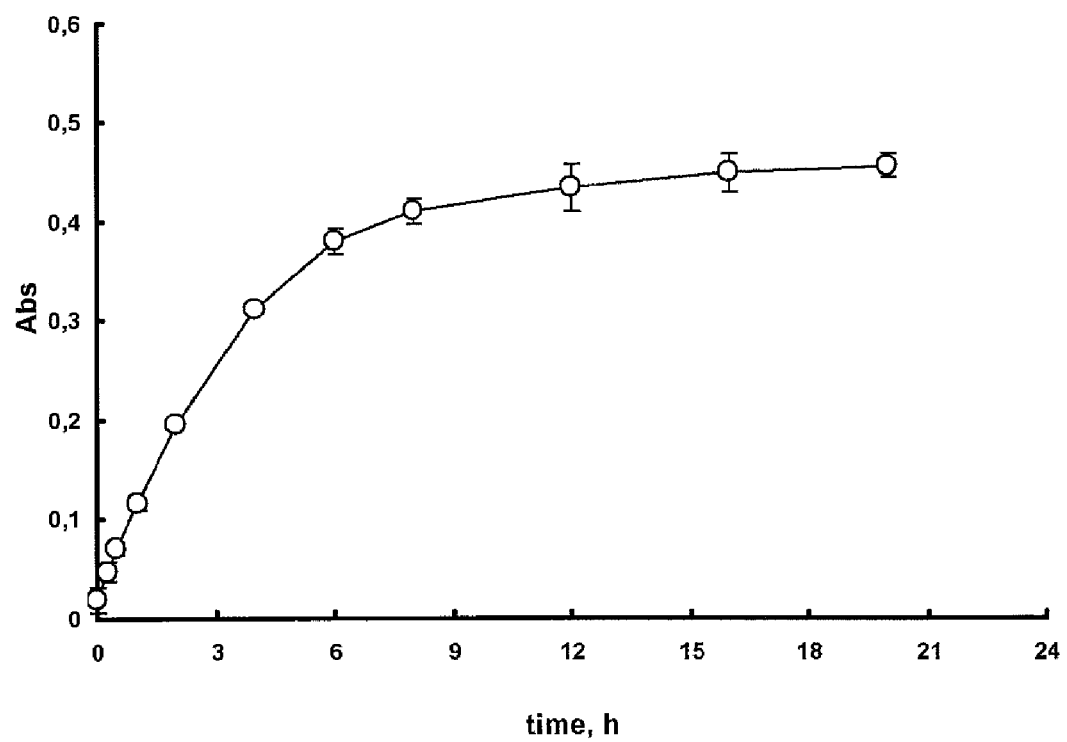
FIG. 31: depicts a plot of the time-dependent plasma anti-Xa activity in Cynomolgus monkeys following oral administration of 10,000IU anti-Xa bemiparin in granules prepared according to Example 12.

Oral administration of Eudragit® RS and PCL microparticles containing bemiparin provided clinically relevant plasma anti Xa values as depicted in FIG. 31.

The results clearly show how granules prepared according to example 12 provide in vivo plasma levels of anti Xa activity. However, all microparticles prepared by emulsification/solvent extraction procedures failed providing in vivo plasma levels after oral administration to rabbits and monkeys.

EXAMPLE 27

Preparation of Pellets Containing Bemiparin

Pellets containing Bemiparin were prepared according to the following procedure. In a first step Bemiparin was layered onto MCC cores with an aqueous solution having 20% (w/v) Bemiparin and 1% Kollidon K30 in a fluid bed apparatus (Glatt). The process parameters were:

| | |
|---|---|
| Inlet air temperature, ° C. | 68-70 |
| Product temperature, ° C. | 41-43 |
| Process air pressure, bar | 0.2 |
| Nozzle, mm | 0.5 |
| Spraying pressure, bar | 0.8 |
| Spray rate, g/min | 1.6 |
| Drying (38-40° C.), min | 5 |

Drug loading on the speres was 20% (w/w)

Drug layered pellets were then coated with a Eudragit® RS and PLGA mixture by spraying an organic solution having both polymers in a fluid bed apparatus. Process parameters were:

| | |
|---|---|
| Pre-warming (25-27° C.), min | 20 |
| Inlet air temperature, ° C. | 26-27 |
| Product temperature, ° C. | 22-25 |
| Process air pressure, bar | 0.2 |
| Nozzle, mm | 0.5 |
| Spraying pressure, bar | 0.6 |
| Spray rate, g/min | 2.4 |
| Drying (25° C.), min | 3 |

Polymer mixture loading in the final particles was 6%.

Pellets Characterization:

Particle size has been determined by separation by sieving, using sieves with mesh openings of 2, 1.5, 1.25, 1, 0.71, 0.315 and 0.125 mm. Main fraction collected presented a particle size between 1 and 0.71 mm.

The release assays have been performed in sink conditions in a 6-vessel dissolution apparatus with water bath at 37° C. 300 mg of pellets have been introduced in the dissolution medium (900 ml of pH 6.8 phosphate buffer). The paddles rotation rate has been maintained at 100 rpm.

1 mL samples have been taken with the automatic sampler after 15 and 30 minutes, and after 1, 2, 4, 6, 8, 12, 16 and 20 hours. The volumes collected are substituted by 1 mL of fresh buffer in order to maintain a constant volume within the vessels. These aliquots are then filtered with a MILLIPORE filter of 0.22 μm porosity.

The quantities of bemiparin released are evaluated by nephelometry, and then the curves which represent the release kinetics of bemiparin as a function of time are established. The release kinetics have been performed in duplicate for each one of the samples (n=2).

Figure 32:
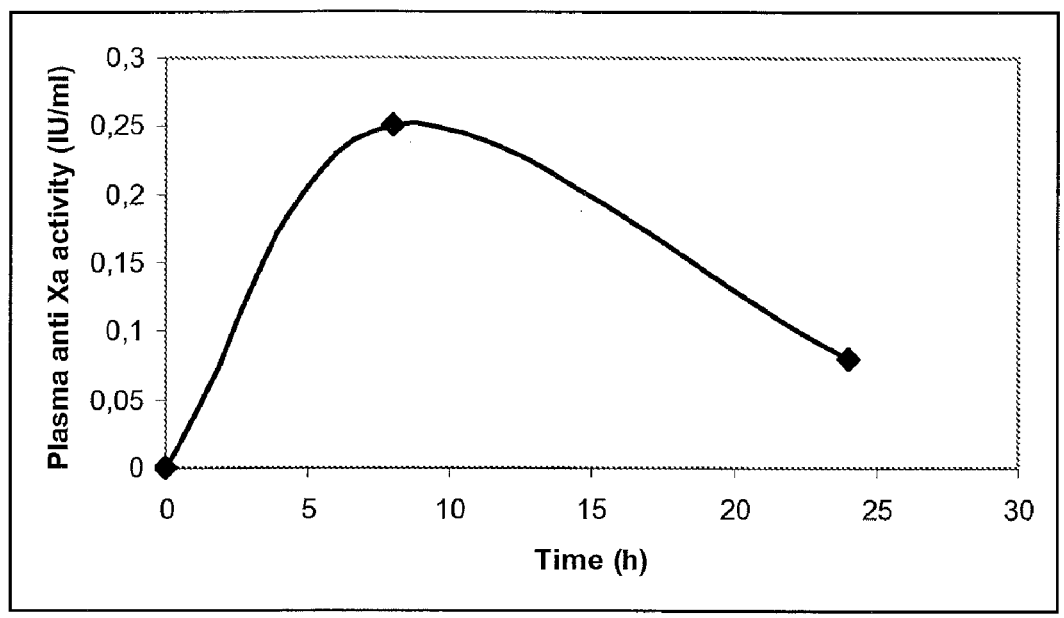
FIG. 32: depicts a release profile for in vitro release of Bemiparin from Eudragit® RS and PLGA pellets described in example 27.

FIG. 32 shows that the release profile of these formulations is two-phase. In this case, the initial release represents more than 80% in all the measurements made. The pellets allow release of Bemiparin in quantities enough as to make in vivo administrations.

EXAMPLE 28

In Vivo Oral Administration to Cynomolgus Monkeys of Pellets Described in Example 27

Bemiparin containing pellets having an external coating of a PLGA and Eudragit® RS polymer matrix were orally administered to Cynomolgus monkeys having an average weight of 3 Kg. Bemiparin dose was 10,000 IU anti Xa per animal.

Blood samples were collected at 8 and 24 hours after oral administration of microparticles and presence of Bemiparin in plasma of monkeys was determined by measuring anti Xa factor activity in plasma.

Figure 33:
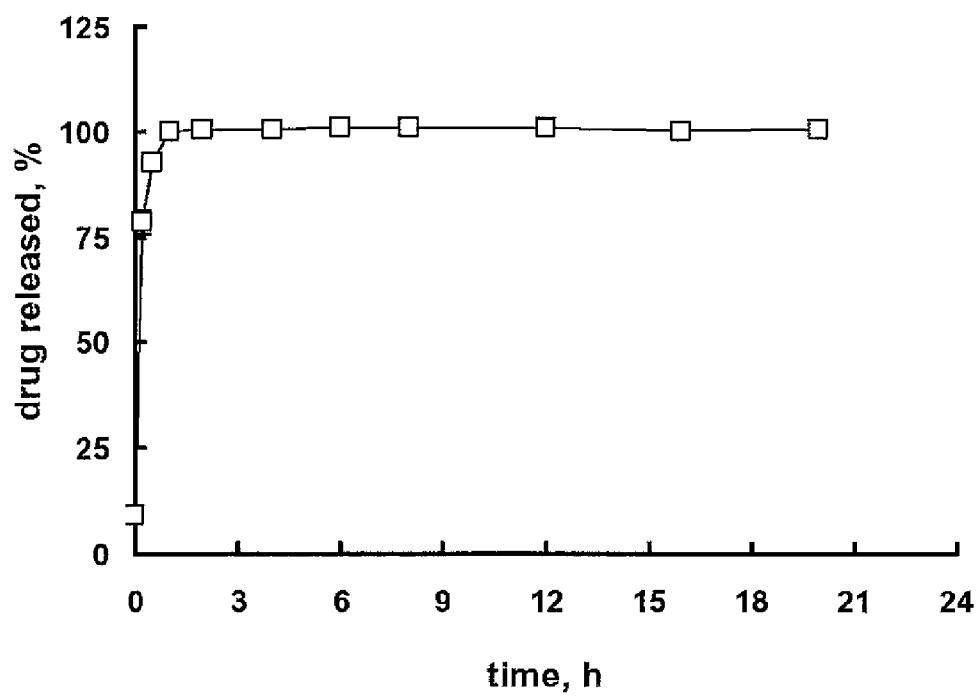
FIG. 33: depicts a plot of the time-dependent plasma anti-Xa activity in Cynomolgus monkeys following oral administration of 10,000IU anti-Xa bemiparin in pellets prepared according to Example 27.

Oral administration of Eudragit® RS and PLGA pellets containing bemiparin provided clinically relevant plasma anti Xa values as shown in FIG. 33.

The results clearly shows how pellets prepared according to example 27 provide in vivo plasma levels of anti Xa activity. Again, the results indicate superiority of these formulations compared with microparticles prepared by emulsification/solvent extraction procedures.

EXAMPLE 29

Preparation of Particulate Vectors Containing Heparin (Microparticles)

A solution of standard or low molecular weight heparin (1 ml, 5 000 IU) is emulsified with magnetic stirring for 3 minutes (500 rpm) in a solution of dichloromethane (10 ml) containing the polymer or the polymer mixture (250 mg). This first emulsion (water/oil) is then poured into a volume of water (1 500 ml) containing a surfactant, polyvinyl alcohol (0.1% degree of hydrolysis 88%), which gives, by mechanical stirring (2 000 rpm), a second water/oil/water emulsion. After stirring for 2 hours, precipitation of the dispersed droplets is obtained after evaporating off the solvent. The polymer microparticles thus obtained are then isolated by filtration. The particles have a mean size of 150 μm.

EXAMPLE 30

Preparation of Particulate Vectors Containing Heparin and Gelatin a (Microparticles)

The process is performed according to example 1, with addition of gelatin A (0.5%) to the heparin solution.

EXAMPLE 31

Preparation of Particulate Vectors Containing Heparin and Sodium Chloride (Microparticles)

The process is performed according to example 1, with addition of NaCl (0.2%) to the heparin solution.

As to used herein, the term "about" is taken to mean±10% or less, ±5% or less, ±2.5% or less, or ±1% or less of a specified value.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A method for the prevention or treatment of a disease or disorder that is therapeutically responsive to one or more active principles, the method comprising:

administering to a subject in need thereof a pharmaceutically effective amount of the one or more active principles, in a particulate vector, according to a predetermined dosing regimen, thereby providing a therapeutic response in the subject;

wherein the particulate vector comprises at least one active principle and a polymeric matrix comprising a mixture of at least one biodegradable polymer and at least one non-water soluble polycationic polymer:

the biodegradable polymer is selected from the group consisting of polyesters, lactic acid polymers, copolymers of lactic acid and of glycolic acid (PLGA), poly-ϵ-caprolactone (PCL), polyanhydrides, poly(amides), poly (urethanes), poly(carbonates), poly(acetals), poly (ortho-esters), polymers and copolymers derived from acrylic acid, polyethylene oxides, polypropylene oxides, polyethylene and polypropylene oxide copolymers, polycyanoacrylates, polydioxanones, poly(α-hydroxy acids), poly(β-hydroxy acids), and polyphosphazenes;

the non-water soluble polycationic polymer is selected from the group consisting of polycationic chitosan, polycationic polylysine, cholestyramine and the polycationic copolymers of acrylic and methacrylic acid esters with trimethylammonioethyl methacrylate chloride;

the active principle is selected from the group consisting of insulin, heparin, unfractionated heparin, low molecular weight heparin, ultra low molecular weight heparin, heparinoid, heparin having a molecular weight between 2,500 D and 40,000 D, antibiotics, anti-inflammatory agents, anti-infectious agents, antiparasitic agents, hormones, substances with immunological activity, vaccines, immunomodulators, immunosuppressants, cytostatic agents, diuretics, agents with activity in the digestive system, agents with activity in the circulatory system, agents with activity in the respiratory system, human growth hormone, recombinant growth hormone, bovine growth hormone, growth-hormone releasing hormone, interferons, analgesics, agents with activity in the central nervous system, erythropoietin, somatostatin, gonadotropin-releasin hormone, follicle-stimulating hormone, oxytocin, vasopressin, parathyroid hormone, adrenocorticotropin, gonadotropin-releasing hormone, thrombopoietin, calcitonin, interferons, interleukins, dermatan, glucosamines, chondroitins, auricular natriuretic factor monoclonal antibodies, protease inhibitors, filgrastim, prostaglandins (PGE2 and PGI2), cyclosporin, cromolyn sodium cromoglycate and its salts, vasopressin, vancomycin, neomycin, desferrioxamine, antimicrobial agents, antifungals, cytostatics, immunomodulators, vitamins, antivirals, antigens, ribonucleic acid, deoxyribonucleic acid, oligonucleotides, CPG sequences, plasmids, active compounds of protein nature, active compounds of polysaccharide nature glucocerebrosidase, and derivatives and combinations thereof;

the biodegradable polymer and the polycationic polymer are present in equivalent amounts; and the biodegradable polymer and the polycationic polymer are non-enteric.

2. The method of claim 1, wherein the disease is a thromboemoblic disease.

3. The method of claim 2, wherein the particulate vector is in the form of nanoparticles or microparticles.

4. The method of claim 3, wherein the particulate vector is a granule or pellet, having an average particle diameter in the range of 0.1 to 1.2 mm or of at least 1 mm.

5. The method of claim 1, wherein less than 20% wt. of the active compound is distributed on the surface of the particulate vector; and at least 80% wt. of the active compound is embedded within or surrounded by the polymeric matrix of the particulate vector.

6. The method of claim 1, wherein the particulate vector provides a release of at least 50% of active principle that is available for immediate release within 2 hours or less after the particulate vector is exposed to an aqueous environment; or wherein the particulate vector provides a release of at least 60% of active principle that is available for immediate release within 3 hours or less after the particulate vector is exposed to an aqueous environment.

7. The method of claim 6, wherein at least 20% of the active principle that is available for immediate release from the pharmaceutical form is absorbed via the mucosa of the subject following administration of the particulate vector to the subject.

8. The method of claim 7, wherein the mucosa is selected from the group consisting of oropharyngeal mucosa, gastrointestinal mucosa, pulmonary mucosa, nasal mucosa and vaginal mucosa.

9. The method of claim 1, wherein the vector further comprises one or more substances selected from the group consisting of enteric polymers and water-soluble or liposoluble substances.

10. The method of claim 1, wherein the at least one biodegradable polymer comprises at least one neutral polymer or at least one anionic polymer.

11. The method of claim 10, wherein at least one polymer of anionic or neutral nature and at least one polymer of cationic nature are present in a proportion of at least 10% each in relation to the weight of the polymeric matrix.

12. The method of claim 10, wherein the polymeric matrix comprises poly-ε-caprolactone as a polymer of anionic or neutral nature and a polymer derived from methacrylic acid with quaternary ammonium groups as a polymer of cationic nature, and the polymer derived from methacrylic acid with quaternary ammonium groups is a trimethylammonioethyl methacrylate chloride copolymer.

13. The method of claim 10, wherein the cationic polymer is a polymer derived from methacrylic acid with quaternary ammonium groups, and the biodegradable polymer is a polyethylene and polypropylene oxide copolymer, PLGA, or poly-ε-caprolactone.

14. The method of claim 1, wherein the at least one active principle is encapsulated within the polymeric matrix.

15. The method of claim 1, wherein the polymeric matrix comprises the at least one active principle, and the mixture of the at least one biodegradable polymer and the at least one non-water soluble polycationic polymer.

16. The method of claim 4, wherein the particulate vector is a granule comprising a core and the polymeric matrix, wherein said core comprises the at least one active compound.

17. The method of claim 16, wherein the polymeric matrix forms part of the core, or the polymeric matrix forms a coating layer on or over the core.

18. The method of claim 17, wherein the particulate vector further comprises an intermediate layer between the core and the coating layer.

19. The method of claims 17, wherein the core comprises an inert seed and a coating layer comprising the active compound.

20. The method of claim 19, wherein the particulate vector further comprises an intermediate layer between the inert seed and the layer comprising the active compound.

21. The method of claim 4, wherein the particulate vector is a pellet manufactured by a granulation process which comprises the step of subjecting a composition comprising at least one active compound to a granulation process to produce a core.

22. The method of claim 21, wherein the manufacturing process further comprises the step of coating the core with a composition comprising the at least one cationic polymer.

23. The method of claim 1, wherein the particulate vector has a surface potential in the range of $-17.3\pm1.35$ mV to $-37.2\pm3.3$ mV.

24. The method of claim 23, wherein the particulate vector has a surface potential of $-17.3\pm1.35$, $-20\pm0.67$, $-29.9\pm0.39$, $-30.7\pm2.02$, $-33.6\pm1.93$, $-37.2\pm3.30$.

25. The method of claim 1, wherein the particulate vector comprises:

a) a copolymer of methacrylic acid polyesters with a proportion of trimethylammonioethyl methacrylate chloride, and a copolymer of lactic acid and of glycolic acid;
b) a copolymer of lactic acid and of glycolic acid;
c) a copolymer of methacrylic acid polyesters with a proportion of trimethylammonioethyl methacrylate chloride, and poly-ε-caprolactone; or
d) poly-ε-caprolactone.

26. The method of claim 1, wherein the at least one active principle is selected from the group consisting of enoxaparin, tinzaparin, bemiparin, fondaparinux and insulin.

27. The method of claim 1, wherein the particulate vector is included in a pharmaceutical composition comprising the particulate vector and a pharmaceutically acceptable excipient.

28. The method of claim 27, wherein the at least one active principle is standard heparin which is administered at a dose of between 2,000 IU/day and 20,000 IU/day, or is LMWH which is administered at a dose of between 600 IU/day and 4,200 IU/day.

29. The method of claim 27, wherein the pharmaceutical composition is adapted for oral, peroral, sublingual, intraduodenal, intrajejunal, intraileal, intracolonic, rectal, intravaginal, nasal, intrapulmonary, ocular and/or otic administration.

30. The method of claim 29, wherein the pharmaceutical composition is a non-extended release formulation.

31. The method of claim 29, wherein the pharmaceutical composition is an oral formulation.

32. The method of claim 1, wherein less than 95% of the active compound present in the particulate vector is degraded in the gastric region following oral administration of the particulate vector to a subject.

33. The method of claim 18, wherein the particulate vector is manufactured by a coating process which comprises the steps of:
   a) coating an inert seed with a composition comprising at lest one active compound to obtain a core, and
   b) coating the core prepared in a) with a composition comprising at least a polymer of cationic nature.

34. The method of claim 33, wherein the process further comprises in step a) coating the inert seed with a composition, to form an intermediate coating layer before performing the coating with a composition comprising at least one active compound.

35. The method of claim 33, wherein, in step b) the composition further comprises at least one polymer of anionic or neutral nature.

36. The method of claim 33 wherein, in the manufacture process, a spray method is used in step b).

37. The method of claim 33 wherein, the manufacture process further comprises coating the core with a composition to form an intermediate coating layer.

38. The method of claim 15, wherein the particulate vector is manufactured by an extrusion process which comprises the steps of:
   a) mixing at least one active compound with at least one polymer of cationic nature, and
   b) extruding the homogenized mixture.

39. The method of claim 38 wherein in step a) the active compound is further mixed with at least one polymer of anionic or neutral nature.

40. The method of claim 1, wherein the active compound is selected from the group consisting of insulin, heparin, unfractionated heparin, low molecular weight heparin, ultra low molecular weight heparin, heparinoid and heparin having a molecular weight between 2,500 D and 40,000 D.

* * * * *